United States Patent
Tuszynski et al.

(10) Patent No.: US 9,458,101 B2
(45) Date of Patent: Oct. 4, 2016

(54) COLCHICINE DERIVATIVES, METHODS AND USES THEREOF

(75) Inventors: Jack Tuszynski, Edmonton (CA); Jonathan Y. Mane, Stony Plain (CA); John Torin Huzil, Waterdown (CA); Boguslaw Tomanek, Calgary (CA); Dorota Bartusik, Bedziemysl (PL)

(73) Assignee: NATIONAL RESEARCH COUNCIL OF CANADA, Edmonton Alberta (CA)

( * ) Notice: Subject to any disclaimer, the term of this patent is extended or adjusted under 35 U.S.C. 154(b) by 763 days.

(21) Appl. No.: 13/392,454

(22) PCT Filed: Jul. 30, 2010

(86) PCT No.: PCT/CA2010/001199
§ 371 (c)(1),
(2), (4) Date: May 4, 2012

(87) PCT Pub. No.: WO2011/022805
PCT Pub. Date: Mar. 3, 2011

(65) Prior Publication Data
US 2012/0225912 A1 Sep. 6, 2012

Related U.S. Application Data

(60) Provisional application No. 61/240,132, filed on Sep. 4, 2009, provisional application No. 61/237,142, filed on Aug. 26, 2009.

(51) Int. Cl.
*A61K 31/27* (2006.01)
*C07C 323/41* (2006.01)
(Continued)

(52) U.S. Cl.
CPC ........... *C07C 323/41* (2013.01); *C07C 233/32* (2013.01); *C07C 237/22* (2013.01);
(Continued)

(58) Field of Classification Search
CPC .......................... C07C 2010/14; C07C 271/44
USPC ....................................................... 514/480
See application file for complete search history.

(56) References Cited

U.S. PATENT DOCUMENTS 4,533,675 A * 8/1985 Brossi et al. ................. 514/480
5,175,342 A 12/1992 Brossi
7,622,612 B2 11/2009 Chang et al.

FOREIGN PATENT DOCUMENTS

FR 1344474 11/1963
GB 763217 12/1956
(Continued)

OTHER PUBLICATIONS

Andreu, J.M., et al., "Conformational States of Tubulin Liganded to Colchicine, Tropolone Methyl Ether, and Podophyllotoxin;" American Chem. Society, pp. 6465-6476, 1982.
(Continued)

*Primary Examiner* — San-Ming Hui
(74) *Attorney, Agent, or Firm* — Ohlandt, Greeley, Ruggiero & Perle, LLP

(57) ABSTRACT

The invention relates to colchicine derivatives, methods and uses thereof for treatment of cancer. In certain embodiments, the colchicine derivative comprises a compound of Formula I:

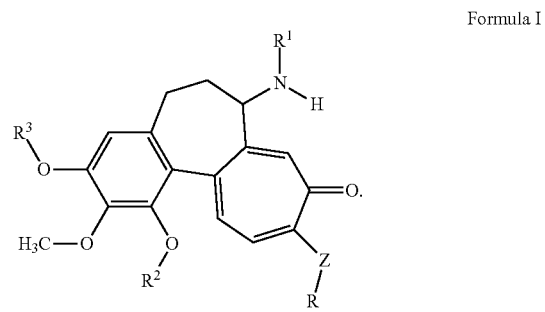

Formula I

7 Claims, 26 Drawing Sheets

(51) Int. Cl.

| | |
|---|---|
| C07C 233/32 | (2006.01) |
| C07C 237/22 | (2006.01) |
| C07C 271/24 | (2006.01) |
| C07C 323/61 | (2006.01) |
| G01N 33/50 | (2006.01) |

(52) U.S. Cl.
CPC ......... *C07C271/24* (2013.01); *C07C 323/61* (2013.01); *G01N 33/5088* (2013.01); C07C 2103/34 (2013.01); G01N 2500/10 (2013.01)

(56) References Cited

FOREIGN PATENT DOCUMENTS

| | | |
|---|---|---|
| JP | 0967326 | 3/1997 |
| WO | 9611184 A1 | 4/1996 |
| WO | WO96/11184 | 4/1996 |
| WO | WO97/01570 | 1/1997 |
| WO | WO2004/113281 | 12/2004 |
| WO | WO2004/113281 A1 | 12/2004 |
| WO | WO2005/007076 | 1/2005 |
| WO | WO2005/007076 A2 | 1/2005 |
| WO | 2011004980 A2 | 1/2011 |
| WO | 2011/021397 | 2/2011 |

OTHER PUBLICATIONS

Bai, R., et al., "Dolastin 10, a Powerful Cytostatic Peptide Derived from a Marine Animal;" Biochemical Pharmacology, vol. 39, No. 12, pp. 1941-1949, 1990.
Banerjee, A., et al., "A Monoclonal Antibody against the Type II Isotype of B-Tubulin;" The Journal of Biological Chem., vol. 263, No. 6, pp. 3029-3034, 1988.
Banerjee, A., et al., "Kinetics of Colchicine Binding to Purified B-Tubulin Isotypes from Bovine Brain;" The Journal of Biological Chem., vol. 267, No. 19, pp. 13335-13339, 1992.
Banerjee, A., "Increased levels of tyrosinated x, BIII-, and BIV-tubulin isotypes in paclitaxel-resistant MCF-7 breast cancer cells;" Biochemical and Biophysical Research Communications 293, 2002, pp. 598-601.
Bartusik, D., et al., "Derivatives of thiocolchicine and its applications to CEM cells treatment using 19F Magnetic Resonance ex vivo;" Bioorganic Chemistry 38, 2010, pp. 1-6.
Bollag, D.M., et al., "Epothilones, a New Class of Microtubule-stabilizing Agents with a Taxol-like Mechanism of Action;" Cancer Research 55, Jun. 1995, pp. 2325-2333.
Borisy, G.G., et al., "The Mechanism of Action of Colchicine;" J. Cell. Biol., Aug. 1967, (downloaded from jcb.rupress.org, Feb. 9, 2012), pp. 525-533.
Borisy, G.G. et al., "The Mechanism of Action of Colchicine;" J. Cell. Biol., Aug. 1967, (downloaded from jcb.rupress.org, Feb. 9, 2012), pp. 535-548.
Brooks, B.R., et al., "CHARMM: The Biomolecular Simulation Program;" J Comput Chem 30: 2009, pp. 1545-1614.
Callen, J.P., "Colchicine is effective in controlling chronic cutaneous leukocytoclastic vasculitis;" J Am Acad Dermatol 13, 1985, pp. 193-200.
Chaudhuri, A.R., et al. "The Interaction of the B-ring of Colchicine with x-Tubulin: A Novel Footprinting Approach;" J. Mol. Biol, 303, 2000, pp. 679-692.
Cragg, G.M., et al., "Anticancer Agents from Natural Products;" CRC Press, 2005, 4 pp., (Summary only).
Cucchiarelli, V., et al., "B-Tubulin Isotype Classes II and V Expression Patterns in Nonsmall Cell Lung Carcinomas;" Cell Motility and the Cytoskeleton 65, 2008, pp. 675-685.
Fellous, A., et al., "Microtubule Assembly in vitro;" Eur. J. Bochem. 78, 1977, pp. 167-174.
Garland, D.L., "Kinetics and Mechanism of Colchicine Binding to Tubulin: Evidence for Ligand-Induced Conformational Change;" Biochemistry, Am. Chem. Society, 1978, pp. 4266-4272.

Gigant, B., et al., "Structural basis for the regulation of tubulin by vinblastine;" Nature Publishing Group, vol. 435, May 2005, pp. 519-522.
Hoebeke, J., et al., "Interaction of Oncodazole (R 17934), a New Anti-Tumoral Drug, with Rat Brain Tubulin;" Biochemical and Biophysical Research Communication, vol. 69, No. 2, 1976, pp. 319-324.
Huzil, J.T., et al., "Comparative modelling of human B tubulin isotypes and implications for drug binding;" Institute of Physics Publishing, Nanotechnology 17, 2006, pp. S90-S100.
Katsetos, C.D., et al., "Differential Distribution of the Neuron-Associated Class III B-Tubulin in Neuroendocrine Lung Tumors;" Arch Pathol Lab Med., vol. 124, Apr. 2000, pp. 535-544.
Katsetos, C.D., et al., "Class III B-Tubulin Isotype: A Key Cytoskeletal Protein at the Crossroads of Developmental Neurobiology and Tumor in Neuropathology;" J Child Neurol 2003, pp. 851-866.
Kavallaris, M., et al., "Taxol-resistant Epithelial Ovarian Tumors Are Associated with Altered Expression of Specific B-Tubulin Isotypes;" J. Clin. Invest., vol. 100, No. 5, Sep. 1997, pp. 1282-1293.
Kerekes, P., et al., "Synthesis and Biological Effects of Novel Thiocolchicines. 3. Evaluation of N-Acyldeacetylthiocolchicines, N-(Alkoxycarbonyl)deacetylthiocolchicines, and O-Ethyldemethylthiocolchicines. New Synthesis of Thiodemecolcine and Antileukemic Effects of 2-Demethyl- and 3-Demethylthiocolchicine;" J. Med. Chem. 28, 1985, pp. 1204-1208.
Khan, I.A., et al., "Different effects of vinblastine on the polymerization of isotypically purified tubulins from bovine brain;" Investigational New Drugs 21, 2003, pp. 3-13.
Laclette, J.P., et al., "Inhibition of Tubulin Polymerization by Mebendazole;" Biochemical and Biophysical Research Communications, vol. 92, No. 2, Jan. 29, 1980, pp. 417-423.
Lindahl, E., et al., "GROMACS 3.0: a package for molecular simulation and trajectory analysis;" J Mol Model 7, 2001, pp. 306-317.
Loewe, J., et al., "Refined Structure of xB-Tubulin at 3.5 A Resolution;" J. Mol. Biol. 313, 2001, pp. 1045-1057.
Lu, Q., et al., "In Vitro Analysis of Microtubule Assembly of Isotypically Pure Tubulin Dimers;" The Journal of Biological Chem., vol. 269, No. 3, Issue of Jan. 21, 1994, pp. 2041-2047.
Luduena, R.F., et al., "Interaction of Bovine Brain Tubulin with the 4(1H)-Pyrizinone Derivative IKP104, an Antimitotic Drug with a Complex Set of Effects on the Conformational Stability of the Tubulin Molecule;" Biochemistry, 34, 1995, pp. 15751-15759.
Luduena, R.F., "Multiple Forms of Tubulin: Different Gene Products and Covalent Modifications;" International Review of Cytology, vol. 178, 1997, pp. 207-275.
Mekori, Y.A., et al., "Inhibition of Delayed Hypersensitivity Reactions in Mice by Colchicine;" Cellular Immunology 120, 1989, pp. 330-340.
Muzaffar, A., et al., "Antitubulin Effects of Derivatives of 3-Demetylthiocolchicine, Methylthio Ethers of Natural Colchicinoids, and Thioketones Derived from Thiocolchicine Comparison with Colchicinoids;" J. Med. Chem., 33, 1990, 567-571.
Nogales, E., et al., "Structure of tubulin at 6.5 A and location of the taxol-binding site;" Nature, vol. 375, Jun. 1995, pp. 424-427.
Owellen, R.J., et al., "The Binding of Vincristine, Vinblastine and Colchicine to Tubulin;" Biochemical and Biophysical Research Communications, vol. 47, No. 4, 1972, pp. 685-691.
Ravelli, R.B.G., et al., "Insight into tubulin regulation from a complex with colchicine and a stathmin-like domain;" Nature Publishing Group, vol. 428, Mar. 2004, pp. 198-202.
Roach, M.C., et al., "Preparation of a Monoclonal Antibody Specific for the Class I Isotype of B-Tubulin: The B Isotypes of Tubulin Differ in Their Cellular Distributions Within Human Tissues;" Cell Motility and the Cytoskeleton 39, 1998, pp. 273-285.
Rosenman, S.J., et al., "Contact-Dependent Redistribution of Cell Surface Adhesion and Activation Molecules in Lymphocyteendothelial Cell Interactions Involves Cytoskeletal Reorganization;" FASEB Journal, vol. 5, No. 6, 1991, p. 1603.

(56) References Cited

OTHER PUBLICATIONS

Russell, G.J., et al., "Inhibition of [3H}Mebendazole Binding to Tubulin by Structurally Diverse Microtubule Inhibitors Which Interact at the Colchicine Binding Site;" Biochemistry and Molecular Biology International, vol. 35, No. 6, May 1995, pp. 1153-1159.
Sackett, D.L., et al., "Molecular Mechanism of Colchicine Action: Induced Local Unfolding of B-Tubulin;" Bochemistry, 32, 1993, pp. 13560-13565.
Schiff, P.B., et al., "Promotion of microtubule assembly in vitro by taxol;" Nature, vol. 277, Feb. 1979, pp. 665-667.
Schwarz, P.M., et al., "B-Tubulin Isotypes Purified from Bovine Brain Have Different Relative Stabilities;" Biochemistry, 37, 1998, pp. 4687-4692.
Scott, C.A., et al., "B-Tubulin Epitope Expression in Normal and Malignant Epithelial Cells;" Arch Otolaryngol Head Neck Surg—vol. 116, May 1990, pp. 583-589.
Seideman, P., et al., "Psoriatic Arthritis Treated with Oral Colchicine;" J Rheumatol, 14, 1987, pp. 777-779.
Tahir, S.K., et al., "Rapid Colchicine Competition-Binding Scintillation Proximity Assay Using Biotin-Labeled Tubulin;" BioTechniques 29, Jul. 2000, pp. 156-160.
Tommasi, S., et al., "Cytoskeleton and paclitaxel sensitivity in breast cancer: The role of B-tubulins;" Int. J. Cancer: 120, 2007, pp. 2078-2085.
Wu, G., et al., "Detailed Analysis of Grid-Based Molecular Docking: A Case Study of CDOCKER-A CHARMm-Based MD Docking Algorithm;" J Comput Chem 24, 2003, pp. 1549-1562.
Xu, K., et al., "Interaction of Nocodazole With Tubulin Isotypes;" Drug Development Research 55, 2002, pp. 91-96.
Answer 3 of 3 of Caplus Copyright 2010 ACS on STN, 1 page.
Seligman, Arnold M., et al., "Design of Spindle Poisons Activated Specifically by Prostatic Acid Pohosphatase (PAP) and New Methods for PAP Cytochemistry;" Cancer Chemotherapy Reports, Part 1, vol. 59, No. 1, pp. 233-242, Jan./Feb. 1975.
Paul, Buddha D., et al., "New Agents for Prostatic Cancer Activated Specifically by Prostatic Acid Phosphatase;" Cancer Treatment Reports, vol. 61, No. 2, pp. 259-263, Mar./Apr. 1977.
Ducray, P, et al., "Synthesis of Lipid Derivatives of Colchicine;" Helvetica Chimica Acta, vol. 79, pp. 2346-2352, 1996.
Gelmi, M. L., "N-Deacetyl-N-aminoacylthiocolchicine Derivatives: Synthesis and Biological Evauation on MDR-Positive and MDR-Negative Human Cancer Cell Lines;" J. Med. Chem., 42, pp. 5272-5276, 1999.
Cifuentes, M., et al., "Sytnthesis and biological evaluation of B-ring modified colchicine and isocolchicine analogs;" Bioorganic and Medicianl Chemistry Letters 16, pp. 2761-2764, 2006.

Mane, J. Y., et al., "Free Energy Calculations on the Binding of Colchicine and Its Derivatives with the a/b-Tubulin Isoforms;" J. Chem. Inf. Model, 48, pp. 1824-1832, 2008.
Alam, Afroz, Md., et al., "Applying linear interaction energy method for binding affinity calculations of podophyllotoxin analogues with tubulin using continuum solvent model and prediction of cytotoxic activity;" Journal of Molecular Graphics and Modelling 27, pp. 930-943, 2009.
Batursik, D. et al., "The efficacy of new colchicine derivatives and viability of the T-Lymphoblastoid cells in three-dimensional culture using 19F MRI and HPLC-UV ex vivo;" Bioorganic Chemistry 37, pp. 193-201, 2009.
Huzil, J. T., et al., "Computational Design and Biological Testing of Highly Cytotoxic Colchicine Ring A Modifications;" Chem Biol Drug Des, 75, pp. 541-550, 2010.
Answers 23 of 76 of Registry Copyright 2010 ACS on STN, 23 pp.
Invitation Pursuant to Rule 62(a) EPC and Rule 63(1) EPC from European Application No. 10 811 047.9-1211 dated Dec. 6, 2012.
Extended European Search Report from European Application No. 10 811 047.9-1211 dated Feb. 22, 2013.
International Search Report dated Nov. 2, 2010 in counterpart International Application No. PCT/CA2010/001199.
Japanese Office Action (with English Translation) dated Aug. 15, 2014, corresponding to Japanese Application No. 2012-525826, 22 pages.
Muzaffar et al.; "Antiubulin Effects of Derivates of 3-Demethylthiocolchicine, Methylthio Ethers of Natural Colchicinoids, and Thioketones Derived from Thiocolchicine Comparison with Colchicinoids"; J. Med. Chem. 1990, 33, pp. 567-571.
Karekes et al.; "Synthesis and Biological Effects of Novel Thiocolchicines. 3. Evaluation of N-Aclydeacetylthiocolchicines, N-(Alkoxycarbonyl) deacetylthiocolchicines, and O-Ethyldemethylthiocolchicines. New Synthesis of Thiodemecolcine and Antileukemic Effects of 2-Demethyl- and 3-Demethylthiocolchicine"; J. Med. Chem. 1988, 28, pp. 1204-1208.
Walterova et al.; "Circular Dichroic Spectra and Ionization Processes of Some Tropolonic Alkaloids"; Heterocycles, vol. 25, 1987, pp. 9.
Vilar et al.; "Probalistic Neutral Network Model for the in Silico Evaluation of Anti-HIV Activity and Mechanism of Action"; J. Med. Chem. 2006, 49, pp. 1118-1124.
Daniel et al.; "Attempted Oxidative Deamination of N-Deacetylcolchicinoids With 3,5-Di(Tert-Butyl)-1,2-Benzoquinone: Synthesis of 2H-1,4-Benzoxazine-Type Adducts"; Helvetica Chimica Acta- vol. 82 (1999), pp. 7.
Bartusik et al.; "The Efficacy of New Colchicine Derivatives and Viability of the T-Lymphoblastoid Cells in Three-Dimensional Culture Using 19 F MRI and HPLC-UV Ex vivo"; Bioorganic Chemistry 37 (2009), pp. 193-201.

* cited by examiner

FIG. 3

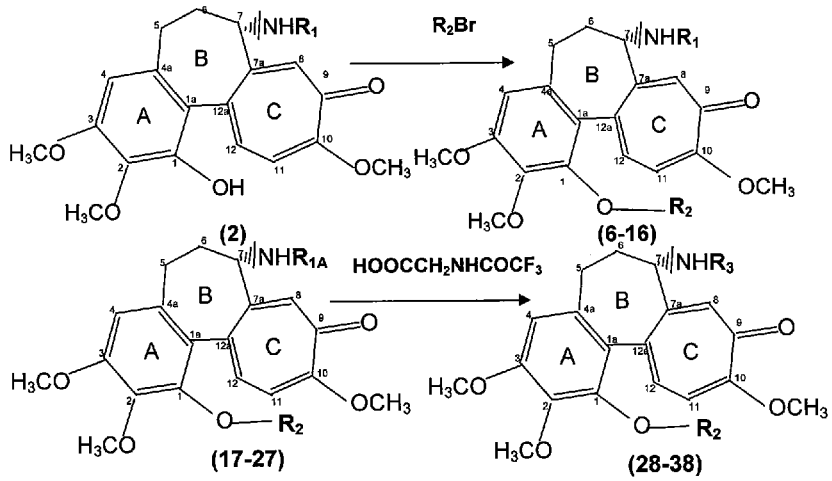

(6) $R_2 = CH_2CH_3$; $R_1 = COCH_3$
  (6a) $R_2 = CH_3$; $R_1 = COCH_3$ (7) $R_2 = CH(CH_3)_2$; $R_1 = COCH_3$ (7a) $R_2 = CH_2CH(CH_3)_2$; $R_1 = COCH_3$ (7b) $R_2 = CH_2(CH_2)_2CH_3$; $R_1 = COCH_3$ (7c) $R_2 = CH_2CH_2CH=CH_2$; $R_1 = COCH_3$ (8) $R_2 = (CH_2)_2CH_3$; $R_1 = COCH_3$ (9) $R_2 = CH_2CH=CH_2$; $R_1 = COCH_3$

(10) $R_2 = CH_2(C_6H_5)$; $R_1 = COCH_3$

(11) $R_2 = CH_2CH_2OCH_3$; $R_1 = COCH_3$

(12) $R_2 = CH_2(C_6H_4)$-m-Cl; $R_1 = COCH_3$

(13) $R_2 = CH_2(C_5H_4N)$; $R_1 = COCH_3$

(14) $R_2 = CH_2(C_6H_4)$-o-Cl; $R_1 = COCH_3$

(15) $R_2 = CH_2(C_6H_4)$-p-Cl; $R_1 = COCH_3$

(16) $R_2 = CH_2(C_6H_{11})$; $R_1 = COCH_3$

(17) $R_2 = CH_2CH_3$; $R_{1A} = H$
  (17a) $R_2 = CH_3$; $R_{1A} = H$

(18) $R_2 = CH(CH_3)_2$; $R_{1A} = H$

(19) $R_2 = (CH_2)_2CH_3$; $R_{1A} = H$

(20) $R_2 = CH_2CH=CH_2$; $R_{1A} = H$

(21) $R_2 = CH_2(C_6H_5)$; $R_{1A} = H$

(22) $R_2 = CH_2CH_2OCH_3$; $R_{1A} = H$

(23) $R_2 = CH_2(C_6H_4)$-m-Cl; $R_{1A} = H$

(24) $R_2 = CH_2(C_5H_4N)$; $R_{1A} = H$

(25) $R_2 = CH_2(C_6H_4)$-o-Cl; $R_{1A} = H$

(26) $R_2 = CH_2(C_6H_4)$-p-Cl; $R_{1A} = H$

(27) $R_2 = CH_2(C_6H_{11})$; $R_{1A} = H$

(28) $R_2 = CH_2CH_3$; $R_3 = COCH_2NHCOCF_3$
  (28a) $R_2 = CH_3$; $R_3 = COCH_2NHCOCF_3$

(29) $R_2 = CH(CH_3)_2$; $R_3 = COCH_2NHCOCF_3$

(30) $R_2 = (CH_2)_2CH_3$; $R_3 = COCH_2NHCOCF_3$

(31) $R_2 = CH_2CH=CH_2$; $R_3 = COCH_2NHCOCF_3$

(32) $R_2 = CH_2(C_6H_5)$; $R_3 = COCH_2NHCOCF_3$

(33) $R_2 = CH_2CH_2OCH_3$; $R_3 = COCH_2NHCOCF_3$

(34) $R_2 = CH_2(C_6H_4)$-m-Cl; $R_3 = COCH_2NHCOCF_3$

(35) $R_2 = CH_2(C_5H_4N)$; $R_3 = COCH_2NHCOCF_3$

(36) $R_2 = CH_2(C_6H_4)$-o-Cl; $R_3 = COCH_2NHCOCF_3$

(37) $R_2 = CH_2(C_6H_4)$-p-Cl; $R_3 = COCH_2NHCOCF_3$

(38) $R_2 = CH_2(C_6H_{11})$; $R_3 = COCH_2NHCOCF_3$

(50) R = (—OH); $R_1$ = (—COCH$_3$)

(51) R = (—OCH$_2$CH$_2$CH=CH$_2$); $R_1$= (—COCH$_3$)

(52) R = (—OCH$_2$CH(CH$_3$)$_2$); $R_1$= (—COCH$_3$)

(53) R = (—OCH$_2$CH$_2$CH$_3$); $R_1$= (—COCH$_3$)

(54) R = (—OCH$_2$(CH$_2$)$_2$CH$_3$); $R_1$ = (—COCH$_3$)

(39) $R = (-OCH_3); R_1 = (-COCH_3)$

(40) $R = (-OH); R_1 = (-COCH_3)$

(41) $R = (-OCH_2CH=CH_2); R_1 = (-COCH_3)$

(42) $R = (-OCH_2CH_3); R_1 = (-COCH_3)$

(43) $R = (-OCH_2CH_2CH_3); R_1 = (-COCH_3)$

(44) $R = (-OH); R_1 = (-H)$

(45) $R = (-OCH_2CH=CH_2); R_1 = (-H)$

(46) $R = (-OCH_2CH_3); R_1 = (-H)$

(47) $R = (-OH); R_1 = (-COCH_2NHCOCF_3)$ (47a) $R = (-OCH_3); R_1 = (-COCH_2NHCOCF_3)$

(48) $R = (-OCH_2CH=CH_2); R_1 = (-COCH_2NHCOCF_3)$

(49) $R = (-OCH_2CH_3); R_1 = (-COCH_2NHCOCF_3)$

FIG. 4A

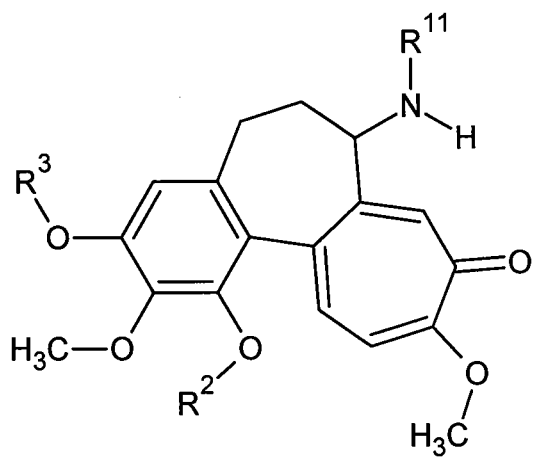

(55) $R^3$ = $CH_3$; $R^2$ = $CH_2CH_2CH_3$; $R^{11}$ = (C=O)H

(56) $R^3$ = $CH_3$; $R^2$ = $CH_2CH_2CH_3$; $R^{11}$ = $OCH_3$

(57) $R^3$ = $CH_3$; $R^2$ = $CH_2CH_2CH_3$; $R^{11}$ = H

(58) $R^3$ = $CH_3$; $R^2$ = $CH(CH_3)_2$; $R^{11}$ = (C=O)H

(59) $R^3$ = $CH_3$; $R^2$ = $CH(CH_3)_2$; $R^{11}$ = $OCH_3$

(60) $R^3$ = $CH_3$; $R^2$ = $CH(CH_3)_2$; $R^{11}$ = H

(61) $R^3$ = $CH_3$; $R^2$ = $CH_2CH(CH_3)_2$; $R^{11}$ = (C=O)H

(62) $R^3$ = $CH_3$; $R^2$ = $CH_2CH(CH_3)_2$; $R^{11}$ = $OCH_3$

(63) $R^3$ = $CH_3$; $R^2$ = $CH_2CH(CH_3)_2$; $R^{11}$ = H

(64) $R^3$ = $CH_3$; $R^2$ = $CH_2CH=CH_2$; $R^{11}$ = (C=O)H

(65) $R^3$ = $CH_3$; $R^2$ = $CH_2CH=CH_2$; $R^{11}$ = $OCH_3$

(66) $R^3$ = $CH_3$; $R^2$ = $CH_2CH=CH_2$; $R^{11}$ = H

(67) $R^3$ = H; $R^2$ = $CH_3$; $R^{11}$= (C=O)H

(68) $R^3$ = H; $R^2$ = $CH_3$; $R^{11}$= $OCH_3$

(69) $R^3$ = H; $R^2$ = $CH_3$; $R^{11}$= H

(70) $R^3$ = $CH_2CH_3$; $R^2$ = $CH_3$; $R^{11}$= (C=O)H

(71) $R^3$ = $CH_2CH_3$; $R^2$ = $CH_3$; $R^{11}$= $OCH_3$

(72) $R^3$ = $CH_2CH_3$; $R^2$ = $CH_3$; $R^{11}$= H

(73) $R^3$ = $CH_2CH_2CH_3$; $R^2$ = $CH_3$; $R^{11}$= (C=O)H

(74) $R^3$ = $CH_2CH_2CH_3$; $R^2$ = $CH_3$; $R^{11}$= $OCH_3$

(75) $R^3$ = $CH_2CH_2CH_3$; $R^2$ = $CH_3$; $R^{11}$= H

(76) $R^3 = CH_3$; $R^2 = CH_2CH_2CH_3$

(77) $R^3 = CH_3$; $R^2 = CH(CH_3)_2$

(78) $R^3 = CH_3$; $R^2 = CH_2CH(CH_3)_2$

(79) $R^3 = CH_3$; $R^2 = CH_2CH=CH_2$

(80) R³ = H; R² = CH₃

(81) R³ = CH₂CH₃; R² = CH₃

(82) R³ = CH₂CH₂CH₃; R² = CH₃

(83) $R^3$ = $CH_3$; $R^2$ = $CH_2CH_3$; $R^{10}$ = $CH_3$

(84) $R^3$ = $CH_3$; $R^2$ = $CH_2CH_2OCH_3$; $R^{10}$ = $CH_3$

(85) $R^3$ = $CH_3$; $R^2$ = $CH_2(C_5H_4N)$; $R^{10}$ = $CH_3$

(86) $R^3$ = $CH_3$; $R^2$ = $CH_2CH_3$; $R^{10}$ = $CH_3$

(87) $R^3$ = $CH_3$; $R^2$ = $CH_2CH_2OCH_3$; $R^{10}$ = $CH_3$

(88) $R^3$ = $CH_3$; $R^2$ = $CH_2(C_5H_4N)$; $R^{10}$ = $CH_3$

(89) $R^3$ = H; $R^2$ = $CH_3$; $R^{10}$ = $CH_3$

(90) $R^3$ = $CH_2CH=CH_2$; $R^2$ = $CH_3$; $R^{10}$ = $CH_3$

(91) $R^3$ = $CH_2CH_3$; $R^2$ = $CH_3$; $R^{10}$ = $CH_3$

(92) $R^3$ = H; $R^2$ = $CH_3$; $R^{10}$ = $CH_3$

(93) $R^3$ = $CH_2CH=CH_2$; $R^2$ = $CH_3$; $R^{10}$ = $CH_3$

(94) $R^3$ = $CH_2CH_3$; $R^2$ = $CH_3$; $R^{10}$ = $CH_3$

A)

```
236                        312     348    367   Residue
VTTCLRFPGQLNADLRKLAVNMV    TVAAVF  NVKTAV FIG   Type I
-  -        - -   --  --   ----I   - ---  -     Type II
-  S        - -   --  --   ---T-   - -V-  -     Type III
```

B)

COLCHICINE DERIVATIVES, METHODS AND USES THEREOF

FIELD OF THE INVENTION

The present invention relates generally to colchicine derivatives, methods and uses thereof.

BACKGROUND OF THE INVENTION

Any references cited herein are incorporated by reference.

Targeted molecular medicine is an exciting research approach, aimed at developing safer and more effective drugs and treatment therapies. The structural protein tubulin is an appealing target for such investigations, as it is already known to interact with some of the most successful chemotherapy drugs, including the taxanes, Vinca alkaloids, epothilones, and dolastatins (Bai R. et al., Biochem Pharmacol. 1990; 39:1941-9; Schiff P. B. et al., Nature, 1979:277:665-7; Owellen R. J. et al., Biochem Biophys. Res. Commun. 1972; 47:685-91; and Bollag D. M. et al., Cancer Res. 1995:55: 2325-33). Unfortunately, while many of these drugs are clinically invaluable, many can affect cancerous and non-cancerous cells indiscriminately. It is this nature of many chemotherapy agents that results in the undesirable side-effects associated with these treatments.

The lack of specificity currently poses one of the greatest challenges in cancer chemotherapy. However, the expression of several β-tubulin isotypes provides a unique platform on which to develop drugs with increased specificity for only those isotypes expressed principally in cancerous cells (Lu Q. et al., J. Biol. Chem. 1994; 269:2041-7; Luduena R. F., Int. Rev. Cytol. 1998; 178:207-75; and Roach M. C. et al., Cell Motil. Cytoskeleton, 1998; 39:273-85). The currently available anti-tubulin drugs appear to bind to multiple β-tubulin isotypes, showing limited preference for one over another (Khan I. A. et al., Invest. New Drugs. 2003; 21:3-13; Banerjee A. et al., J. Biol Chem. 1992; 267:13335-9; Schwarz P. M. Drug Development Research. 2002; 55:91-6; Luduena R. F. et al., Biochem. 1995; 34:15751-9). For example, vinblastine seemingly binds with greater affinity to the βII-tubulin isotype (Khan I. A. et al., Invest. New Drugs. 2003; 21:3-13), while expression of the βIII-tubulin isotype has been correlated with resistance to anti-tubulin agents (Katsetos C. D. et al., J. Child Neurol. 2003; 18:851-66: discussion 867). A precise explanation for isotype expression has yet to be posited. However, it is evident that cancerous cells express a wide range of tubulin isotypes, not simply those present in the cells from which they are derived (Katsetos C. D. et al., Arch. Pathol. Lab Med. 2000:124: 535-44; and Scott C. A., et al., Arch Otolaryngol Head Neck Surg. 1990; 116:583-9). A chemotherapy drug selected to target a tubulin isotype expressed in cancer cells could potentially minimize or eliminate damage to non-cancerous cells.

Several structures of anti-cancer drug-tubulin complexes have now been crystallographically determined and the mechanisms of anti-mitotic action of the drugs postulated (Ravelli R. B. et al., Nature. 2004; 428:198-202; Gigant B. et al., Nature. 2005; 435:519-22; Nogales E. et al., Nature. 1995; 375:424-7). Colchicine has extremely strong anti-mitotic activity, that is only observed at toxic or near toxic levels which limits its use as a cancer treatment.

Colchicine has been widely used in immune-mediated diseases, and beneficial effects were reported in the treatment of psoriatic arthritis (P. Seidemann, B. Fjellner, A. Johannesson, J. Rheumatol. 14 (1987) 777-779) and leukocyte-cytoclastic vasculitis (J. P. Callen, J. Am. Acad. Dermatol. 13 (1987)193-200). Moreover, recent studies have showed that colchicine inhibits leukocyte-endothelial cell adhesion (S. J. Rosenman, A. A. Ganji, W. M. Gallatin, F.A.S.E.B. J. 5 (1991)1603-1609) and T cell activation (Y. A. Mekory, D. Baram, A. Goldberg, A. Klajman, Cell. Immunol. 120 (1989) 330-340) by binding to intracellular tubulin monomers, which prevents their polymerization (G. O. Borisy, E. W. Taylor, J. Cell. Biol. 34 (1967) 533-548). Thus, colchicine has the potential to impair the process of antigen recognition and may inhibit the cancer cell growth. However, antimitotic colchicine is used only in research due to its toxicity.

The effects associated with the pharmacological profile of colchicine and the frequent occurrence of drug resistance has prompted the search for compounds that are comparable to colchicine's activity and more suitable for cancer treatment.

SUMMARY OF THE INVENTION

In an aspect, there is provided a compound of Formula I:

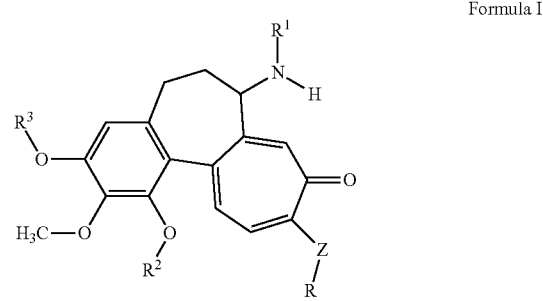

Formula I wherein:

Z is O or S;

$R^1$ is selected from H, a halo group, a substituted or unsubstituted hydrocarbon group, or a substituted or unsubstituted heterogeneous group;

$R^2$ and $R^3$ are each independently selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

R is selected from H or a substituted or unsubstituted hydrocarbon group, with the proviso that when R, $R^2$ and $R^3$ are methyl groups, $R^1$ is not —$COCH_3$;

and/or a pharmaceutically-acceptable salt, hydrate, solvate, tautomer, optical isomer, or combination thereof.

In another aspect, the compound is a compound of Formula IA:

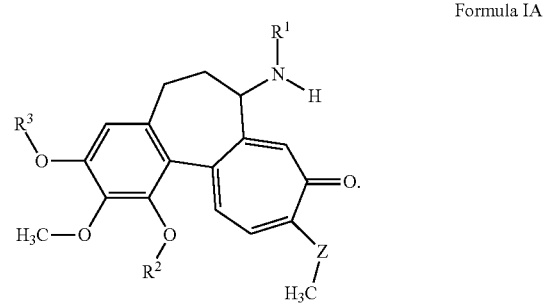

Formula IA

In another aspect, the compound is a compound of Formula II:

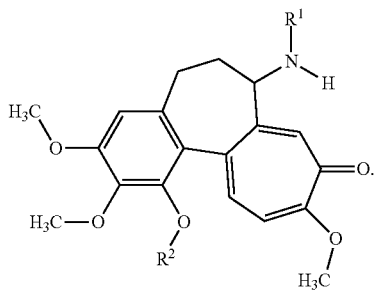

Formula II

In another aspect, the compound is a compound of Formula II:

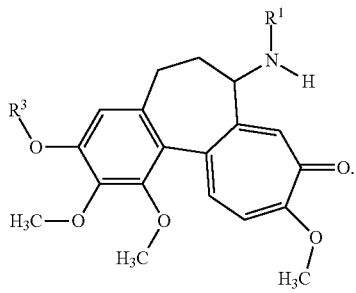

Formula IIA

In another aspect, the compound is a compound of Formula III:

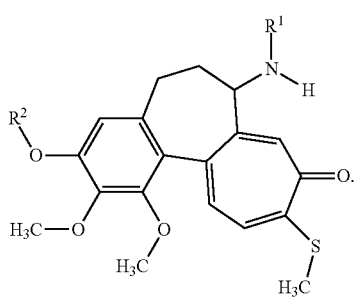

Formula III

In another aspect, there is provided a compound of Formula IB:

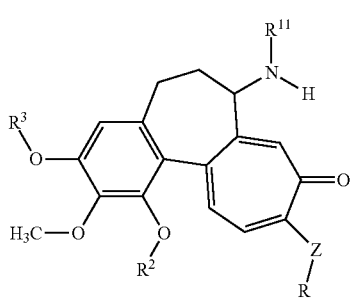

Formula IB wherein:

Z is O or S;

$R^{11}$ is selected from H, a substituted or unsubstituted alkoxy, a substituted or unsubstituted alkyl, a substituted or unsubstituted alkenyl, a substituted or unsubstituted alkynyl, a substituted or unsubstituted alkylcarbonyl, or a —(C=O)H;

$R^2$ and $R^3$ are each independently selected from H, a halo group, a substituted or unsubstituted hydrocarbon group, a substituted or unsubstituted heterogeneous group, or a substituted or unsubstituted carbocyclic group;

and/or a pharmaceutically-acceptable salt, hydrate, solvate, tautomer, optical isomer, or combination thereof.

In another aspect, the compound is a compound of Formula IC:

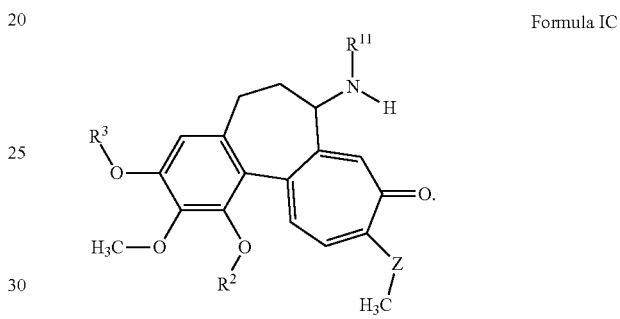

Formula IC

In another aspect, the compound is a compound of Formula ID:

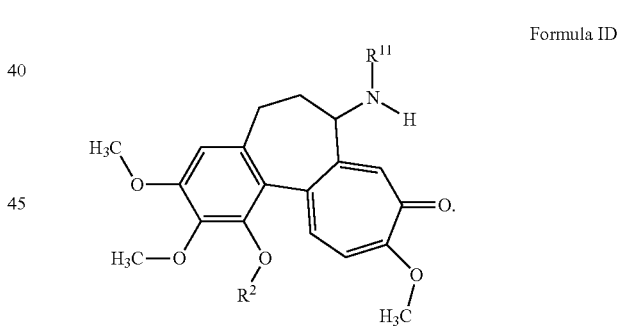

Formula ID

In yet another aspect, the compound is a compound of Formula IE:

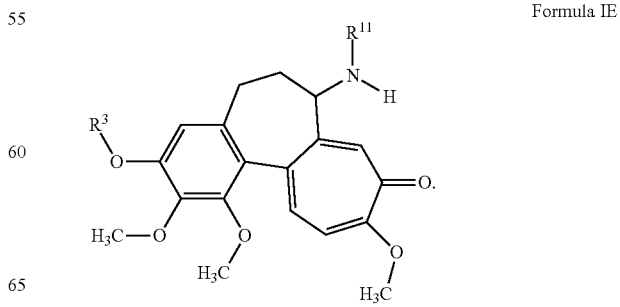

Formula IE

In another aspect, the compound is a compound of Formula IF:

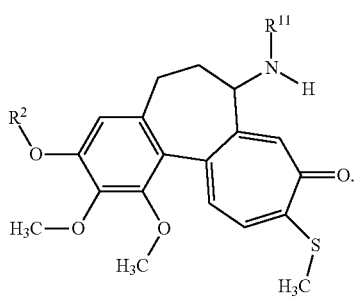

Formula IF

In yet another aspect, there is provided a compound of Formula IX:

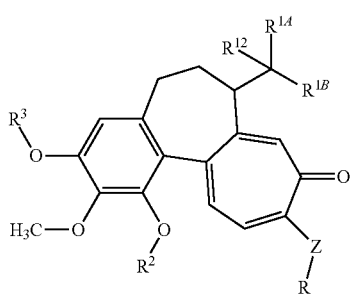

Formula IX wherein:
Z is O or S;
$R^{1A}$, and $R^{1B}$ are each independently selected from H, or a substituted or unsubstituted hydrocarbon group;
$R^{12}$ is selected from H, a substituted or unsubstituted alkoxy, a substituted or unsubstituted alkyl, a substituted or unsubstituted alkenyl, or a substituted or unsubstituted alkynyl;
$R^2$ and $R^3$ are each independently selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;
R is selected from H or a substituted or unsubstituted hydrocarbon group;
and/or a pharmaceutically-acceptable salt, hydrate, solvate, tautomer, optical isomer, or combination thereof.

In another aspect, the compound is a compound of Formula IXA:

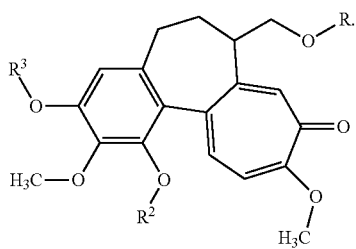

Formula IXA

In another aspect, the compound is a compound of Formula IXB:

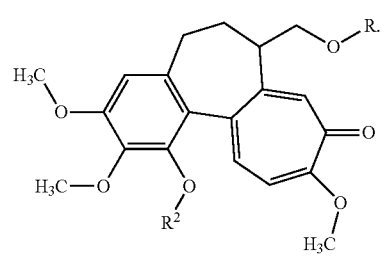

Formula IXB

In another aspect, the compound is a compound of Formula IXC:

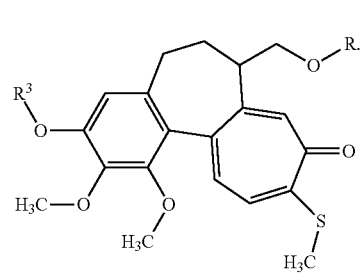

Formula IXC

In another aspect, there is provided a compound of Formula X:

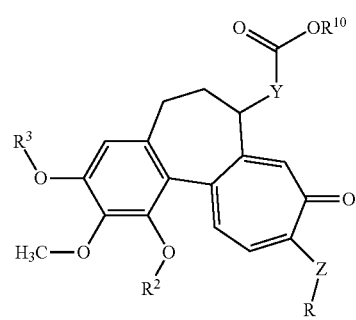

Formula X wherein:
Z is O or S;
Y is NH or $CH_2$;
$R^{13}$ is selected from H, a substituted or unsubstituted hydrocarbon group, or a substituted or unsubstituted heterogeneous group;
$R^2$ and $R^3$ are each independently selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;
R is selected from H or a substituted or unsubstituted hydrocarbon group;
and/or a pharmaceutically-acceptable salt, hydrate, solvate, tautomer, optical isomer, or combination thereof.

In another aspect, the compound is a compound of Formula XA and/or XB:

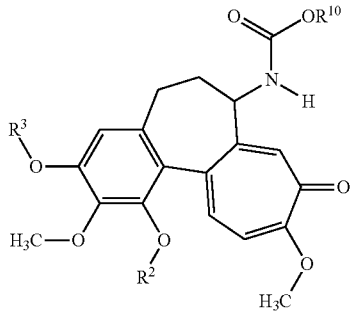

Formula XA

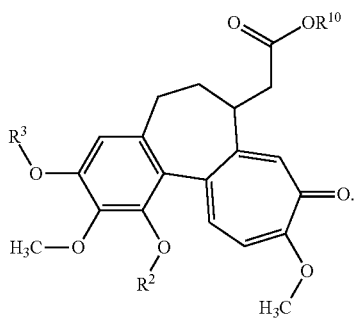

Formula XB

In another aspect, the compound is a compound of Formula XC and/or XD:

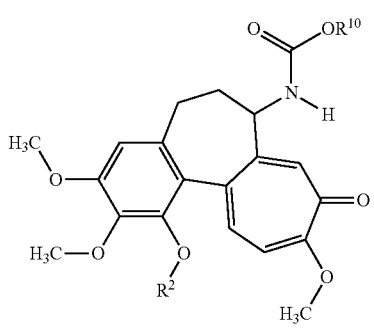

Formula XC

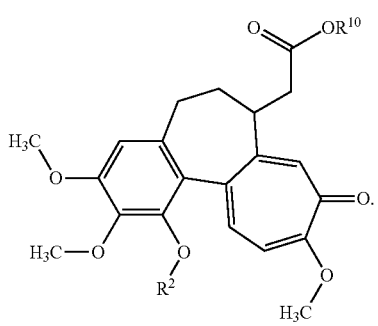

Formula XD

In another aspect, the compound is a compound of Formula XE and/or XF:

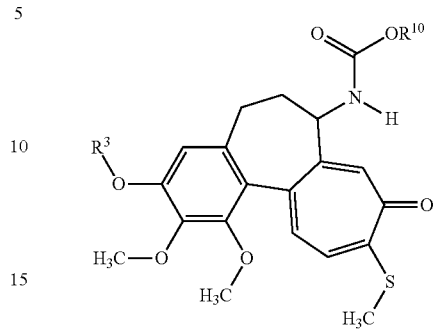

Formula XE

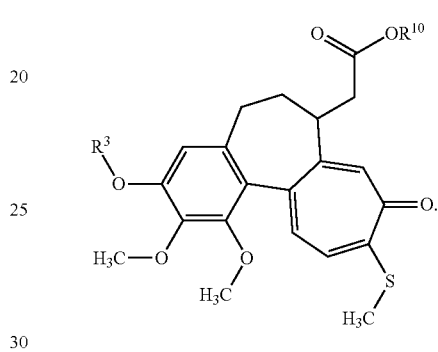

Formula XF

In another aspect, there is provided a method for treating a cancer in a mammal, comprising administering to the mammal a therapeutically effective amount of at least one of the compounds outlined above.

In a further aspect, there is provided use of at least one of the compounds outlined above for the manufacture of a medicament for treatment of a cancer in a mammal.

In another aspect, there is provided use of a composition comprising at least one of the compounds outlined above for the manufacture of a medicament for treatment of a cancer in a mammal.

In yet a further aspect, there is provided at least one of the compounds outlined above to treat a cancer in a mammal.

In another aspect, there is provided use of a composition comprising at least one of the compounds outlined above to treat a cancer in a mammal.

In a further aspect, there is provided use of 3-D cultured cells for MRI to determine the effect of a therapeutic compound or composition on the cells.

In still a further aspect, there is provided a method for determining an effect of a therapeutic compound or composition on cultured cells comprising:

growing 3-D cultured cells;

introducing the therapeutic compound or composition; and monitoring the effect of the therapeutic compound or composition on the cells using MRI.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described, by way of example only, with reference to the attached Figures.

FIG. 3 shows a synthetic scheme for making compounds (6) to (38);

FIGS. 4A to 4H show examples of second and third generation colchicines and thiocolchicine derivatives;

FIG. 13A shows residues contained within the binding surface for colchicine [pdb code 1SA0] are shown as black letters on the canonical β1-tubulin sequence and differences between the three types of binding sites are shown as medium gray letters, the remaining letters are gray, and dashes represent identical positions between the sequences, FIG. 13B shows a solvent accessible surface drawn onto β-tubulin [pdb code 1SA0] and the residues making up the colchicine binding surface are shown in black on the cartoon, while residues exhibiting differences between the three binding site models are shown as black sticks, and colchicine is shown as a molecular structure, with the A-ring and the X and Y positions clearly visible;

FIG. 15A shows log $IC_{50}$ of each cell line as clustered by colchicine derivative and each point corresponds to a colchicine derivative for each of the six cell lines investigated; FIG. 15B shows log $IC_{50}$ grouped by drug functional group and each point represents a colchicine derivative and the log $IC_{50}$ are calculated as means over the A549, HeLa, MCF-7 and CEM cell lines; FIG. 15C shows $I_{bot}$ grouped by cell line and each point is a drug/cell line pair. All drugs except, (3) and D14 (for which limited or no cytotoxicity data was available) were included in this calculation.

FIG. 16A shows $k_{on}[M^{-1} s^{-1}]$ values for the binding of colchicine and all colchicine derivatives (except for (5) and D14) to tubulin αβII and ββIII from the binding kinetics experiments; values for αβII are shown on the x-axis, for αβIII on the y-axis; selected drugs are labeled, and the line is a fit of the data with $R^2=0.95$; and FIG. 16B shows log $IC_{50}$ [log 10 M] values for cytotoxicity of colchicine and selected colchicine derivatives averaged over the cell lines A549, HeLa, MCF-7 and CEM, versus log $K_D$ [log 10 M] for binding of same drugs to tubulin αβIII calculated from the $k_{on}$ values assuming that $k_{off}=2.5\times10^{-4}$ s$^{-1}$ (Banerjee A. et al., J. Biol Chem. 1992; 267:13335-9); and the line is a fit of the data with $R^2=0.30$.

DETAILED DESCRIPTION

Figure 1:
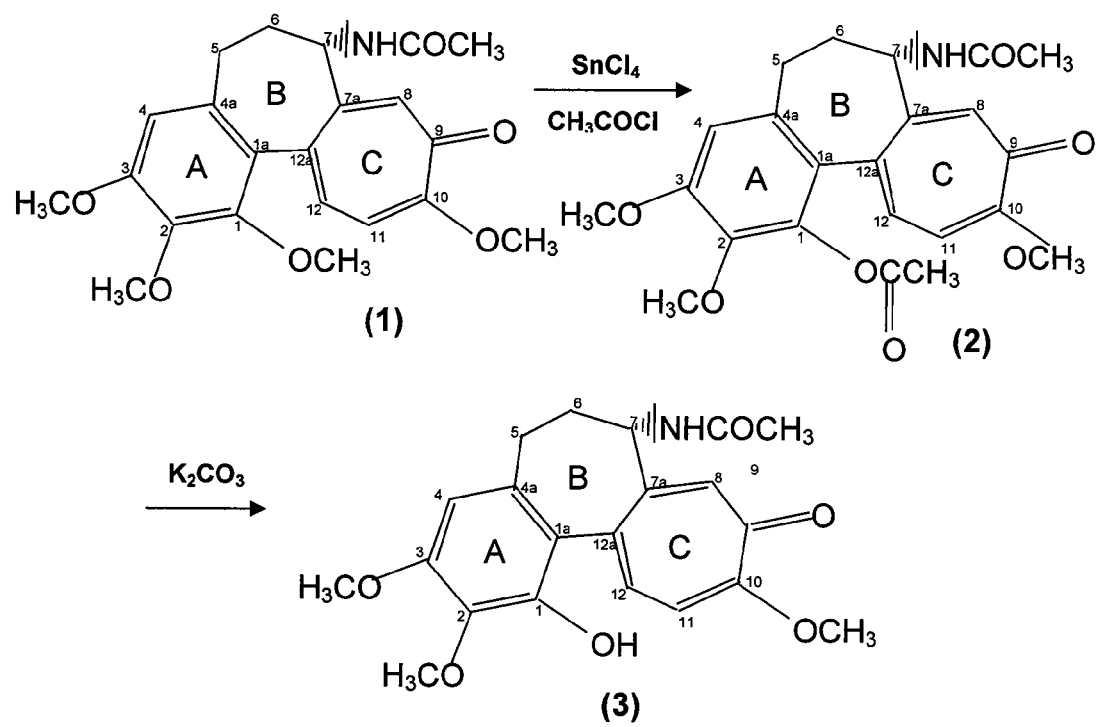
FIG. 1 shows a synthetic scheme for making compounds (2) and (3)

The present invention is directed to a colchicine derivative, a composition comprising the derivative, a method of administration thereof, and use thereof, in particular, for treatment of cancer. In addition, the invention is directed to screening techniques.

Definitions

When describing the compounds, compositions, methods and uses of this invention, the following terms have the following meanings unless otherwise indicated.

The term "colchicines derivatives" as used herein may include any of the derivatives described herein, for example, it may also include thiocolchicine derivatives, where appropriate.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the present invention may have asymmetric centers, chiral axes, and chiral planes (as described, for example, in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, Spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N,N-dimethyl-aminoethyl, N,N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

The terms "comprising", "having" and "including", and various endings thereof, are meant to be open ended, including the indicated component but not excluding other elements.

First Generation Colchicine Derivatives

The first generation of colchicine derivatives of the invention are represented by a compound of Formula I:

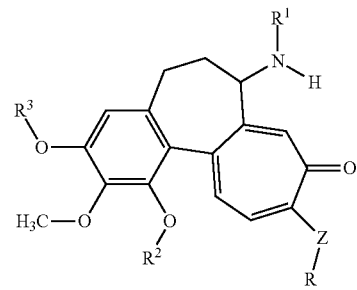

Formula I wherein: Z is O or S; $R^1$ is selected from H, a halo group, a substituted or unsubstituted hydrocarbon group, a substituted or unsubstituted heterogeneous group; $R^2$ and $R^3$ are each independently selected from H, a halo group, a substituted or unsubstituted hydrocarbon group, a substituted or unsubstituted heterogeneous group, or a substituted or unsubstituted carbocyclic group, with the proviso that when R, $R^2$ and $R^3$ are methyl groups, $R^1$ is not —$COCH_3$; and/or a pharmaceutically-acceptable salt, hydrate, solvate, tautomer, optical isomer, or combination thereof.

In specific embodiments of Formula I, $R^2$ and $R^3$ are each independently selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In more particular embodiments, $R^2$ and $R^3$ are each independently selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted $C_1$-$C_6$ alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^2$ and $R^3$ are each independently selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl.

$R^1$ can be selected from H, a substituted or unsubstituted hydrocarbon group, a substituted or unsubstituted heterogeneous group. More specifically, $R^1$ can be selected from a substituted or unsubstituted —COX and X is selected from H, a substituted or unsubstituted hydrocarbon group, a substituted or unsubstituted heterogeneous group. The —COX can be —COCR$^4$R$^5$R$^6$, wherein R$^4$R$^5$R$^6$ are each independently selected from H, a substituted or unsubstituted hydrocarbon group, a substituted or unsubstituted heterogeneous group. In particular, R$^4$R$^5$R$^6$ can each be independently selected from substituted or unsubstituted amido groups. In a specific embodiment $R^4$ and $R^5$ are each independently selected from H, substituted or unsubstituted alkyl group, and $R^6$ is —NR(CO)CR$^7$R$^8$R$^9$, wherein $R^7$, $R^8$, and $R^9$ are each selected from H, halo group, a substituted or unsubstituted alkyl group. $R^7$, $R^8$, and $R^9$ can be selected from a halo group. More specifically, $R^7$, $R^8$, and $R^9$ can be selected from a fluoro group.

R can be selected from a substituted or unsubstituted hydrocarbon group. Specifically, R can be selected from a substituted or unsubstituted $C_1$-$C_6$ alkyl.

In certain embodiments, the colchicine derivative comprises a compound of Formula IA:

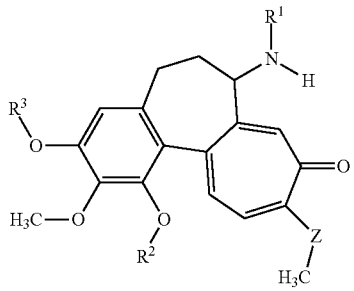

Formula IA wherein: Z is O or S; $R^1$ is selected from H, a halo group, a substituted or unsubstituted hydrocarbon group, a substituted or unsubstituted heterogeneous group; $R^2$ and $R^3$ are each independently selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic, with the proviso that when $R^2$ and $R^3$ are methyl groups, $R^1$ is not —COCH$_3$; and/or a pharmaceutically-acceptable salt, hydrate, solvate, tautomer, optical isomer, or combination thereof.

In specific embodiments of Formula IA, $R^2$ and $R^3$ are each independently selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In more particular embodiments, $R^2$ and $R^3$ are each independently selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^2$ and $R^3$ are each independently selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In more specific embodiments, $R^2$ and $R^3$ are each independently selected from a substituted or unsubstituted $C_1$-$C_6$ alkyl, a substituted or unsubstituted $C_2$-$C_6$ alkenyl, or $C_1$-$C_6$ alkylene-O-alkyl.

$R^1$ can be selected from H, a substituted or unsubstituted hydrocarbon group, a substituted or unsubstituted heterogeneous group. More specifically, $R^1$ can be selected from a substituted or unsubstituted —COX and X is selected from H, a substituted or unsubstituted hydrocarbon group, a substituted or unsubstituted heterogeneous group. The —COX group can be —COCR$^4$R$^5$R$^6$, wherein R$^4$R$^5$R$^6$ are each independently selected from H, a substituted or unsubstituted hydrocarbon group, a substituted or unsubstituted heterogeneous group. In particular, R$^4$R$^5$R$^6$ can each be independently selected from substituted or unsubstituted amido groups. In a specific embodiment $R^4$ and $R^5$ are each independently selected from H, substituted or unsubstituted alkyl group, and $R^6$ is —NR(CO)CR$^7$R$^8$R$^9$, wherein $R^7$, $R^8$, and $R^9$ are each selected from H, halo group, a substituted or unsubstituted alkyl group. $R^7$, $R^8$, and $R^9$ can be selected from a halo group. More specifically, $R^7$, $R^8$, and $R^9$ can be selected from a fluoro group.

In certain embodiments, the colchicine derivative comprises a compound of Formula II:

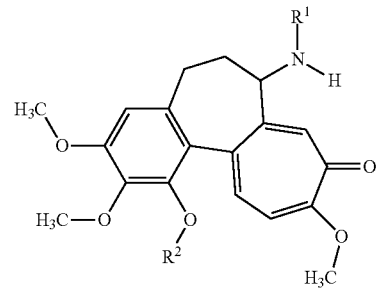

Formula II wherein: $R^1$ is selected from H, a halo group, a substituted or unsubstituted hydrocarbon group, a substituted or unsubstituted heterogeneous group; $R^2$ is selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic, with the proviso that when $R^2$ is a methyl group, $R^1$ is not —$COCH_3$; and/or a pharmaceutically-acceptable salt, hydrate, solvate, tautomer, optical isomer, or combination thereof.

In specific embodiments of Formula II, $R^2$ is selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In more particular embodiments, $R^2$ is selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^2$ and $R^3$ are each independently selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In more specific embodiments, $R^2$ and $R^3$ are each independently selected from a substituted or unsubstituted $C_1$-$C_6$ alkyl, a substituted or unsubstituted $C_2$-$C_6$ alkenyl, or $C_1$-$C_6$ alkylene-O-alkyl.

$R^1$ can be selected from H, a substituted or unsubstituted hydrocarbon group, a substituted or unsubstituted heterogeneous group. More specifically, $R^1$ can be selected from a substituted or unsubstituted —COX and X is selected from H, a substituted or unsubstituted hydrocarbon group, a substituted or unsubstituted heterogeneous group. The —COX can be —$COCR^4R^5R^6$, wherein $R^4R^5R^6$ are each independently selected from H, a substituted or unsubstituted hydrocarbon group, a substituted or unsubstituted heterogeneous group. In particular, $R^4R^5R^6$ can each be independently selected from substituted or unsubstituted amido groups. In a specific embodiment $R^4$ and $R^5$ are each independently selected from H, substituted or unsubstituted alkyl group, and $R^6$ is —$NR(CO)CR^7R^8R^9$, wherein $R^7$, $R^8$, and $R^9$ are each selected from H, halo group, a substituted or unsubstituted alkyl group. $R^7$, $R^8$, and $R^9$ can be selected from a halo group. More specifically, $R^7$, $R^8$, and $R^9$ can be selected from a fluoro group.

In certain embodiments, the colchicine derivative comprises a compound of Formula IIA:

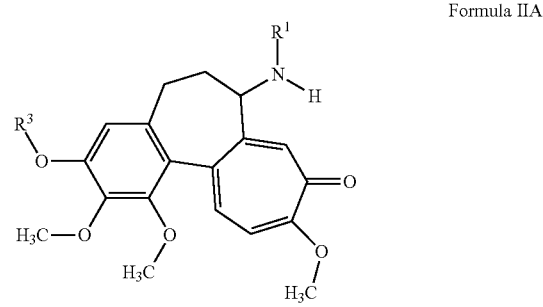

Formula IIA wherein: $R^1$ is selected from H, a halo group, a substituted or unsubstituted hydrocarbon group, a substituted or unsubstituted heterogeneous group; $R^3$ is selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic, with the proviso that when $R^3$ is a methyl group, $R^1$ is not —$COCH_3$; and/or a pharmaceutically-acceptable salt, hydrate, solvate, tautomer, optical isomer, or combination thereof.

In specific embodiments of Formula II, $R^3$ is selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In more particular embodiments, $R^3$ is selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^3$ is selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In more specific embodiments, $R^3$ is selected from a substituted or unsubstituted $C_1$-$C_6$ alkyl, a substituted or unsubstituted $C_2$-$C_6$ alkenyl, or $C_1$-$C_6$ alkylene-O-alkyl.

$R^1$ can be selected from H, a substituted or unsubstituted hydrocarbon group, a substituted or unsubstituted heterogeneous group. More specifically, $R^1$ can be selected from a substituted or unsubstituted —COX and X is selected from H, a substituted or unsubstituted hydrocarbon group, a substituted or unsubstituted heterogeneous group. The —COX can be —COCR⁴R⁵R⁶, wherein R⁴R⁵R⁶ are each independently selected from H, a substituted or unsubstituted hydrocarbon group, a substituted or unsubstituted heterogeneous group. In particular, $R^4R^5R^6$ can each be independently selected from substituted or unsubstituted amido groups. In a specific embodiment $R^4$ and $R^5$ are each independently selected from H, substituted or unsubstituted alkyl group, and $R^6$ is —NR(CO)CR⁷R⁸R⁹, wherein $R^7$, $R^8$, and $R^9$ are each selected from H, halo group, a substituted or unsubstituted alkyl group. $R^7$, $R^8$, and $R^9$ can be selected from a halo group. More specifically, $R^7$, $R^8$, and $R^9$ can be selected from a fluoro group.

In other embodiments, the colchicine derivative comprises a compound of Formula III:

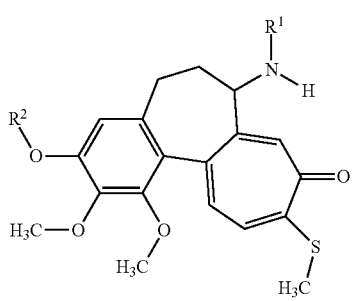

Formula III wherein: $R^1$ is selected from H, a halo group, a substituted or unsubstituted hydrocarbon group, a substituted or unsubstituted heterogeneous group; $R^2$ is selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic, with the proviso that when $R^2$ is a methyl group, $R^1$ is not —COCH₃; and/or a pharmaceutically-acceptable salt, hydrate, solvate, tautomer, optical isomer, or combination thereof.

In specific embodiments of Formula III, $R^2$ is selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In more particular embodiments, $R^2$ is selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^2$ is selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In more specific embodiments, $R^2$ is selected from a substituted or unsubstituted $C_1$-$C_6$ alkyl, a substituted or unsubstituted $C_2$-$C_6$ alkenyl, or $C_1$-$C_6$ alkylene-O-alkyl.

$R^1$ can be selected from H, a substituted or unsubstituted hydrocarbon group, a substituted or unsubstituted heterogeneous group. More specifically, $R^1$ can be selected from a substituted or unsubstituted —COX and X is selected from H, a substituted or unsubstituted hydrocarbon group, a substituted or unsubstituted heterogeneous group. The —COX can be —COCR⁴R⁵R⁶, wherein R⁴R⁵R⁶ are each independently selected from H, a substituted or unsubstituted hydrocarbon group, a substituted or unsubstituted heterogeneous group. In particular, $R^4R^5R^6$ can each be independently selected from substituted or unsubstituted amido groups. In a specific embodiment $R^4$ and $R^5$ are each independently selected from H, substituted or unsubstituted alkyl group, and $R^6$ is —NR(CO)CR⁷R⁸R⁹, wherein $R^7$, $R^8$, and $R^9$ are each selected from H, halo group, a substituted or unsubstituted alkyl group. $R^7$, $R^8$, and $R^9$ can be selected from a halo group. More specifically, $R^7$, $R^8$, and $R^9$ can be selected from a fluoro group.

The colchicine derivatives described herein can be a pharmaceutically-acceptable salt thereof, a hydrate thereof, a solvate thereof, a tautomer thereof, an optical isomer thereof, or a combination thereof. In more specific embodiments, the compounds of Formulae I to III have the S-configuration at C7, for example, see FIGS. 3 to 4.

Examples of the compounds of Formula I are (3) to (54), as shown in FIGS. 1 to 4. Such compounds may be used as is and/or in the form of a pharmaceutically-acceptable salt, hydrate, solvate or any combination thereof.

Certain compounds described herein can be prepared, for example, as follows:

a) reacting a compound of Formula IV with ROCl:

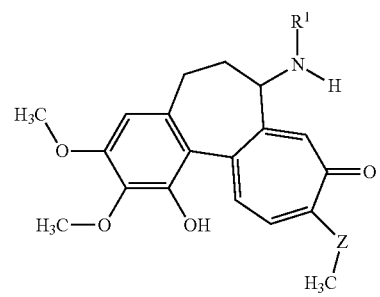

Formula IV to form:

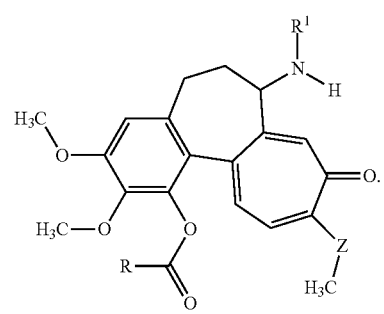

Formula V

Wherein: R and $R^1$ can be as defined above.

Certain compounds described herein can also be prepared as follows:

a) reacting a compound of Formula IV with R²Br:

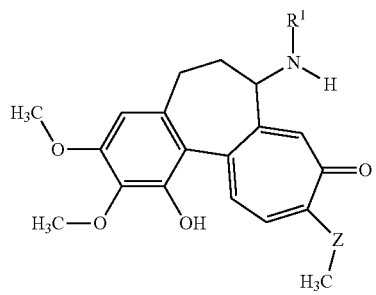
Formula IV to form:

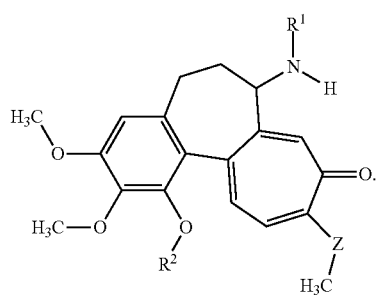
Formula VI

Wherein: R¹ and R² can be as defined above.

Certain compounds described herein can also be prepared as follows:

a) reacting a compound of Formula VII with R²Br:

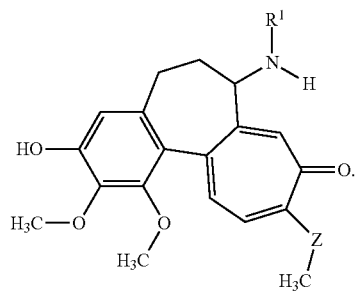
Formula VII to form:

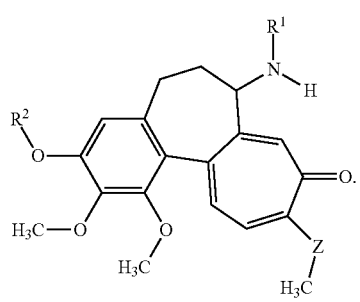
Formula VIII

Wherein: R¹ and R² can be as defined above.

More specific R¹ groups can be added by, for example, reacting Formula VI or VIII, wherein R¹ is —(CO)OR with HO(CO)CR⁴R⁵R⁶, wherein R⁴R⁵R⁶ are each independently selected from H, a substituted or unsubstituted hydrocarbon group, a substituted or unsubstituted heterogeneous group. In particular, R⁴R⁵R⁶ can each be independently selected from substituted or unsubstituted amido groups. In a specific embodiment R⁴ and R⁵ are each independently selected from H, substituted or unsubstituted alkyl group, and R⁶ is —NR(CO)CR⁷R⁸R⁹, wherein R⁷, R⁸, and R⁹ are each selected from H, halo group, a substituted or unsubstituted alkyl group. R⁷, R⁸, and R⁹ can be selected from a halo group. More specifically, R⁷, R⁸, and R⁹ can be selected from a fluoro group.

Certain compounds described herein can also be prepared, for example, as follows:

a) reacting a compound of Formula VIA with 1-ethyl-3-(3-dimethylaminopropyl)carbodiimide (EDCl), hydroxybenzotriazole (HOBt) and CF₃NHCH₂COOH (F₃CglyOH)

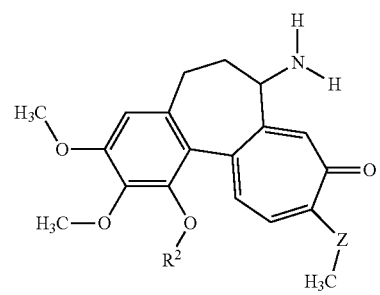
Formula VIA to form:

Formula VIB

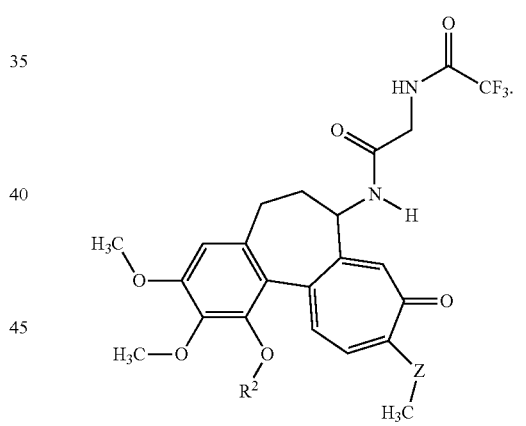

Wherein: R² can be as defined above.

Certain compounds described herein can also be prepared as follows:

a) protecting the hydroxyl group of a compound of Formula VIIA

Formula VIIA

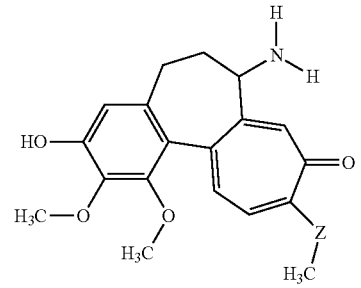

to form (PG=protecting group):

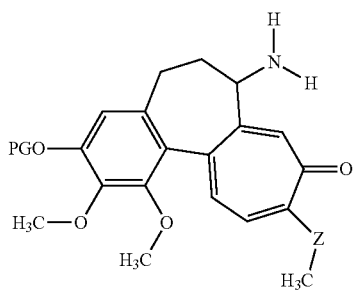

Formula VIIB b) reacting a compound of Formula VIIB with 1-ethyl-3-(3-dimethylaminopropyl) carbodiimide (EDCl), hydroxybenzotriazole (HOBt) and CF$_3$NHCH$_2$COOH (F$_3$CglyOH), followed by deprotection to form:

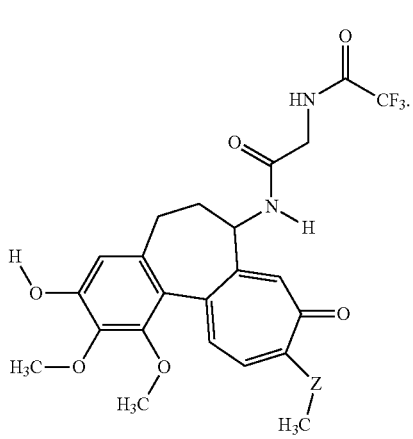

Formula VIIC

Second Generation Colchicine Derivatives

The second generation of colchicine derivatives of the invention are represented by a compound of Formula IB:

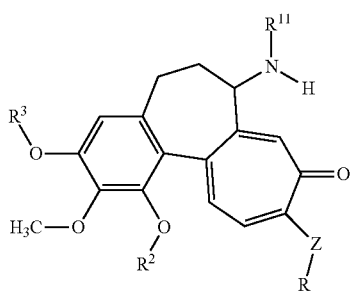

Formula IB wherein: Z is O or S; $R^{11}$ is selected from H, a substituted or unsubstituted alkoxy, a substituted or unsubstituted alkyl, a substituted or unsubstituted alkenyl, a substituted or unsubstituted alkynyl, a substituted or unsubstituted alkylcarbonyl, or a —(C=O)H; $R^2$ and $R^3$ are each independently selected from H, a halo group, a substituted or unsubstituted hydrocarbon group, a substituted or unsubstituted heterogeneous group, or a substituted or unsubstituted carbocyclic group; and/or a pharmaceutically-acceptable salt, hydrate, solvate, tautomer, optical isomer, or combination thereof.

In specific embodiments of Formula IB, $R^2$ and $R^3$ are each independently selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In more particular embodiments, $R^2$ and $R^3$ are each independently selected from a substituted or unsubstituted alkyl, a substituted or unsubstituted haloalkyl, a substituted or unsubstituted hydroxyalkyl, a substituted or unsubstituted cyanoalkyl, a substituted or unsubstituted alkenyl, a substituted or unsubstituted $C_1$-$C_6$ alkylcarbonyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkyl heterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. In other embodiments, $R^2$ and $R^3$ are each independently selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl.

$R^{11}$ can be selected from H, a substituted or unsubstituted alkoxy, or a —(C=O)H. More specifically, $R^{11}$ can be selected from H, a substituted or unsubstituted $C_1$-$C_6$ alkoxy, or a —(C=O)H.

R can be selected from a substituted or unsubstituted hydrocarbon group. Specifically, R can be selected from a substituted or unsubstituted $C_1$-$C_6$ alkyl.

In certain embodiments, the second colchicine derivative comprises a compound of Formula IC:

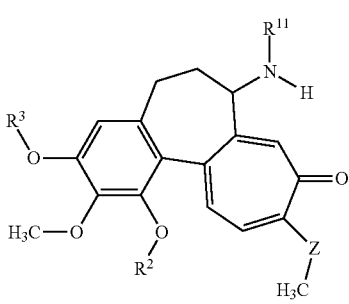

Formula IC wherein: Z, $R^{11}$, $R^2$, and $R^3$ are as outlined above with respect to Formula IB.

In certain embodiments, the second generation colchicine derivative comprises a compound of Formula ID:

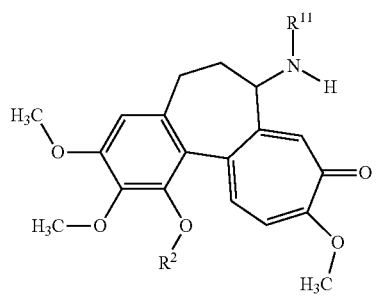

Formula ID wherein: $R^{11}$ and $R^2$ are as outlined above with respect to Formula IB.

In certain embodiments, the second generation colchicine derivative comprises a compound of Formula IE:

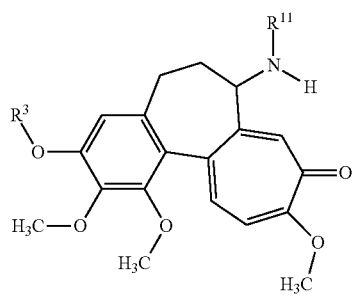

Formula IE wherein: $R^{11}$ and $R^3$ are as outlined above with respect to Formula IB.

In other embodiments, the second generation colchicine derivative comprises a compound of Formula IF:

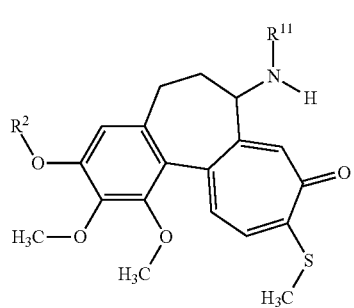

Formula IF wherein: $R^{11}$ and $R^2$ are as outlined above with respect to Formula IB.

The colchicine derivatives described herein can be a pharmaceutically-acceptable salt thereof, a hydrate thereof, a solvate thereof, a tautomer thereof, an optical isomer thereof, or a combination thereof. In more specific embodiments, the compounds of Formulae IB to IF have the S-configuration at C7, for example, see FIGS. 4A to 4B.

Figure 4:
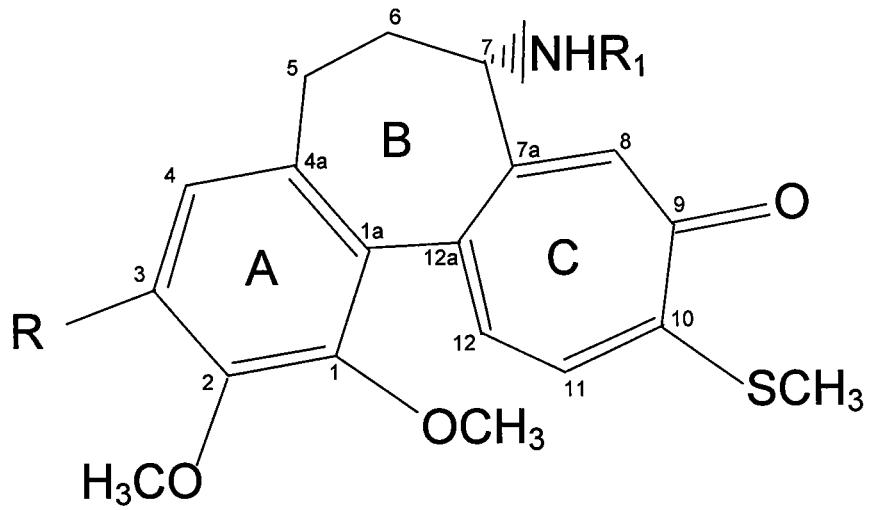
FIG. 4 shows the structure of thiocolchicine with modifications (39), (3 a-c), (4 a-c) and (5 a-c) to thiocolchicine at the R and $R_1$ positions.
Figure 4B:
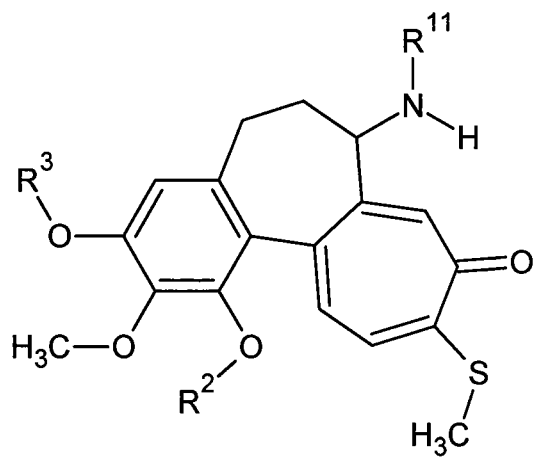

Examples of the compounds of Formula IB are (55) to (75), as shown in FIGS. 4A to 4B. Such compounds may be used as is and/or in the form of a pharmaceutically-acceptable salt, hydrate, solvate or any combination thereof.

Other second generation colchicine derivatives of the invention are represented by a compound of Formula IX:

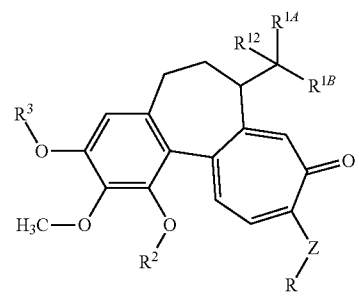

Formula IX wherein: Z is O or S; $R^{1A}$, and $R^{1B}$ are each independently selected from H, or a substituted or unsubstituted hydrocarbon group; $R^{12}$ is selected from H, a substituted or unsubstituted alkoxy, a substituted or unsubstituted alkyl, a substituted or unsubstituted alkenyl, or a substituted or unsubstituted alkynyl; $R^2$ and $R^3$ are each independently selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; R is selected from H or a substituted or unsubstituted hydrocarbon group; and/or a pharmaceutically-acceptable salt, hydrate, solvate, tautomer, optical isomer, or combination thereof.

In specific embodiments of Formula IX, Z, R, $R^2$ and $R^3$ can be as noted above with respect to Formula IB. $R^{1A}$ and $R^{1B}$ can be each independently selected from H or a substituted or unsubstituted alkyl group. $R^{12}$ can be selected from a substituted or unsubstituted alkoxy, or a substituted or unsubstituted alkyl. Even more specifically, $R^{12}$ can be selected from a substituted or unsubstituted $C_1$-$C_6$ alkoxy group, or a substituted or unsubstituted $C_1$-$C_6$ alkyl group. In specific embodiments, $R^{12}$ is selected from a substituted or unsubstituted $C_1$-$C_6$ alkoxy group.

In certain embodiments, the second generation colchicine derivative comprises compound of Formula IXA:

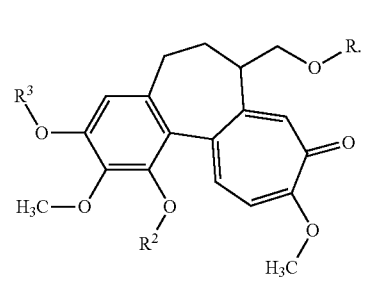

Formula IXA

For Formula IXA, R, $R^2$ and $R^3$ can be as noted above with respect to Formula IX.

In certain embodiments, the second generation colchicine derivative comprises compound of Formula IXB:

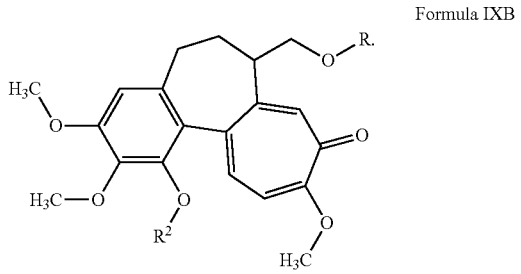

Formula IXB

For Formula IXB, R and $R^2$ can be as noted above with respect to Formula IX.

In certain embodiments, the second generation colchicine derivative comprises compound of Formula IXC:

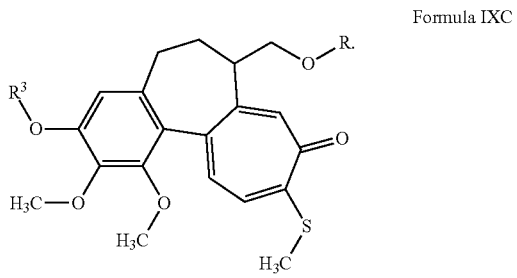

Formula IXC

For Formula XC, R and $R^3$ can be as noted above with respect to Formula X.

The other second generation colchicine derivatives described herein can be a pharmaceutically-acceptable salt thereof, a hydrate thereof, a solvate thereof, a tautomer thereof, an optical isomer thereof, or a combination thereof. In more specific embodiments, the compounds of Formulae IX to IXC have the S-configuration at C7.

Figure 4C:
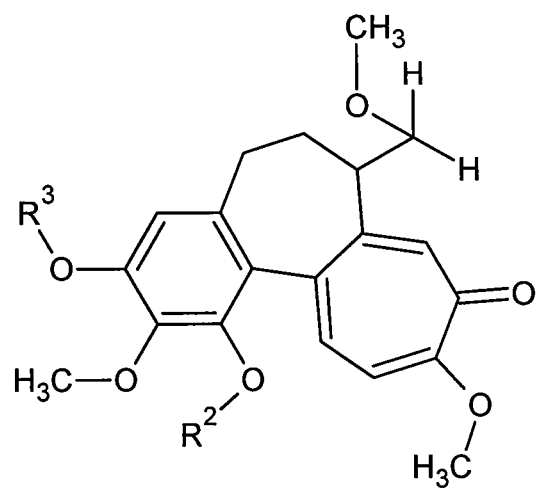
Figure 4D:
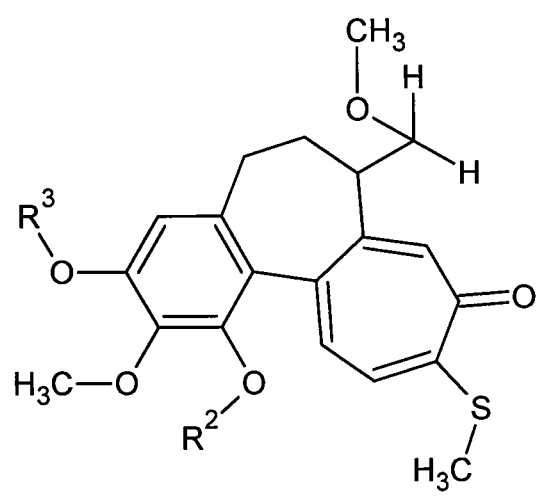
Figure 4E:
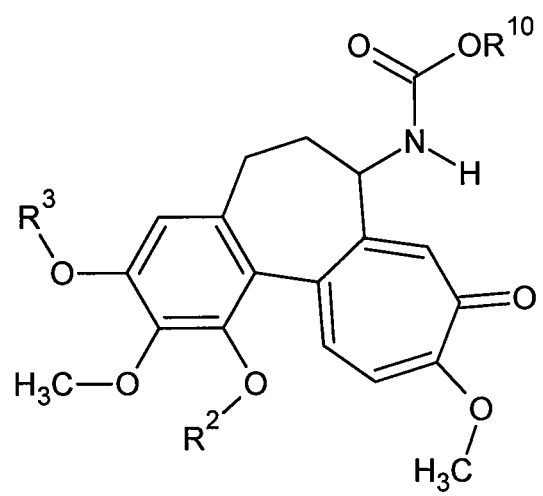
Figure 4F:
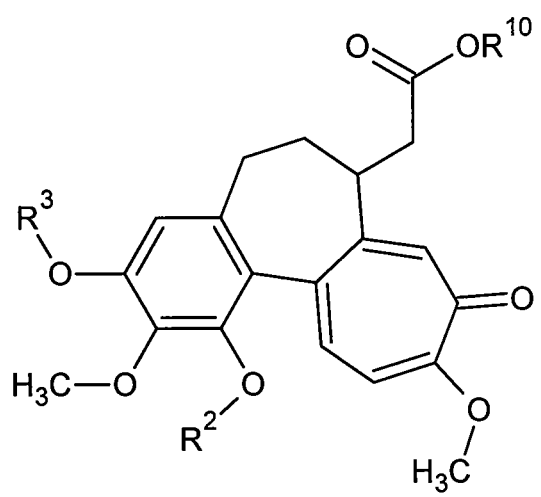
Figure 4G:
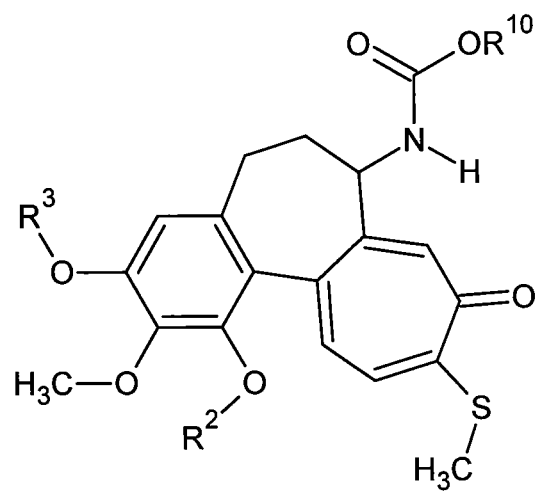
Figure 4H:
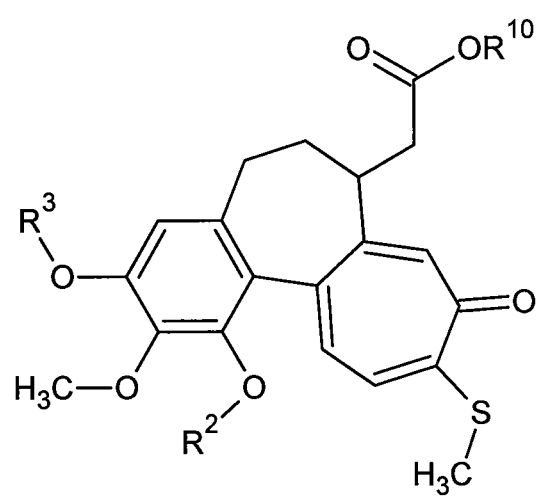

Examples of the compounds of Formula IX are (76) to (82), as shown in FIGS. 4C to 4D. Such compounds may be used as is and/or in the form of a pharmaceutically-acceptable salt, hydrate, solvate or any combination thereof.

Third Generation Colchicine Derivatives

The third generation of colchicine derivatives of the invention are represented by a compound of Formula X:

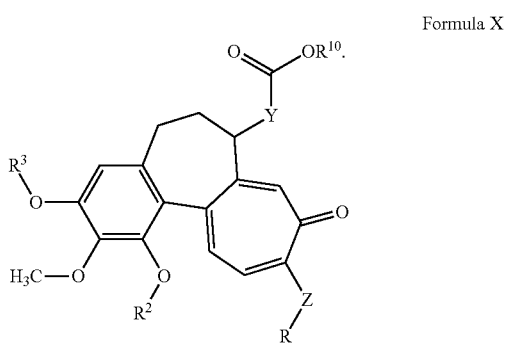

Formula X wherein: Z is O or S; Y is NH or $CH_2$; $R^{10}$ is selected from H, a substituted or unsubstituted hydrocarbon group, or a substituted or unsubstituted heterogeneous group; $R^2$ and $R^3$ are each independently selected from H, a halo group, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic, or a substituted or unsubstituted heteroaromatic; R is selected from H or a substituted or unsubstituted hydrocarbon group; and/or a pharmaceutically-acceptable salt, hydrate, solvate, tautomer, optical isomer, or combination thereof.

In specific embodiments of Formula X, R, $R^2$ and $R^3$ can be as noted above with respect to Formula I.

$R^{10}$ can be selected from a substituted or unsubstituted hydrocarbon group, or a substituted or unsubstituted heterogeneous group. More specifically, $R^{10}$ can be selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group. In particular, $R^{10}$ can be selected from a substituted or unsubstituted alkyl, $CH_2OH$, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkylene-heterocycloalkyl. Even more specifically, $R^{10}$ can be selected from a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl. In specific embodiments, $R^{10}$ can be selected from a substituted or unsubstituted $C_1$-$C_6$ alkyl, or a substituted or unsubstituted $C_2$-$C_6$ alkenyl, or $C_1$-$C_6$ alkynyl. In particular embodiments, $R^{10}$ is selected from a substituted or unsubstituted $C_1$-$C_6$ alkyl.

In certain embodiments, the third generation colchicine derivative comprises a compound of Formula XA and/or XB:

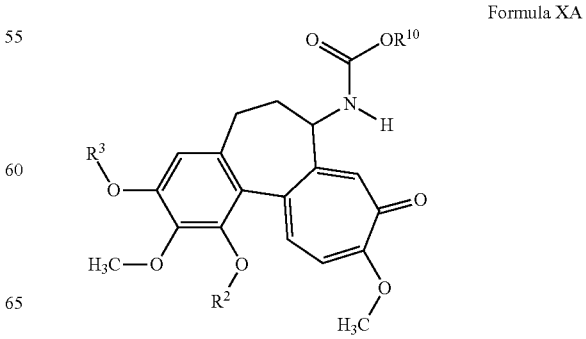

Formula XA

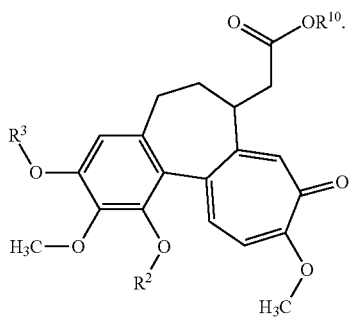

Formula XB

For Formulae XA and XB, R, $R^2$, $R^3$ and $R^{10}$ can be as noted above with respect to Formula X.

In other embodiments, the third generation colchicine derivative comprises a compound of Formula XC and/or XD:

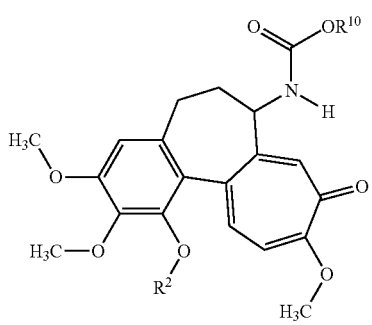

Formula XC

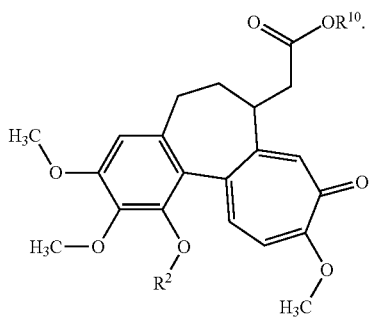

Formula XD

For Formulae XC and XD, $R^3$ and $R^{10}$ can be as noted above with respect to Formula X.

In other embodiments, the third generation colchicine derivative comprises a compound of Formula XE and/or XF:

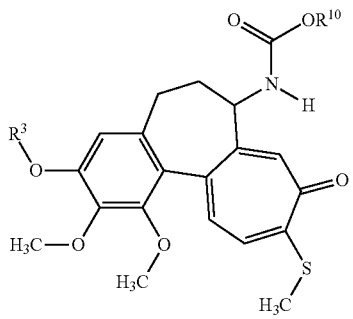

Formula XE

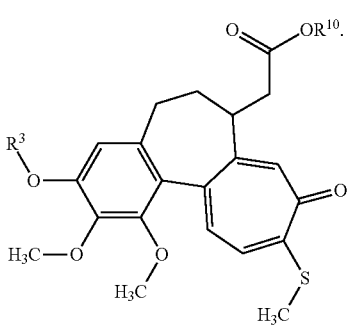

Formula XF

For Formulae XE and XF, $R^3$ and $R^{10}$ can be as noted above with respect to Formula X.

The third generation colchicine derivatives described herein can be a pharmaceutically-acceptable salt thereof, a hydrate thereof, a solvate thereof, a tautomer thereof, an optical isomer thereof, or a combination thereof. In more specific embodiments, the compounds of Formulae X to XF have the S-configuration at C7.

Examples of the compounds of Formula X are (83) to (94), as shown in FIGS. 4E to 4H. Such compounds may be used as is and/or in the form of a pharmaceutically-acceptable salt, hydrate, solvate or any combination thereof.

Certain compounds described herein can be prepared, for example, as follows:

a) reacting a compound of Formula XX with RO(C═O)Cl:

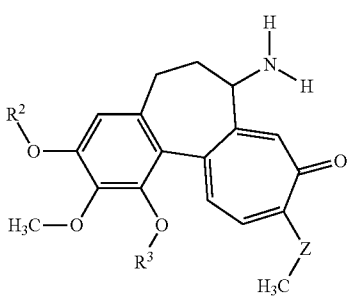

Formula XX to form:

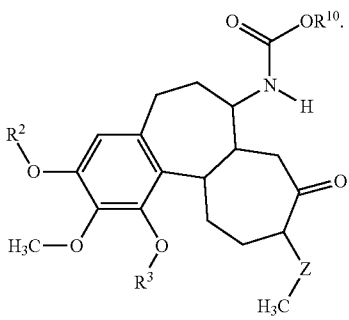

Formula XXI

Wherein: $R^2$ and $R^3$ can be as defined above.

Certain compounds described herein can also be prepared as follows:

a) protecting the hydroxyl group of a compound of Formula XXII

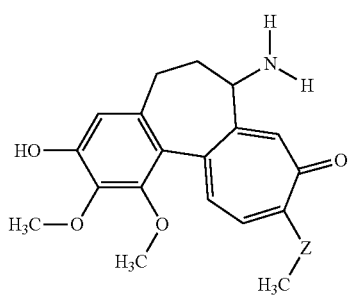

Formula XXII to form (PG=protecting group):

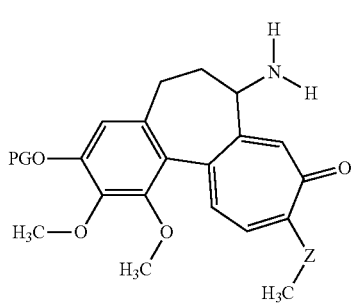

Formula XXIIB b) reacting a compound of Formula XXIIB with RO(C=O)Cl, followed by deprotection to form:

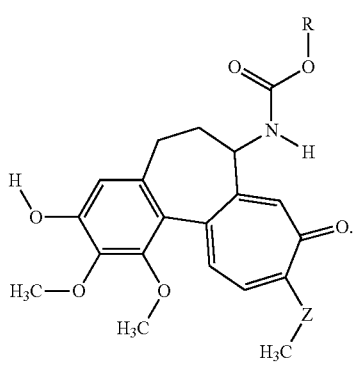

Formula XXIIC

In general, the compounds of this invention may be prepared by employing reactions and standard manipulations that are known in the literature or exemplified herein.

The compounds of the present invention are useful in the treatment of cancer. The cancer treated may be, for example, lung cancer, cervical cancer, ovarian cancer, cancer of CNS, skin cancer, prostate cancer, sarcoma, breast cancer, leukemia, colorectal cancer, head cancer, neck cancer or kidney cancer. More typically, the cancer may be breast cancer, acute leukemia, chronic leukemia, colorectal cancer, or brain cancer. The cancer may be a carcinoma. The carcinoma may be selected from small cell carcinomas, cervical carcinomas, glioma, astrocytoma, prostate carcinomas, ovarian carcinomas, melanoma, breast carcinomas, or colorectal carcinomas. Compounds of the present invention may be even more particularly useful in the treatment of lung carcinoma, cervical carcinoma, adenocarcinoma, glioma, promyelocytic leukemia, T-cell leukemia, neuroblastoma, lymphoma, pancreatic cancer and ALL.

In specific embodiments, the thiocolchicine derivatives are used to treat breast cancer. Functionalization of the amino group at position C7 with polar substituents, such as amino esters, modifies the growth inhibitory activity of the cell lines. The introduction of a trifluoromethyl group in side chain of ring B increases the drug activity in thiocolchicine.

Compounds of the present invention can have an $IC_{50}$ for a cancer cell population of less than about 40 nM. In specific embodiments, compounds of the present invention show efficacy against cancer cells at $IC_{50}$'s of less than about 20 nM, typically less than about 15 nM, more typically less than about 10 nM.

Compounds described herein show efficacy against, for example, cell lines of A549 (Human lung carcinoma), HeLa (Human cervical carcinoma), MCF-7 (Human mammary gland adenocarcinoma), CEM (Human T-lymphoblastoid from ALL (Acute lymphoblastic leukemia)), M010B (Human glioma) and M006X (Human glioma).

Certain compounds of the present invention may exhibit reduced toxicity as compared with conventionally administered agents.

The compounds of this invention may be administered to mammals, typically humans, either alone or, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, and subcutaneous routes of administration.

As noted, compounds of the present invention may be administered orally. For oral use of a compound or composition according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compound/composition can be administered orally. However, other methods of administration may also be used.

The compounds of the present invention may also be combined and/or co-administered with other therapeutic agents that are selected for their particular usefulness against the cancer that is being treated. For example, the compounds of the present invention may be combined and/or co-administered with anti-cancer agent(s).

Examples of anti-cancer agents include, without being limited thereto, the following: estrogen receptor modulators, androgen receptor modulators, retinoid receptor modulators, cytotoxic agents, antiproliferative agents, tyrosine kinase inhibitors, prenyl-protein transferase inhibitors, HMG-CoA reductase inhibitors, HIV protease inhibitors, reverse transcriptase inhibitors, other angiogenesis inhibitors and combinations thereof. The present compounds may also be useful with other therapies such as when co-administered with radiation therapy.

"Estrogen receptor modulators" refers to compounds which interfere or inhibit the binding of estrogen to the receptor, regardless of mechanism. Examples of estrogen receptor modulators include, but are not limited thereto, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited thereto, cyclophosphamide ifosfamide, hexamethylmelamine, tirapazimine, sertenef, cachectin, ifosfamide, tasonermin, lonidamine, carboplatin, mitomycin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)-platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunor-ubicin (see International Patent Application No. WO 00/50032).

Examples of microtubule inhibitors include paclitaxel (Taxol®), vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, iminotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H benzo[de]pyrano[3',4':b,7] indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazo-le-1-carboxamide, asulacrine, (5a,5aB,8aa,9b)-9-[2-[N-[2-(dimethylamino)-ethyl]-N-methylamino]ethyl]-5-[4-Hydroxy-3,5-dimethoxyphenyl]-5,5a,6,8,8a,-9-hexahydrofuro(3',4':6,7)naphtho(2,3-d)-1,3-dioxol-6-one, 2,3-(methylenedioxy)-5-methyl-7-hydroxy-8-methoxy-benzo[c]-phenanthridiniu-m, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acrid-ine-4-carboxamide, 6-[[2-(dimethylamino)ethyl]amino]-3-hydroxy-7H-indeno[2-,1-c]quinolin-7-one, and dimesna.

"Antiproliferative agents" includes BCNU, antisense RNA and DNA oligonucleotides such as G3139, ODN698, RVASKRAS, GEM231, and INX3001, and antimetabolites such as floxuridine, enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, Z-fluoromethylene-2'-deoxycytidine, N-[5-(2,3-dihydro-benzofuryl)sulfonyl]-N'-(3,4-dichloro-phenyl)urea, N6-[4-deoxy-4-[N2-[2(E),4(E)-tetradecadienoyl]glycylamino]-L-glycer-o-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4] thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone.

"Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino-)-7-methoxy-6-[3-(4-morpholinyl)propoxyl]-quinazoline, N-(3-ethynylphenyl)-6,7-bis(2-methoxyethoxy)-4-quinazolinamine, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i] [1,6]benzodiazocin-1-one, SH1382, genistein, 4-(3-chlorophenylamino)-5,6-dimethyl-7H-pyrrolo[2,3-d] pyrimidinemethane sulfonate, 4-(3-bromo-4-hydroxyphenyl)-amino-6,7-dimethoxyquinazoline, 4-(4'- hydroxyphenyl)amino-6,7-dimethoxyquinazoline, N-4-chlorophenyl-4-(4-pyridylmethyl)-1-phthalazinamine, and Tarceva® (erlotinib).

If formulated as a fixed dose, such combination products employ the compounds of this invention within the dosage range described below and the other pharmaceutically active agent(s) within its approved dosage range. Compounds of the present invention may alternatively be used sequentially with known pharmaceutically acceptable agent(s) when a combination formulation is inappropriate.

The term "administration" (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount from about 0.01 mg/kg of body weight to greater than about 100 mg/kg of body weight per day; from about 0.01 mg/kg of body weight to about 500 mg/kg of body weight per day; from about 0.01 mg/kg of body weight to about 250 mg/kg of body weight per day; or 0.01 mg/kg of body weight to about 100 mg/kg of body weight per day. These dosages can be more particularly used orally.

Although applicable to a wide variety of cancers, these methods are applicable, for example, to cancers wherein administration of cytotoxic agents is part of accepted treatment practices, for example lung cancer, cervical cancer, ovarian cancer, cancer of CNS, skin cancer, prostate cancer, sarcoma, breast cancer, leukemia, colorectal cancer, head cancer, neck cancer or kidney cancer More typically, the cancer may be breast cancer, acute leukemia, chronic leukemia, colorectal cancer, or brain cancer. The cancer may be a carcinoma. The carcinoma may be selected from small cell carcinomas, cervical carcinomas, glioma, astrocytoma, prostate carcinomas, ovarian carcinomas, melanoma, breast carcinomas, or colorectal carcinomas. Compounds of the present invention may be even more particularly useful in the treatment of lung carcinoma, cervical carcinoma, adenocarcinoma, glioma, promyelocytic leukemia, T-cell leukemia, neuroblastoma, lymphoma, pancreatic cancer and ALL.

Any combination of doses may be used. The combination may be used sequentially or simultaneously.

3-D Models

In embodiments, the invention relates to the use of 3-D cultured cells for MRI to determine the effect of a therapeutic compound or composition on the cells. The MRI utilized can be $^1H$ and/or $^{19}F$ MRI. The therapeutic drug or composition can comprise any of the compounds described herein. The method can comprise growing 3-D cultured cells; introducing the therapeutic compound or composition; and monitoring the effect of the therapeutic compound or composition on the cells using MRI.

In specific embodiments, the dynamics of T-Lymphoblastoid (CEM) cell growth influenced by colchicine derivatives in three-dimensional (3-D) cell cultures were examined. Other cancer cells can also be grown in this manner and examined, for example, CCRF-CEM (Leukemia), HL-60 (TB) (Leukemia), K-562 (Leukemia), MOLT-4 (Leukemia), RPMI-8226 (Leukemia), SR (Leukemia), A549/ATCC (Non-Small Cell Lung), EKVX (Non-Small Cell Lung), HOP-62 (Non-Small Cell Lung), HOP-92 (Non-Small Cell Lung), NCI-H226 (Non-Small Cell Lung), NCI-H23 (Non-Small Cell Lung), NCI-H322M (Non-Small Cell Lung), NCI-H460 (Non-Small Cell Lung), NCI-H522 (Non-Small Cell Lung), COLO 205 (Colon), HCC-2998 (Colon), HCT-116 (Colon), HCT-15 (Colon), HT29 (Colon), KM12 (Colon), SW-620 (CNS), SF-268 (CNS), SF-295 (CNS), SF-539 (CNS), SNB-19 (CNS), SNB-75 (CNS), U251 (CNS) (Melanoma), LOX IMVI (Melanoma), MALME-3M (Melanoma), M14 (Melanoma), MDA-MB-435 (Melanoma), SK-MEL-2 (Melanoma), SK-MEL-28 (Melanoma), SK-MEL-5 (Melanoma), UACC-257 (Melanoma), UACC-62 (Melanoma), IGR-OV1 (Ovarian), OVCAR-3 (Ovarian), OVCAR-4 (Ovarian), OVCAR-5 (Ovarian), OVCAR-8 (Ovarian), NCI/ADR-RES (Ovarian), SK-OV-3 (Ovarian), 786-0 (Renal), A498 (Renal), ACHN (Renal), CAKI-1 (Renal), RXF 393 (Renal), SN12C (Renal), TK-10 (Renal), UO-31 (Renal), PC-3 (Prostate), DU-145 (Prostate), MCF7 (Breast), MDA-MB-231/ATCC (Breast), HS 578T (Breast), MDA-N (Breast), BT-549 (Breast), T-47D (Breast), DLD-1 (Colon), KM20L2 (Colon), SNB-78 (CNS), XF 498 (CNS), RPMI-7951 (Melanoma), M19-MEL (Melanoma), RXF-631 (Renal), SN12K1 (Renal), MDA-MB-468 (Breast), P388 (Leukemia), and P388/ADR (Leukemia).

In an embodiment, the cells were cultured in a Hollow Fiber Bioreactor (HFB), $^1H$ and $^{19}F$ MRI was used to monitor changes in the 3-D cell cultures. $^{19}F$ MRI was used for visualization of the intracellular uptake of fluorine derivatives in the 3-D cell cultures. CEM cells profiled before and after treatment were investigated with high performance liquid chromatography (HPLC-UV). The viability of cells was compared to the efficacy of the compounds described herein ex vivo. The use of HFB permitted the formation of high density cancerous tissue for an MRI study ex vivo. In human body CEM tumour exists in 3-D environment, however, conventional monolayer cell cultures used in biological and toxicological studies are two dimensional (2-D). The ex vivo experiments described herein support non-invasive monitoring of drug release ex vivo.

In certain embodiments, fluorinated derivatives comprised modifications at the C-7 position ((28) to (38) and (47) to (49)). Properties of these compounds were compared and provide new insight into the mechanism of interaction with colchicine derivatives ex vivo. As $^{19}F$ MRI allows detection of uptake of fluorine derivatives uptake, quantification of the cells ex vivo was performed and the cells viability was measured using trypan blue. Moreover, the MRI technique used in this study was suitable for multiple, repeated measurements to observe dynamic changes in response to treatment and provided non-invasive characteristics of the 3-D tumour ex vivo.

The effect of the derivatives presented herein improved $IC_{50}$ and caused solid tumour suppression. The lack of clinical interest in the colchicine (1) arises from its toxicity.

Without being bound by theory, various arguments e.g. duration of the exposure to Colchicine analogues (2-38), interaction among cells, drug metabolization may be put forward to explain the difference in cell viability that correspond to growth inhibition using the prepared analogues. The fluorinated derivative (28-38) displayed high antagonistic potency on cell growth in 3-D. The use of $^1$H MRI provides a potential tool for the study of viability and treatment efficacy of the CEM cells. In the studied CEM cells, the $^{19}$F SI increased due to $^{19}$F uptake, however the cells that are successfully treated are no longer viable for trypan blue assays. Therefore, combined measurements of viability using trypan blue and drug uptake using $^{19}$F SI gave total cell number that is equal to the number of cells before treatment.

Considering the applied technique, HPLC has proven particularly effective in the determinations of apoptotic protein even in low concentrations. Moreover, reversed phase HPLC is a reliable method for the separation of a great number of proteins and peptides with high reproducibility. Therefore, a fractionation procedure was established to enrich less abundant proteins using RP HPLC. The cell viability caused by apoptosis has been suggested to be a major factor in cell death in treatment of malignancies, such as lymphoma. In particular, the HPLC profile explains why that nonviable cell that expresses specific receptors occurred mostly in treated cells. It has been also reported that determined Tn antigen is expressed in over 70% of human carcinoma cells.

$^{19}$F MRI and HPLC-UV are suitable for monitoring of viable and nonviable cells before and after treatments.

In more specific embodiments, cultured ex vivo T-Lymphoblastoid (CEM) cells respond to synthesized thiocolchicine and fluorine thiocolchicine derivatives. These compounds were examined in CEM cells ex vivo using $^1$H and $^{19}$F magnetic resonance imaging and spectroscopy (MRI/S) as well as electron impact mass spectrometry (EI-MS) and high performance liquid chromatography coupled with Ultra Violet (HPLC-UV). The three-dimensional (3-D) CEM cell culture morphology during treatment was monitored using 9.4 Tesla MRI system.

The effective concentrations of the derivatives described herein required to induce the growth block in CEM cells were relatively low, in nM range. Moreover, fluorinated derivatives have a higher potency than their nonfluorinated counterparts and are more hydrophobic and have higher intracellular intake. However, the non-fluorinated derivatives are still effective. Using noninvasive $^{19}$F MRI techniques, ex vivo fluorine containing drug uptake and cancer cell suppression resulted within 72 hours after drug administration.

The 3-D model of a tumor is a very useful model to monitor cell growth. In cell culture, a compound is in direct contact with the cells, and its concentration is constant during its time of action. The change in the concentration occurs only with labile compounds or by an interaction with the cells. Moreover, standard culture methods produce rather low cell concentrations, which are difficult or impossible to detect with MRI while 3-D provides a high enough concentration. MRI can identify suppressed regions of treated cells. Moreover, MRI can give insight into the treatment effects within a tumor over the long course of treatment.

β-tubulin Colchicine Binding Sites

Microtubules are the primary target for many successful anti-cancer drugs, the majority of which bind specifically to β-tubulin. Models of the five most prevalent human β-tubulin isotypes have been determined and the colchicine-binding site identified herein as the most promising for drug design based on isotype specificity. Using this binding site as a template, the colchicine derivatives described herein were computationally probed for affinity to the β-tubulin isotypes. These compounds exhibited an $IC_{50}$ much lower than values previously reported for either colchicine or paclitaxel. There is a correlation between computational binding predictions and $IC_{50}$ values, demonstrating the utility of computational screening in the design of more effective colchicine derivatives.

Colchicine binding has been examined. The sequence of residues making up the colchicine binding site shows the greatest variation (77.8% identity) among all of the human tubulin isotypes (Huzil J. T. et al., Nanotechnology. 2006: 17:S90-S100). This binding site has previously been shown to interact with several natural compounds including colchicinoids, the benzimidazoles (Laclette J. P. et al., Biochem Biophys Res Commun. 1980; 92:417-23; Tahir S. K., Biotechniques. 2000; 29:156-60; Russell G. J. et al., Biochem. Mol. Biol. Int. 1995; 35:1153-9; and Hoebeke J. et al., Biochem Biophys. Res. Commun. 1976; 69:319-24) and podophyllotoxin (Ravelli R. B. et al., Nature. 2004; 428: 198-202) making it amenable to several binding conformations (Garland D. L., Biochemistry. 1978; 17:4266-72; Sackett D. L. et al., Biochemistry, 1993; 32:13560-5; and Andreu J. M. et al., Biochemistry. 1982; 21:6465-76; Chaudhuri A. R. et al., J. Mol. Biol., 2000; 303:679-92). Colchicine has extremely strong anti-mitotic activity that is only observed at toxic or near toxic levels which, while limiting its use as a cancer treatment, is used herein as a standard for comparison of similar compounds with increased selectivity towards tubulin isotypes expressed in cancer cells.

One series of derivatives was designed with modifications to reduce tubulin binding through increased van der Waals interactions, while the second series of derivatives incorporated modifications designed to increase binding to tubulin. Computational screening and cytotoxicity assays demonstrated that higher affinity colchicine derivatives were found to be superior to colchicine in their effects against cancerous cell lines, however, the others were effective against cancer cell lines without the disadvantage of colchicine toxicity.

While there is a plethora of structural information regarding tubulin's interactions with several ligands, tubulin's conformation decays over time and the binding of a drug can itself cause significant conformational changes within the protein itself (Luduena R. F. et al., Biochem. 1995; 34:15751-9; Chaudhuri A. R. et al., J. Mol. Biol., 2000; 303:679-92; and Schwarz P. M. et al., Biochem. 1998; 37:4687-92). Modeling predictions using a particular, fixed, conformation of a binding site may therefore be unreliable. This is especially true for colchicine binding, where β-tubulin in its unbound form shows a complete absence of the colchicine binding cavity (Nogales E. et al., Nature. 1995; 375:424-7). In order to overcome this limitation, firstly, three representative models of the colchicine binding site as it is found throughout the human β-tubulin isotypes has been created. Secondly, a systematic docking procedure has been performed, which attempts to sample the conformational space of the colchicine binding site through a simulated annealing method.

Using computational modeling methods, several modifications to colchicine have been introduced in an attempt to design a model system capable of increasing specificity for β-tubulin isotypes expressed in cancer cells. To examine the differences between isotypes, a cavity was probed located below the bound colchicine in the crystal structure. In particular, several C3-demethylthiocolchicine derivatives and C1-demethylcolchicine derivatives were synthesized.

In general, the "higher affinity" group of derivatives (C3 position) yielded better cytotoxicity results than the "lower affinity" group (C1 position). However, both groups were effective. It was consistent that (8), (7), (7a) and (9) were moderately better than colchicine in cytotoxicity assays and (40), (42), (43), (50), (51), (53) and (54) were consistently the most effective. Small non-polar modifications to the C1 position had better general binding than colchicine, while straight chain non-polar modifications to the C3 position in thiocoichicine were consistently much better than colchicine. A significant correlation was produced that could implicate a single colchicine derivative in being capable of differentiating between isotypes, the distribution of colchicine binding site types (type-I and type-III) follows the expected function of the tubulin isotypes in both chemotherapy resistance and cancer development, in which the βIII and βV isotypes are implicated. The most potent derivative (43) had an IC50 of 2.13±0.77 nM, a value that was at least 15 fold lower than that previously reported for either colchicine or paclitaxel (Cragg G. M. et al., Anticancer agents from natural products. CRC Press; 2005).

Ultimately tubulin-isotype specific drugs should exhibit fewer side effects than their currently prescribed counterparts. This is because they will bind to and disrupt those microtubules only in cells expressing a particular β-tubulin isotype associated with cancer development or progression. These results also suggest that modeling is likely to generate better drugs and that rational drug design is possible with tubulin.

When introducing elements disclosed herein, the articles "a", "an", "the", and "said" are intended to mean that there are one or more of the elements.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Material and Methods

All chemical compounds and colchicine, N-[(7S)-1,2,3,10-tetramethoxy-9-oxo-5,6,7,9-tetrahydrobenzo[α]heptalen-7-yl]acetamide (1), used in the studies were purchased from Sigma-Aldrich (Oakville, ON, Canada).

Synthesis of the Colchicine Compounds

Figure 2:
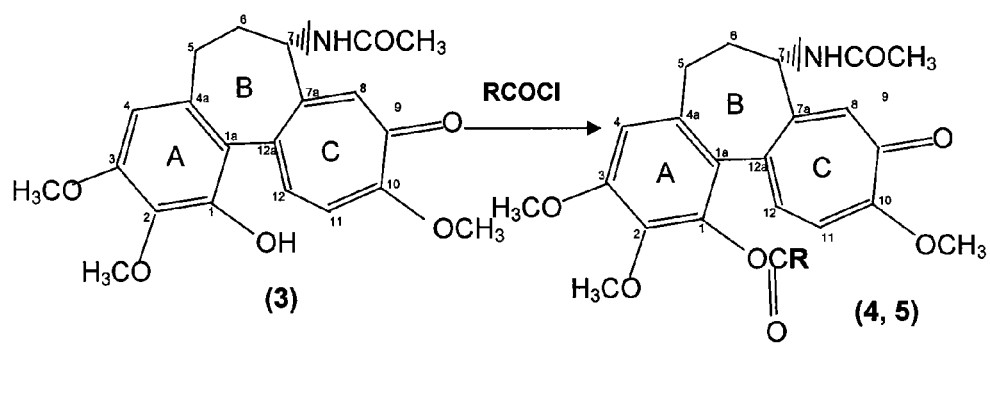
FIG. 2 shows a synthetic scheme for making compounds (4) and (5)

See FIGS. 1-3 for Synthetic Schemes.
N-[(7S)-2,3,10-trimethoxy-1-((methyl)carbonyloxy)-9-oxo-5,6,7,9-tetrahydrobenzo[α]heptalen-7-yl]acetamide (2) and N-[(7S)-1-hydroxy-2,3,10-trimethoxy-9-oxo-5,6,7,9-tetrahydrobenzo[α]heptalen-7-yl]acetamide (3). The synthesis of (2) and (3) was adapted from Blade-Font (A. Blade-Font, Afinidad, 36 (1979) 329-331) and is presented in FIG. 1.

N-[(7S)-1-((ethyl)carbonyloxy)-2,3,10-trimethoxy-9-oxo-5,6,7,9-tetrahydrobenzo[α]heptalen-7-yl]cetamide (4) and N-[(7S)-1-(((methyl)ethyl)carbonyloxy)-2,3,10-trimethoxy-9-oxo-5,6,7,9-tetrahydrobenzo [α]heptalen-7-yl]acetamide (5).

1 mmol of (2) was dissolved in 2.5 mL of sodium hydroxide solution. The solution was cooled to 0° C. 1 mmol of CH$_3$CH$_2$COCl or (CH$_3$)CH(CH$_3$)COCl was dissolved in 3.5 mL acetone, and added to compounds (4) or (5). The solution was allowed to stand for 15 h and then 25 mL of alkaline water was added. Chloroform was used to extract the resulting product and drying over magnesium sulfate. The syntheses of (4) and (5) are presented in FIG. 2.

N-[(7S)-1-(ethoxy)-2,3,10-trimethoxy-9-oxo-5,6,7,9-tetrahydrobenzo[α]heptalen-7-yl]acetamide (6);
N-[(7S)-1-(ethoxy-1-methyl)-2,3,10-trimethoxy-9-oxo-5,6,7,9-tetrahydrobenzo[α]heptalen-7-yl]acetamide (7);
N-[(7S)-2,3,10-trimethoxy-1-(2-methylpropoxy)-9-oxo-5,6,7,9-tetrahydrobenzo[α]heptalen-7-yl]acetamide (7a);
N-[(7S)-1-(butoxy)-2,3,10-trimethoxy-9-oxo-5,6,7,9-tetrahydrobenzo[α]heptalen-7-yl]acetamide (7b);
N-[(7S)-1-((but(3-en)oxy)-2,3,10-trimethoxy-9-oxo-5,6,7,9-tetrahydrobenzo[α]heptalen-7-yl]acetamide (7c);
N-[(7S)-2,3,10-trimethoxy-9-oxo-1-(propanoxy)-5,6,7,9-tetrahydrobenzo[α]heptalen-7-yl]acetamide (8);
N-[(7S)-2,3,10-trimethoxy-9-oxo-1-((prop(2-en)oxy)-5,6,7,9-tetrahydrobenzo [α]heptalen-7-yl]acetamide (9);
N-[(7S)-2,3,10-trimethoxy-9-oxo-1-((phenyl)methoxy)-5,6,7,9-tetrahydrobenzo [α]heptalen-7-yl]acetamide (10);
N-[(7S)-2,3,10-trimethoxy-9-oxo-1-(((3-methoxy)propan)oxy)(3-methoxy))-5,6,7,9-tetrahydrobenzo[α]heptalen-7-yl]acetamide (11);
N-[(7S)-2,3,10-trimethoxy-9-oxo-1-((phenyl(3-chloro))methoxy)-5,6,7,9-tetrahydrobenzo[α]heptalen-7-yl]acetamide (12);
N-[(7S)-2,3,10-trimethoxy-9-oxo-1-((pyridin(3))yl)-5,6,7,9-tetrahydrobenzo[α]heptalen-7-yl]acetamide (13);
N-[(7S)-2,3,10-trimethoxy-9-oxo-1-((phenyl(2-chloro))methoxy)-5,6,7,9-tetrahydrobenzo[α]heptalen-7-yl]acetamide (14);
N-[(7S)-2,3,10-trimethoxy-9-oxo-1-(((phenyl(4-chloro))methoxy)-5,6,7,9-tetrahydrobenzo[α]heptalen-7-yl]acetamide (15);
N-[(7S)-2,3,10-trimethoxy-1-((methyl)cyclohexane)-9-oxo-5,6,7,9-tetrahydrobenzo[α]heptalen-7-yl]acetamide (16).

1 mmol of (2) compound was dissolved in 2.5 mL of sodium hydroxide solution and solution was cooled to 0° C. 1 mmol of bromide derivatives (e.g. 1-bromoethane for (6), 2-bromopropane for (7), 1-bromo-2-methylpropane for (7a), 1-bromo-butane for (7b), 4-bromobut-1-ene for (7c), 1-bromopropane for (8), 3-bromoprop-1-ene for (9), (bromomethyl)benzene for (10), 1-methoxy-2-bromoethane for (11), 1-bromomethyl-3-chlorobenzene for (12), 3-(bromomethyl)pyridine for (13), 1-bromomethyl-2-chlorobenzene for (14), 1-bromomethyl-4-chlorobenzene for (15), and (bromomethyl)cyclohexane for (16)) was dissolved in 3.5 mL acetone. Each solution was allowed to stand for 15 h. Then 25 mL of alkaline water was added. Chloroform was used to extract the compound, which was dried over magnesium sulfate. The syntheses of (6-16) are presented in FIG. 3.

General Procedure for the Preparation of N-deacetyl-N-(N-trifluoroacetylaminoacyl) colchicine:

3 mmol of the derivative (6-16) in methanol (50 mL) and 2N HCl (25 mL) was heated at 90° C. with stirring for 1 day. The reaction mixture was cooled and was neutralized with NaHCO$_3$. Product was extracted with methylene chloride and washed with brine. The extract was dried over Na$_2$SO$_4$ and was evaporated. The deacetylated compounds (17-27) were crystallized from CH$_2$Cl$_2$.

1 mmol of deacetylated compound (17-27) and [(trifluoroacetyl)amino]acetic acid (1 mmol) was dissolved at room temperature in dichloromethane (6 mL). Dicyclohexylcarbodiimide (1 mmol) was added. After 2 h the suspension was cooled to 0° C. and filtrated. Products (28-38) were chromatographed on silica gel column eluting with dichloromethane/methanol (1:0 to 0:1). Crystallization of (28-38) were performed with dichloromethane:ethyl ether (1:1).

Analytical Analysis (2) $C(23)H(25)O(7)N(1)$; requires M, 427, found EIMS m/e 427.1 ($M^+$); (3) $C(21)H(23)O(6)N(1)$; requires M, 385, found EIMS m/e 385.1 ($M^+$); (4) $C(24)H(27)O(7)N(1)$; requires M, 441, found EIMS m/e 441.1 ($M^+$); (5) $C(25)H(29)O(7)N(1)$; requires M, 455 found EIMS m/e 455.0 ($M^+$); (6) $C(23)H(27)O(6)N(1)$; requires M, 413, found EIMS m/e 413.1 ($M^+$); Anal. Calc. C % 66.83, H % 6.55, N % 23.22 found: C % 66.82, H % 6.54, N % 23.22; (7) $C(24)H(29)O(6)N(1)$; requires M, 427, found EIMS m/e 427.1 ($M^+$); Anal. Calc. C % 67.44, H % 6.77, N % 3.22, found: C % 67.41, H % 6.73, N % 3.21; (8) $C(24)H(29)O(6)N(1)$; requires M, 427, found EIMS m/e 427.1 ($M^+$); Anal. Calc. C % 67.44, H % 6.79, N % 32.78, found: C % 67.44, H % 6.80, N % 32.77; (9) $C(24)H(27)O(6)N(1)$; requires M, 425, found EIMS m/e 425.1 ($M^+$); Anal. Calc. C % 67.76, H % 6.35, N % 3.29 found: C % 67.77, H % 6.33, N % 3.28; (10) $C(28)H(28)O(6)N(1)$; requires M, 475, found EIMS m/e 475.2 ($M^+$); Anal. Calc. C % 70.88, H % 5.91, N % 2.95 found: C % 70.87, H % 5.92, N % 2.93; (11) $C(24)H(29)O(7)N(1)$; requires M, 443, found EIMS m/e 443.1 ($M^+$); Anal. Calc. C % 65.01, H % 6.54, N % 3.16 found: C % 65.02, H % 6.53, N % 3.11; (12) $C(28)H(27)O(6)N(1)Cl(1)$; requires M, 509, found EIMS m/e 509.1 ($M^+$); Anal. Calc. C % 71.04, H % 6.13, N % 2.93 found: C % 71.05, H % 6.12, N % 2.95; (13) $C(27)H(28)O(6)N(2)$; requires M, 476, found EIMS m/e 476.1 ($M^+$); Anal. Calc. C % 68.06, H % 5.88, N % 5.88, found: C % 68.09, H % 5.86, N 5.89%; (14) $C(28)H(28)O(6)N(1)Cl(1)$; requires M, 509, found EIMS m/e 509.1 ($M^+$); Anal. Calc. C % 66.01, H % 5.50, N % 2.94, Cl% 6.87 found: C % 66.03, H % 5.51, N % 2.95, Cl% 6.88; (15) $C(24)H(29)O(7)N(1)$; requires M, 509, found EIMS m/e 509.1 ($M^+$); Anal. Calc. C % 65.01, H % 6.09, N % 3.16, Cl% 7.90. found: C % 65.02, H % 6.07, N % 3.10, Cl% 7.92; (16) $C(28)H(34)O(6)N(1)$; requires M, 495, found EIMS m/e 495.2 ($M^+$); Anal. Calc. C % 70.02, H % 7.09, N % 2.91 found: C % 70.04, H % 7.08, N % 2.93; (17) $C(21)H(25)O(5)N(1)$; Anal. Calc. C % 67.92, H % 7.27, N % 3.77 found: C % 67.93, H % 7.28, N % 3.78; (18) $C(22)H(27)O(5)N(1)$ Anal. Calc. C % 68.57, H % 7.01, N % 3.77 found: C % 68.59, H % 7.03, N % 3.79; (19) $C(22)H(27)O(5)N(1)$; Anal. Calc. C % 68.63, H % 7.04, N % 3.78 found: C % 68.62, H % 7.05, N % 3.79; (20) $C(22)H(25)O(5)N(1)$; Anal. Calc. C % 68.92, H % 6.52, N % 3.65 found: C % 68.94, H % 6.53, N % 3.67; (21) $C(26)H(26)O(5)N(1)$; Anal. Calc. C % 72.22, H % 6.01, N % 3.24 found: C % 72.21, H % 6.04, N % 3.23; (22) $C(22)H(27)O(6)N(1)$; Anal. Calc. C % 65.83, H % 6.73, N % 3.49 found: C % 65.82, H % 6.73, N % 3.48; (23) $C(26)H(25)O(5)N(1)Cl(1)$; Anal. Calc. C % 66.95, H % 5.36, N % 3.02, Cl 7.51 found: C % 66.93, H % 5.34, N % 3.01, Cl 7.53; (24) $C(22)H(26)O(5)N(1)$; Anal. Calc. C % 81.25, H % 6.77, N % 3.64 found: C % 81.26, H % 6.78, N % 3.66; (25) $C(26)H(26)O(5)N(1)Cl(1)$; Anal. Calc. C % 66.80, H % 5.56, N % 2.99, Cl% 7.49, found: C % 66.81, H % 5.55, N % 2.98, Cl% 7.48; (26) $C(22)H(27)O(5)N(1)$; Anal. Calc. C % 77.92, H % 7.01, N % 3.63, found: C % 77.93, H % 7.03, N % 3.65; (27) $C(26)H(32)O(5)N(1)$; Anal. Calc. C % 71.23, H % 7.30, N % 3.19 found: C % 71.22, H % 7.32, N % 3.20; (28) $C(25)H(27)O(7)N(2)F(3)$; Anal. Calc. C % 57.25, H % 5.15, N % 5.18, F % 10.85, found: C % 57.25, H % 4.99, N % 5.34, F % 10.86; (29) $C(26)H(29)O(7)N(2)F(3)$; Anal. Calc. C % 57.99, H % 5.39, N % 5.20, F % 10.59 found: C % 56.38, H % 5.3, N % 5.3, F % 10.87; (30) $C(26)H(29)O(7)N(2)F(3)$; Anal. Calc. C % 57.99, H % 5.39, N % 5.20, F % 10.59, found: C % 57.58, H % 5.32, N % 5.28, F % 10.59; (31) $C(26)H(27)O(7)N(2)F(3)$; Anal. Calc. C % 57.99, H % 5.39, N % 5.20, F % 10.56, found: C % 57.99, H % 5.88, N % 5.28, F % 10.55; (32) $C(30)H(28)O(7)N(2)F(3)$; Anal. Calc. C % 59.92, H % 4.66, N % 4.65, F % 9.46. found: C % 59.71, H % 4.65, N % 4.37, F % 9.49; (33) $C(26)H(29)O(7)N(2)F(3)$; Anal. Calc. C % 57.99, H % 5.39, N % 5.20, F % 10.59 found: C % 56.38, H % 5.21, N % 4.68, F % 9.55; (34) $C(30)H(27)O(7)N(2)Cl(1)F(3)$; Anal. Calc. C % 56.77, H % 4.28, N % 4.13, F % 8.41, found: C % 56.74, H % 4.29, N % 4.12, F % 8.43; (35) $C(26)H(27)O(7)N(2)F(3)$; Anal. Calc. C % 58.20, H % 4.86, N % 4.69, F % 9.56, found: C % 58.12, H % 4.87, N % 4.69, F % 9.57; (36) $C(30)H(28)O(7)N(2)Cl(1)F(3)$; Anal. Calc. C % 58.06, H % 4.15, N % 4.12, F % 8.41 found: C % 58.06, H % 4.14, N % 4.13, F % 8.40; (37) $C(26)H(28)O(7)N(2)Cl(1)F(3)$; Anal. Calc. C % 54.54, H % 4.87, N % 4.73, F % 9.25. found: C % 54.53, H % 4.88, N % 4.72, F % 9.26; (38) $C(30)H(34)O(7)N(2)F(3)$; Anal. Calc. C % 60.91, H % 5.75, N % 4.73, F % 9.64. found: C % 60.79, H % 5.67, N % 4.63, F %9.67.

Synthesis of the Thiocolchicine Compounds (FIG. 4)

Thiocolchicine, N-[(7S)-1,2,3-trimethoxy-10-methylsulfanylo-9-oxo-5,6,7,9-tetrahydrobenzo[α]heptalen-7-yl]acetamide (39): Colchicine (1) (1 mmol) was dissolved in 10 mL of methanol/dimethylformamide (1:1) at 70-80° C. The solution was cooled to room temperature and sodium methanethiolate (2 mmol) was added. The mixture solution was stirred overnight. Water (20 mL) was added, and the reaction mixture was extracted with $CH_2Cl_2$ (10 mL), was dried over $Na_2SO_4$ and concentrated. Crystallization of the residue from ethyl ether/acetone (1:1) gave product (39) with 71% yield.

N-[(7S)-3-hydroxy-1,2-dimethoxy-3-hydroxy-10-methylsulfanyl-9-oxo-5,6,7,9-tetrahydrobenzo[α]heptalen-7-yl] acetamide (40): 10 mL of methanol was used to dissolve 1 mmol of thiocolchicine (39) and 30 mL of 0.2N of hydrochloric acid was added. The methanol was evaporated, cooled and sodium hydroxide solution was added until pH value was 11 and the resulting alkaline solution was extracted with chloroform in order to free it from non-phenolic substances. The sodium hydroxide solution, (color red), was acidified with hydrochloric acid and was extracted with chloroform. After drying and evaporation, the yield of (40) was 58%.

N-[(7S)-1,2-dimethoxy-10-methylsulfanyl-9-oxo-3-(prop (2-en)oxy)-5,6,7,9-tetrahydrobenzo[α]heptalen-7-yl]acetamide (41), N-[(7S)-3-ethoxy-1,2-dimethoxy-10-methylsulfanyl-9-oxo-5,6,7,9-tetrahydrobenzo[α]heptalen-7-yl] acetamide (42), and N-[(7S)-3-propoxy-1,2-dimethoxy-10-methylsulfanyl-9-oxo-5,6,7,9-tetrahydrobenzo[α]heptalen-7-yl]acetamide (43): 1 mmol of (40) compound was dissolved in 2.5 mL of 1N sodium hydroxide solution. The resulting solution was cooled to 0° C. and 3-bromoprop-1-ene (1 mmol) to obtain compound (41); 1-bromoethane (1 mmol) to obtain compound (42); or 1-bromopropane (1 mmol) to obtain compound (43), was dissolved in 3.5 mL acetone and added to the cooled solution. The solution was allowed to stand for 15 h and then 25 mL of alkaline water was added. Chloroform was used to extract the resulting product and drying over magnesium sulfate. The yield of (41) was 68% and the yield of (42) was 71%.

A Preparation of the N-deacetyl-N-(N-trifluoroacetylamino-acyl) thiocolchicine:

N-[(7S)-3-hydroxy-1,2-dimethoxy-10-methylsulfanyl-9-oxo-5,6,7,9-tetrahydrobenzo[α]heptalen-7-yl]amine (44);

N-[(7S)-1,2-dimethoxy-10-methylsulfanyl-9-oxo-3-(prop (2-en)oxy)-5,6,7,9-tetrahydrobenzo[α]heptalen-7-yl] amine (45);

N-[(7S)-3-ethoxy-1,2-dimethoxy-10-methylsulfanyl-9-oxo-5,6,7,9-tetrahydrobenzo[α]heptalen-7-yl]amine (46);
N-[(7S)-3-hydroxy-1,2-dimethoxy-10-methylsulfanyl-9-oxo-5,6,7,9-tetrahydrobenzo[α]heptalen-7-yl]-N-[(trifluoroacetyl)glycyl]acetamide (47);
N-[(7S)-1,2-dimethoxy-10-methylsulfanyl-9-oxo-3-(prop-2-enoxy)-5,6,7,9-tetrahydrobenzo[α]heptalen-7-yl]-N-[(trifluoroacetyl)glycyl]acetamide (48);
N-[(7S)-3-ethoxy-1,2-dimethoxy-10-methylsulfanyl-9-oxo-5,6,7,9-tetrahydrobenzo[α]heptalen-7-yl]-N-[(trifluoroacetyl)glycyl]acetamide (49).

Each derivate (44-46), and (47-49) was prepared in a similar way. 1 mmol of appropriate derivative (40) or (41) or (42) was dissolved in methanol (20 mL) with 2N HCl (10 mL) and heated at 90° C. and stirred for a 24 h. The reaction mixture was cooled, neutralized with NaHCO$_3$ and extracted with CH$_2$Cl$_2$. Extract was dried over Na$_2$SO$_4$ and evaporated. The crystallization was from (1:1) CH$_2$Cl$_2$/CH$_3$OH. The yield of deacetylated compound (44), (45), (46) was 58%, 63% and 71%, respectively.

1 mmol of deacetylated compound of (44) or (45) or (46) and N-trifluoroacetyloamino acid (1 mmol) were dissolved at room temperature and dichloromethane (6 mL) was added with stirring. Dicyclohexylcarbodiimide (1 mmol) was added to the suspension and, after 2 h cooled to 0° C. and filtrated. Each compound (47) or (48) or (49) was crystalized from dichloromethane:ethyl ether (1:1) solution. The yield of (47), (48), and (49) was 64%, 67% and 75%, respectively.

Analysis of (39), (40-42), (44-46) and (47-49) Compounds

Colchicine (1): M.p. 275° C.; (39): M.p. 250° C.-252° C.; Anal. Calc. for C(22)H(25)N(1)O(5)S(1): C % 63.60, H % 6.06, N % 3.37, S %7.72found: C % 63.71, H % 6.15, N % 3.42, S % 7.79; (40): M.p. 306° C.; Anal. Calc. for C(21)H(23)O(5)N(1)S(1): C % 62.8, H % 5.8, N % 3.5, S % 8.0, found: C % 62.9, H % 5.8, N % 3.3, S % 7.5; Requires M, 401.1, found EIMS m/e 401.1 (M$^+$); (41): M.p. 306° C.; Anal. Calc. for C(24)H(27)O(5)N(1)S(1), C % 65.3, H % 6.12, N % 3.17, S % 7.24, found: C % 65.07, H % 6.59, N % 3.21, S % 7.28; Requires M, 454.5, found EIMS 454.5 (M$^+$Na$^+$); 442.5; (42): M.p. 273° C.; Anal. Calc. for C(23)H(27)O(5)N(1)S(1), C % 64.33, H % 18.64, N % 3.26, S % 7.45, found: C % 64.4, H %18.9, N % 3.27, S % 7.61; Requires M, 452.6, found EIMS 452.6 (M$^+$Na$^+$); (44):M.p. 281° C.; Anal. Calc. for C(19)H(21)O(4)N(1)S(1), C % 63.51, H % 5.91, N % 3.88, S % 8.92, found: C % 63.55, H % 5.83, N % 3.75, S % 8.93; (45): M.p. 254° C.; Anal. Calc. for C(22)H(25)O(4)N(1)S(1), C % 65.8, H % 6.77, N % 3.52, S % 7.99, found: C % 65.83, H % 6.49, N % 3.63, S % 8.31; (46): M.p. 276° C.; Anal. Calc. for C(21)H(25)O(4)N(1)S(1), C % 65.81, H % 6.50, N % 3.6, S % 8.24, found: C % 65.12, H % 6.54, N % 3.57, S % 8.27; (47): M.p. 284° C.; Anal. Calc. for C(23)H(23)O(6)N(2)S(1)F(3), C % 55.42, H % 4.61, N % 2.92, S % 6.42, F % 11.44 found: C % 55.43, H % 4.62, N % 2.91, S % 6.42, F % 11.44; (48): M.p. 324° C.; Anal. Calc. for C(26)H(27)O(6)N(2)S(1)F(3), C % 56.52, H % 4.89, N % 5.07, S % 5.79, F % 10.32 found: C % 56.52, H % 4.87, N % 7.01, S % 5.79, F % 10.32; (49): M.p. 256° C.; Anal. Calc. for C(25)H(27)O(6)N(2)S(1)F(3), C % 57.03, H % 5.13, N % 5.32, S % 6.08, F % 10.87 found: C % 53.67, H % 4.5, N % 5.32, S % 6.05; F % 10.85.

Specific Syntheses of the Colchicine Derivatives
Compound (2)

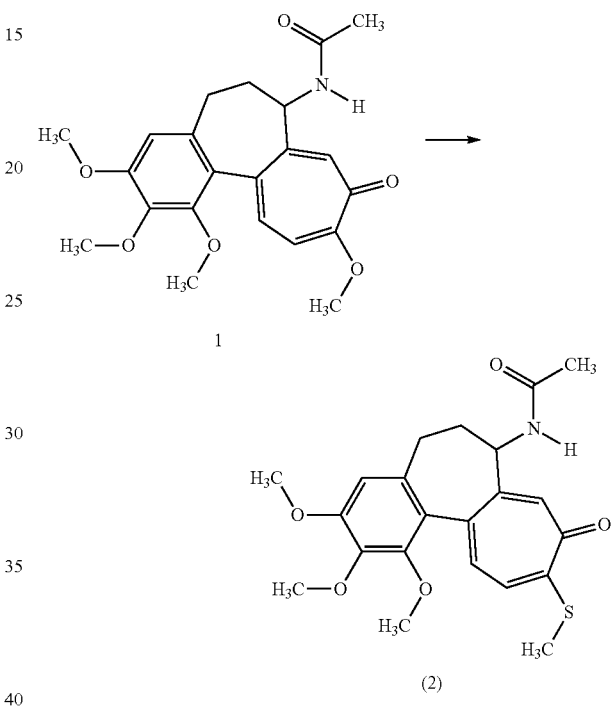

A solution of 1 (30.0 g) and sodiumthiomethoxide (30.0 mL) in water (2000 mL) was stirred at rt overnight. The reaction solution was extracted with dichloromethane and the organic layer was concentrated to give the crude product. The crude product was purified by silica gel column chromatography to give the desired product (20.0 g, 65%).

Compounds (6), (17) and (28)

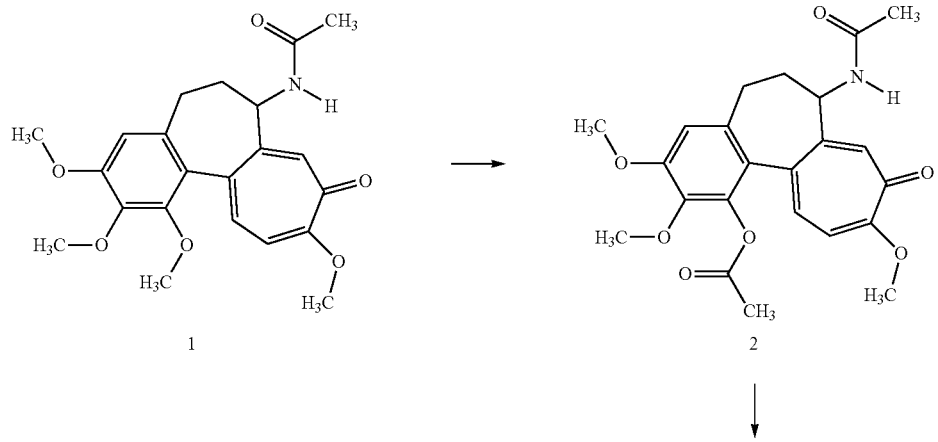

-continued

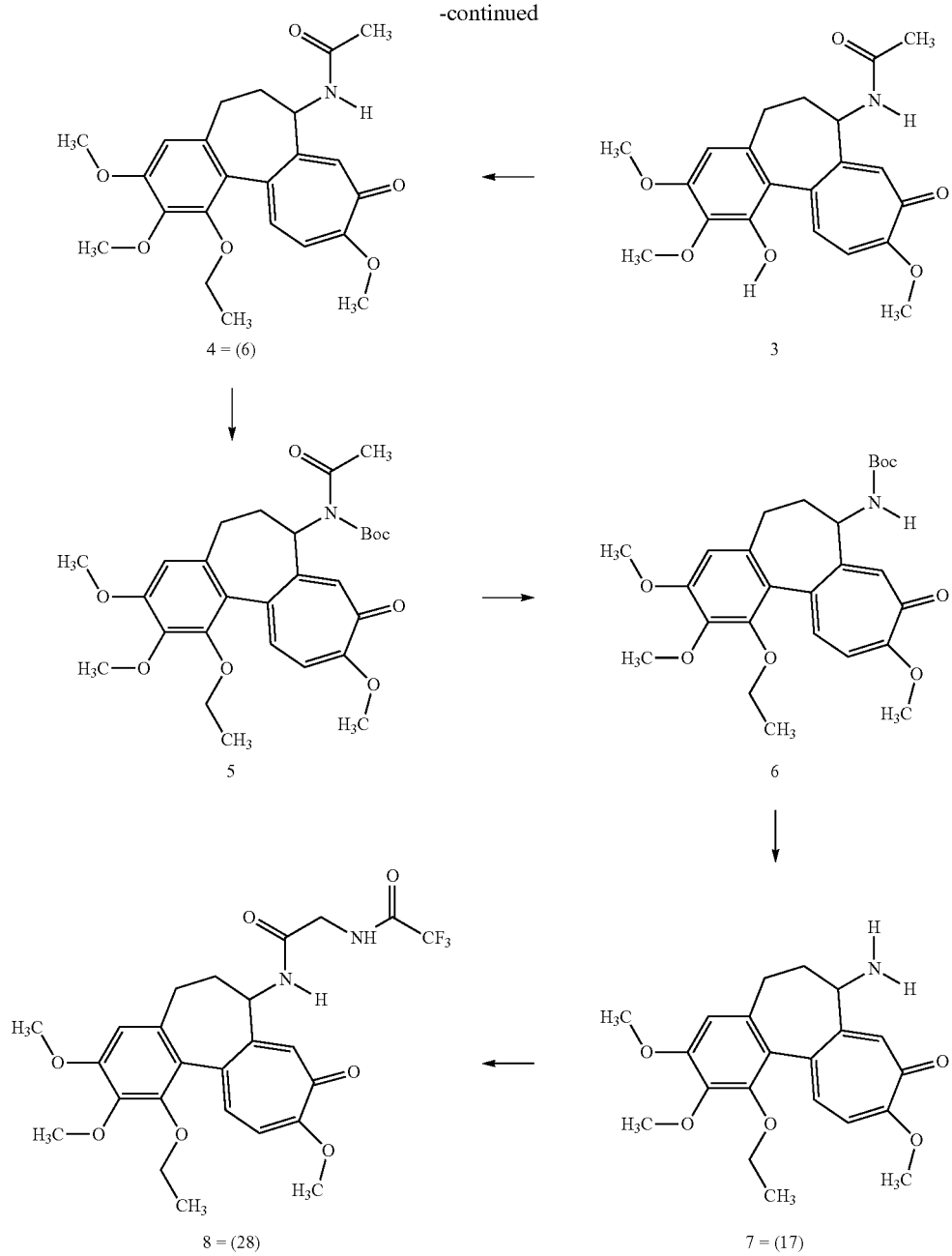

To a solution of 1 (1.0 g, 2.51 mmol) and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), bromoethane (450 mg, 4.16 mmol) and potassium carbonate (1.2 g, 8.31 mmol) in DMF (20 mL) was stirred at 90° C. for 2 h. The reaction mixture was poured in water, extracted with ethyl acetate and concentrated to give the crude product. The crude product was purified by silica gel column chromatography to give the desired product (0.5 g, 60%).

A mixture of 4 (700 mg, 1.69 mmol), (Boc)2O (3.7 g, 16.95 mol) and DMAP (83 mg, 0.68 mmol) in THF (15 mL) was refluxed overnight. The reaction mixture was washed with water, dried and concentrated to give the crude product which was used directly for the next step.

A solution of 5 (crude) and sodium methoxide (365.0 mg, 6.76 mmol) in methanol (15 mL) was stirred at it for 2 h. Then water was added and extracted with dichloromethane. The extracts were concentrated to give the crude product. The crude product was purified by silica gel column chromatography to give the desired product (0.6 g).

A solution of 6 (600 mg, 1.27 mmol) and trifluoroacetic acid (5 mL) in dichloromethane (5 mL) was stirred at it for 3 hours. The reaction solution was concentrated to give the product (0.45 g, 96%).

A solution of 7 (50 mg, 0.13 mmol), EDCl (39 mg, 0.20 mmol), HOBT (27 mg, 0.20 mmol), F₃CGlyOH (28 mg, 0.16 mmol) and triethylamine (54 mg, 0.54 mmol) in dichloromethane (3 mL) was stirred at it overnight. The reaction mixture was washed with water, dried and concentrated to give the crude product. The crude product was purified by chromatography to give the desired product (22 mg, 31%).
Compounds (11), (22) and (33)
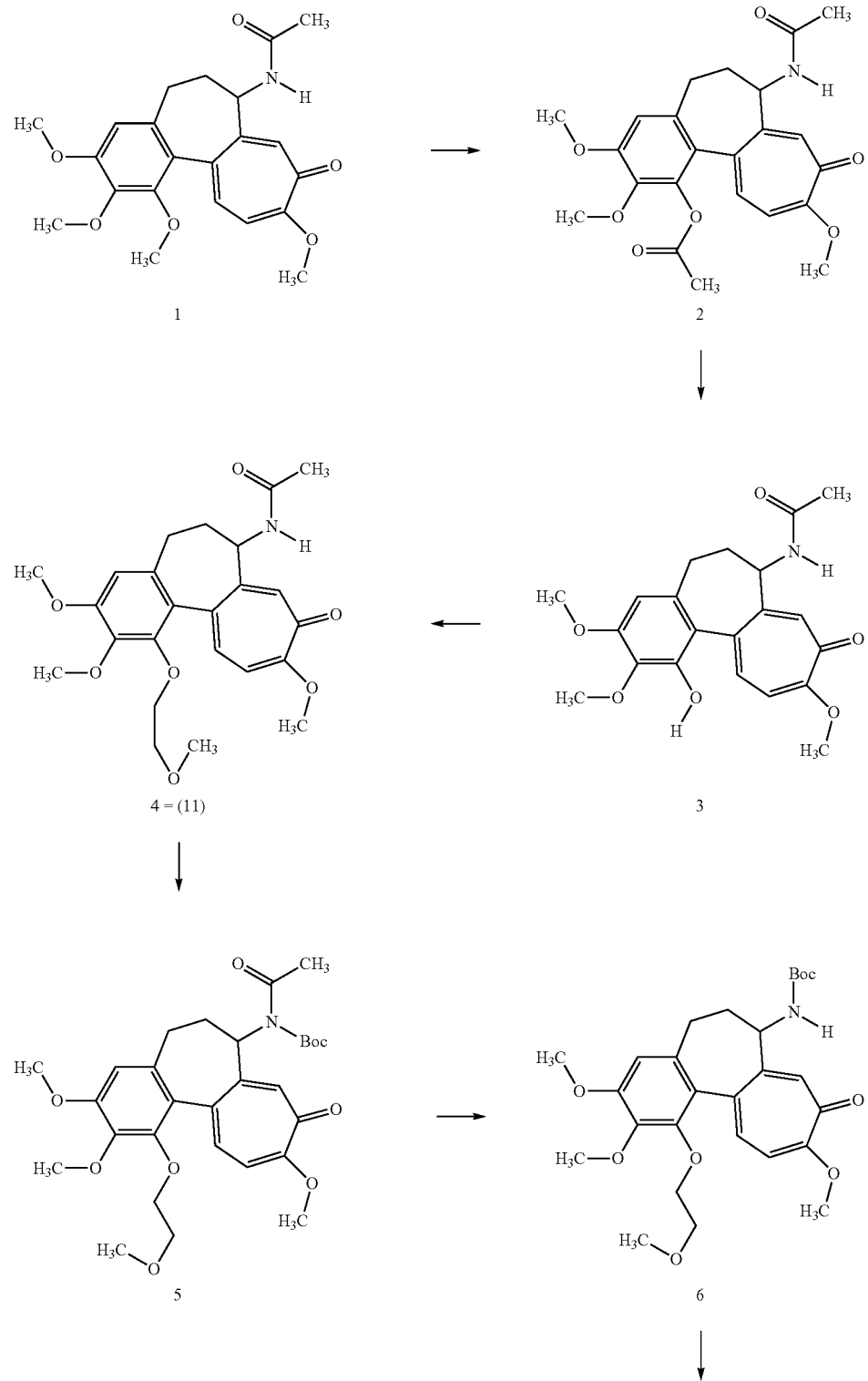

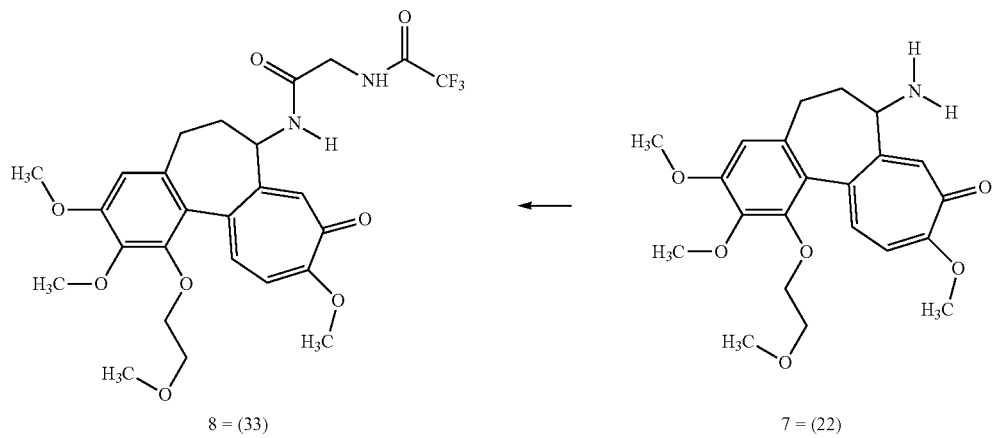

8 = (33)    7 = (22)

To a solution of 1 (1.0 g, 2.51 mmol), and acetylchloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), 1-bromo-2-methoxyethane (580 mg, 4.16 mmol) and potassium carbonate (1.15 g, 8.31 mmol) in DMF (20 mL) was stirred at 75° C. for 3 h. The reaction mixture was poured in water, extracted with ethyl acetate and concentrated to give the crude product. The crude product was purified by silica gel column chromatography to give the desired product (0.5 g, 54%).

A mixture of 4 (500 mg, 1.13 mmol), (Boc)2O (2.5 g, 11.29 mmol) and DMAP (55 mg, 0.45 mmol) in THF (10 mL) was refluxed overnight. The reaction mixture was washed with water, dried and concentrated to give the crude product which was used directly for the next step.

A solution of 5 (crude) and sodium methoxide (244.0 mg, 4.52 mmol) in methanol (15 mL) was stirred at it for 2 h. Then water was added and extracted with dichloromethane. The extract were concentrated to give the crude product. The crude product was purified by silica gel column chromatography to give the desired product (0.45 g).

A solution of 6 (0.6 g, 1.20 mmol) and trifluoroacetic acid (5 mL) in dichloromethane (5 mL) was stirred at it for 3 hours. The reaction solution was concentrated to give the product (0.45 g, 94%).

A solution of 7 (65 mg, 0.16 mmol), EDCl (46 mg, 0.24 mmol), HOBT (32 mg, 0.24 mmol), F$_3$CGlyOH (42 mg, 0.24 mmol) and triethylamine (65 mg, 0.65 mmol) in dichloromethane (3 mL) was stirred at rt overnight. The reaction mixture was washed with water, dried and concentrated to give the crude product. The crude product was purified by chromatography to give the desired product (25 mg, 28%).

Compounds (13), (24) and (35)

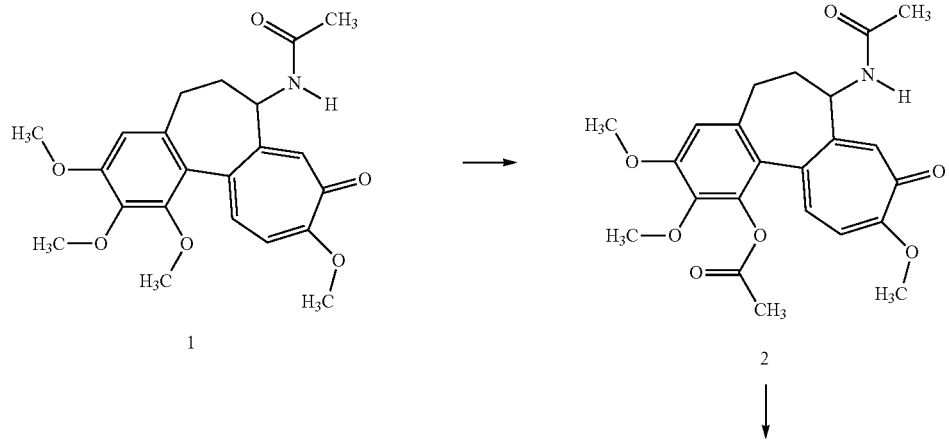

-continued

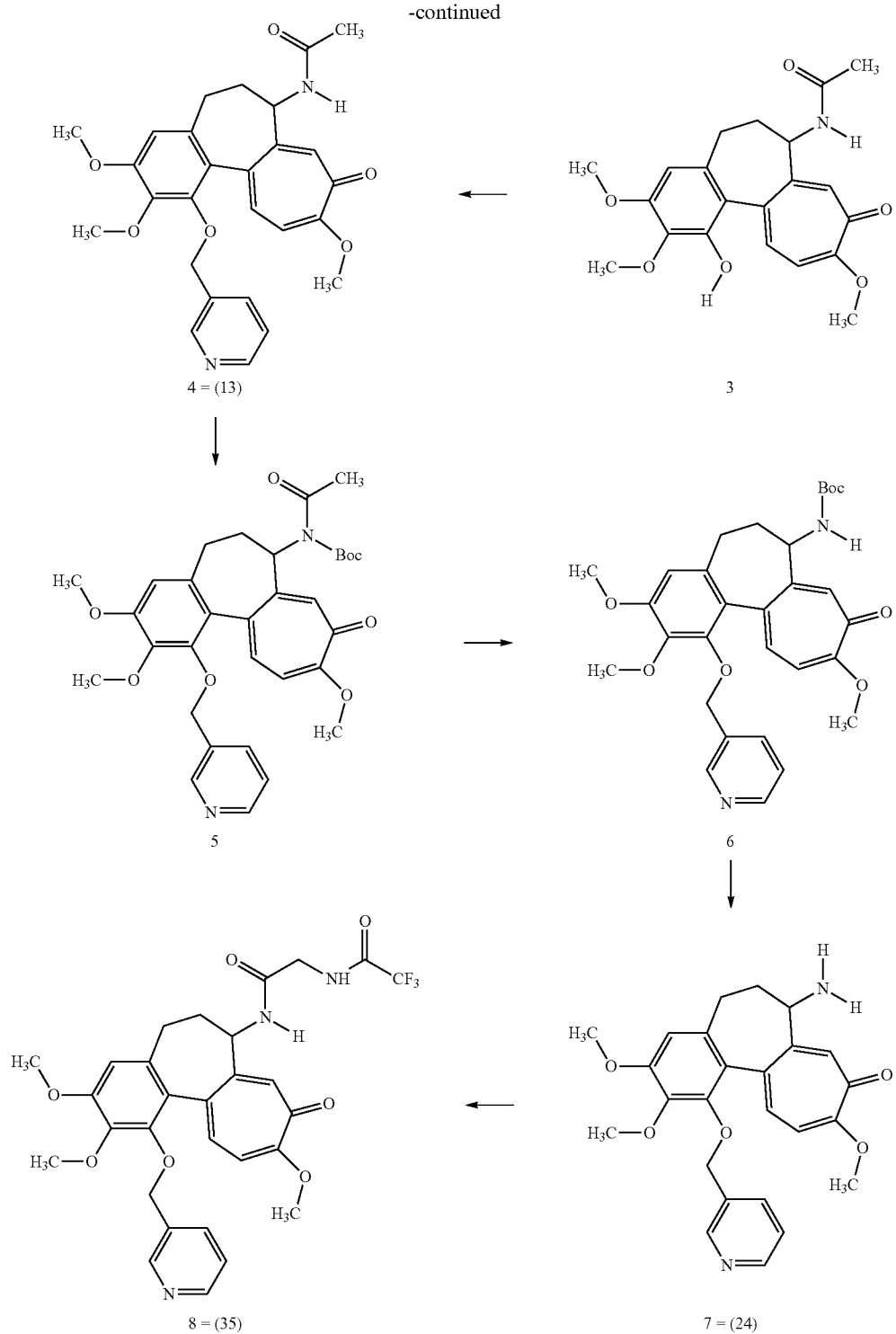

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (1.0 g, 2.6 mmol), 3-(chloromethyl)pyridine (0.64 g, 3.9 mmol) and potassium carbonate (1.08 g, 7.8 mmol) in DMF (20 mL) was stirred at 90° C. for 8 h. The reaction mixture was poured in water, extracted with ethyl acetate and concentrated to give the crude product. The crude product was purified by silica gel column chromatography to give the desired product (0.7 g, 58%).

A mixture of 4 (700 mg, 1.47 mmol), (Boc)2O (3.2 g, 14.71 mol) and DMAP (72 mg, 0.59 mmol) in THF (20 mL)

was refluxed overnight. The reaction mixture was washed with water, dried and concentrated to give the crude product which was purified by silica gel column chromatography to give the product (0.7 g, 87%).

A solution of 5 (0.7 g, 1.22 mmol) and sodium methoxide (131.0 mg, 2.43 mmol) in methanol (10 mL) was stirred at rt for 1 h. The reaction mixture was poured into water, extracted with dichloromethane, dried and concentrated to give the crude product which was used directly for the next step.

A solution of 6 (crude) and trifluoroacetic acid (10 mL) in dichloromethane (10 mL) stirred at rt for 2 hours. The reaction solution was concentrated to give the product (0.3 g).

A solution of 7 (50 mg, 0.13 mmol), EDCl (44 mg, 0.23 mmol), HOBT (31 mg, 0.23 mmol), F$_3$CGlyOH (39 mg, 0.23 mmol) and triethylamine (47 mg, 0.46 mmol) in dichloromethane (3 mL) was stirred at rt overnight. The reaction mixture was washed with water, dried and concentrated to give the crude product. The crude product was purified by chromatography to give the desired product (22 mg, 32%).

Compounds (40), (44) and (47)

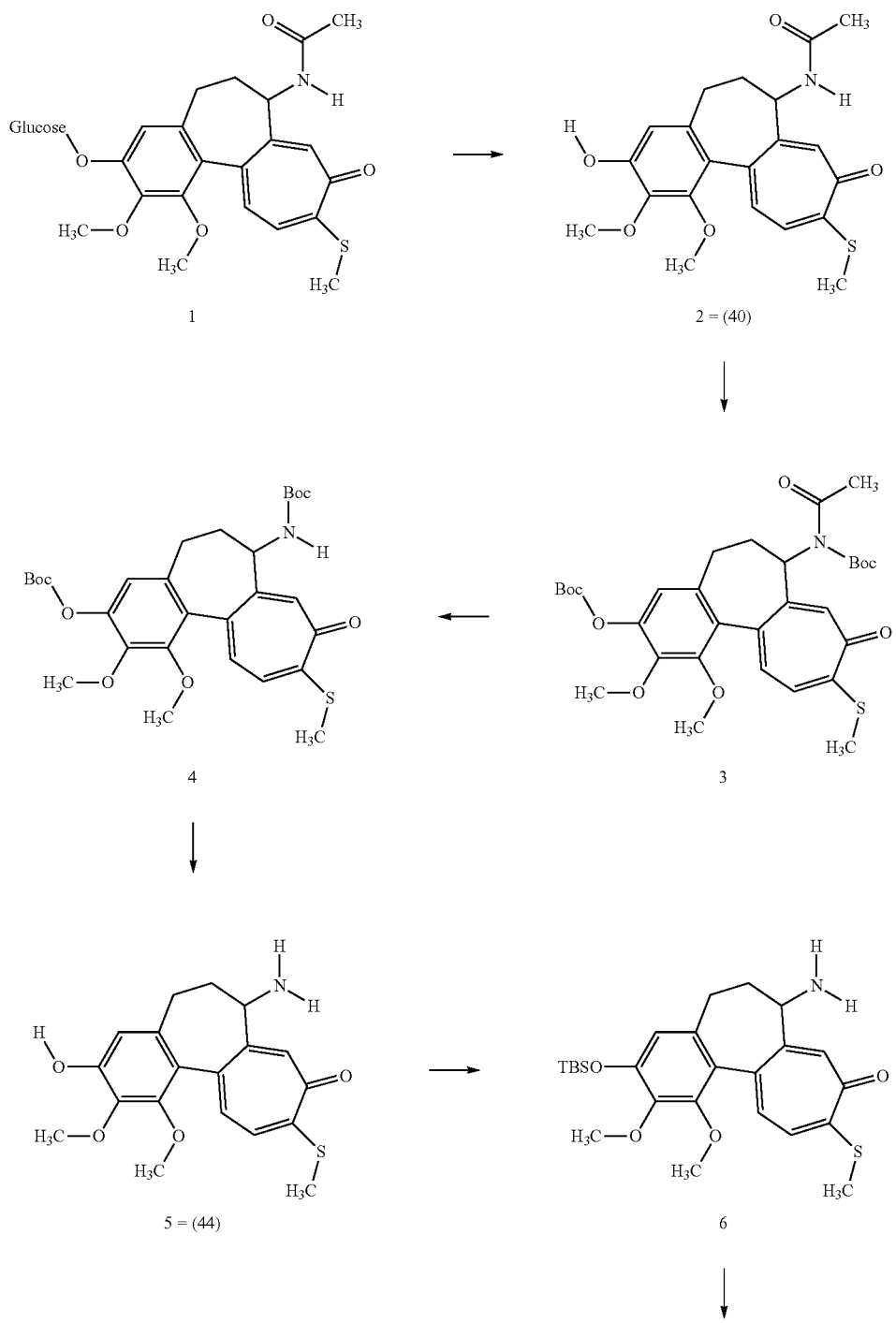

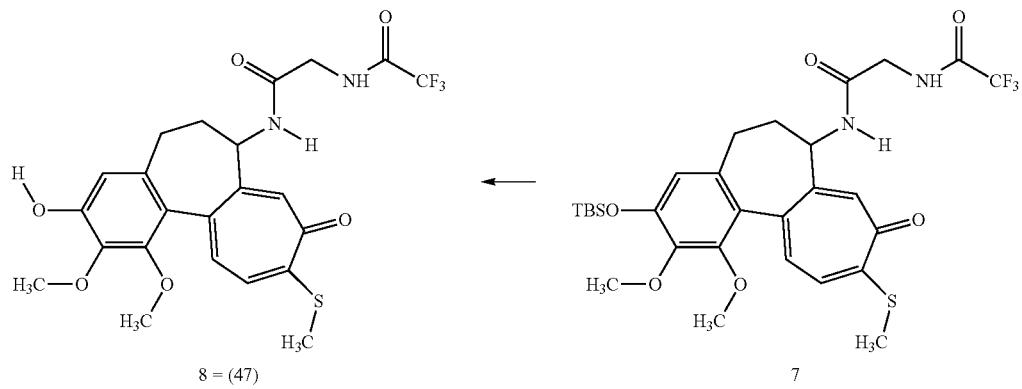

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallization with acetone to afford the title compound (1.8 g, 67%).

A mixture of 2 (600 mg, 1.50 mmol), (Boc)2O (3.3 g, 14.96 mmol) and DMAP (73 mg, 0.60 mmol) in THF (20 mL) was refluxed overnight. The reaction mixture was washed with water, dried and concentrated to give the crude product which was directly used for the next step.

A solution of 3 (crude) and sodium methoxide (120.0 mg, 2.3 mmol) in methanol (10 mL) was stirred at rt for 1 h. The reaction mixture was poured into water, extracted with dichloromethane, dried and concentrated to give the crude product which was used directly for the next step.

A solution of 4 (crude) and trifluoroacetic acid (10 mL) in dichloromethane (10 mL) was stirred at rt for 2 hours. The reaction solution was concentrated to give the product (0.4 g).

To a solution of 5 (50 mg, 0.14 mmol) and imidazole (9 mg, 0.14 mmol) in dichloromethane (3 mL) cooled to 0° C. was added tert-butyldimethylsilyl chloride (21 mg, 0.14 mmol). The resulting mixture was stirred at rt for 10 min. The reaction mixture was washed with water and concentrated to give the crude product. The crude product was purified by chromatography desired product (30 mg, 45%).

A solution of 6 (30 mg, 0.06 mmol), EDCl (24 mg, 0.13 mmol), HOBT (17 mg, 0.13 mmol), F₃CGlyOH (22 mg, 0.13 mmol) and triethylamine (26 mg, 0.26 mmol) in dichloromethane (3 mL) was stirred at rt overnight. The reaction mixture was washed with water, dried and concentrated to give the crude product which was directly used for the next step without further purification.

To a solution of 7 (crude) in THF (3 mL) was added TBAF (28 mg, 0.11 mmol). The resulting mixture was stirred at rt for 30 min. The reaction mixture was concentrated and purified by chromatography to give the desired product (20 mg).

Compounds (40), (41), (45) and (48)

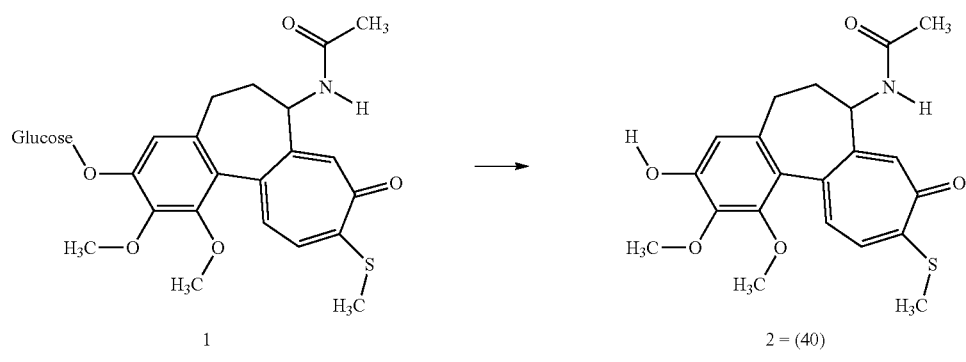

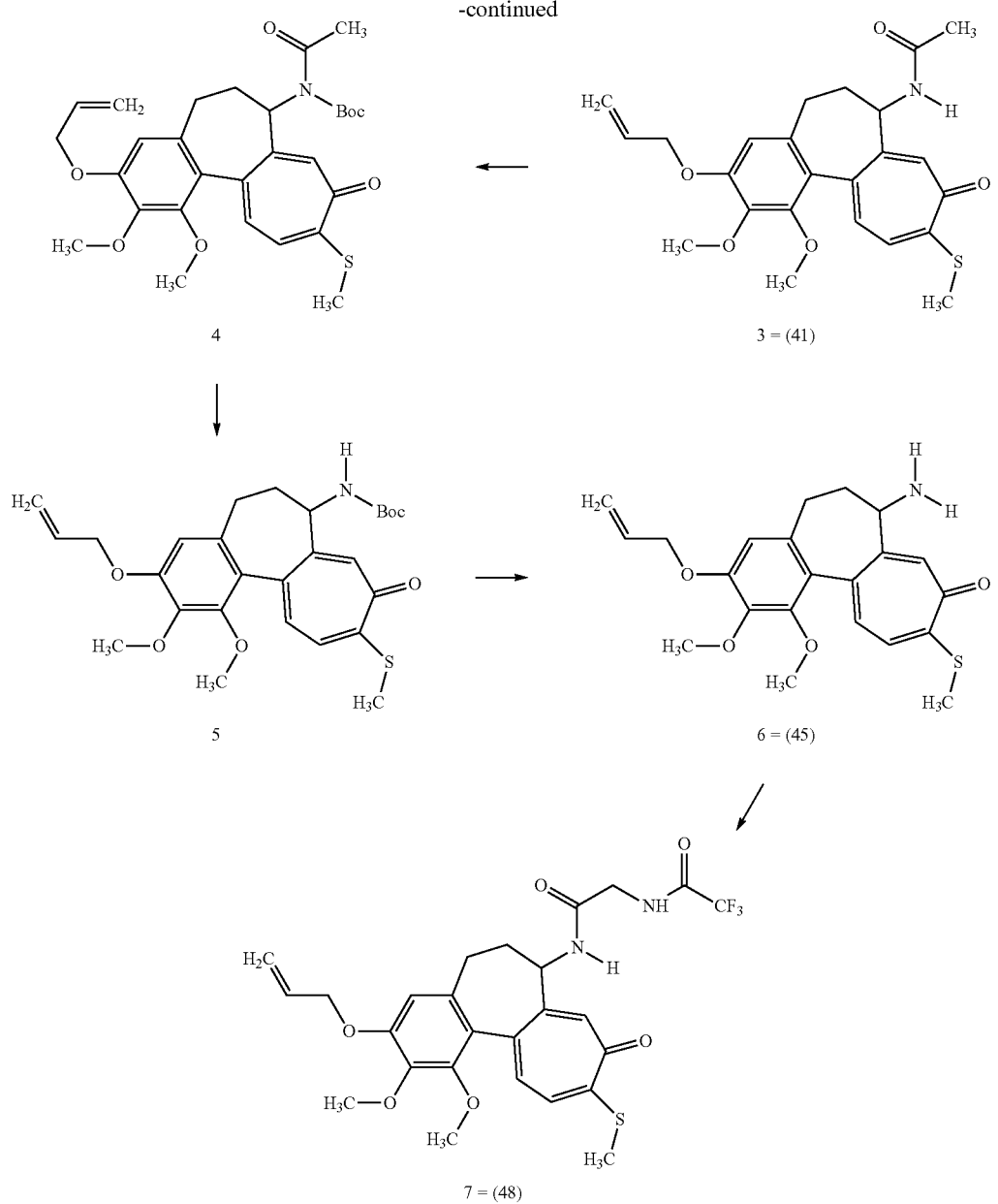

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallization with acetone to afford the title compound (1.8 g, 67%).

A mixture of 2 (50 mg, 0.12 mmol), 3-bromoprop-1-ene (23 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (30 mg, 55%).

A mixture of 3 (500 mg, 1.13 mmol), (Boc)2O (2.5 g, 11.31 mol) and DMAP (55 mg, 0.45 mmol) in THF (20 mL) was refluxed overnight. The reaction mixture was washed with water, dried and concentrated to give the crude product which was directly used for the next.

A solution of 4 (crude) and sodium methoxide (120.0 mg, 2.21 mmol) in methanol (10 mL) was stirred at rt for 1 h. The reaction mixture was poured into water, extracted with dichloromethane, dried and concentrated to give the crude product which was used directly for the next.

A solution of 5 (crude) and trifluoroacetic acid (10 mL) in dichloromethane (10 mL) was stirred at rt for 2 hours. The reaction solution was concentrated to give the product (0.4 g).

A solution of 6 (50 mg, 0.13 mmol), EDCl (48 mg, 0.25 mmol), HOBT (34 mg, 0.25 mmol), F₃CGlyOH (43 mg, 0.25 mmol) and triethylamine (63 mg, 0.63 mmol) in dichloromethane (3 mL) was stirred at rt overnight. The reaction mixture was washed with water, dried and concentrated to give the crude product. The crude product was purified by chromatography to give the desired product (25 mg, 36%).

Compounds (40), (42), (46) and (49)
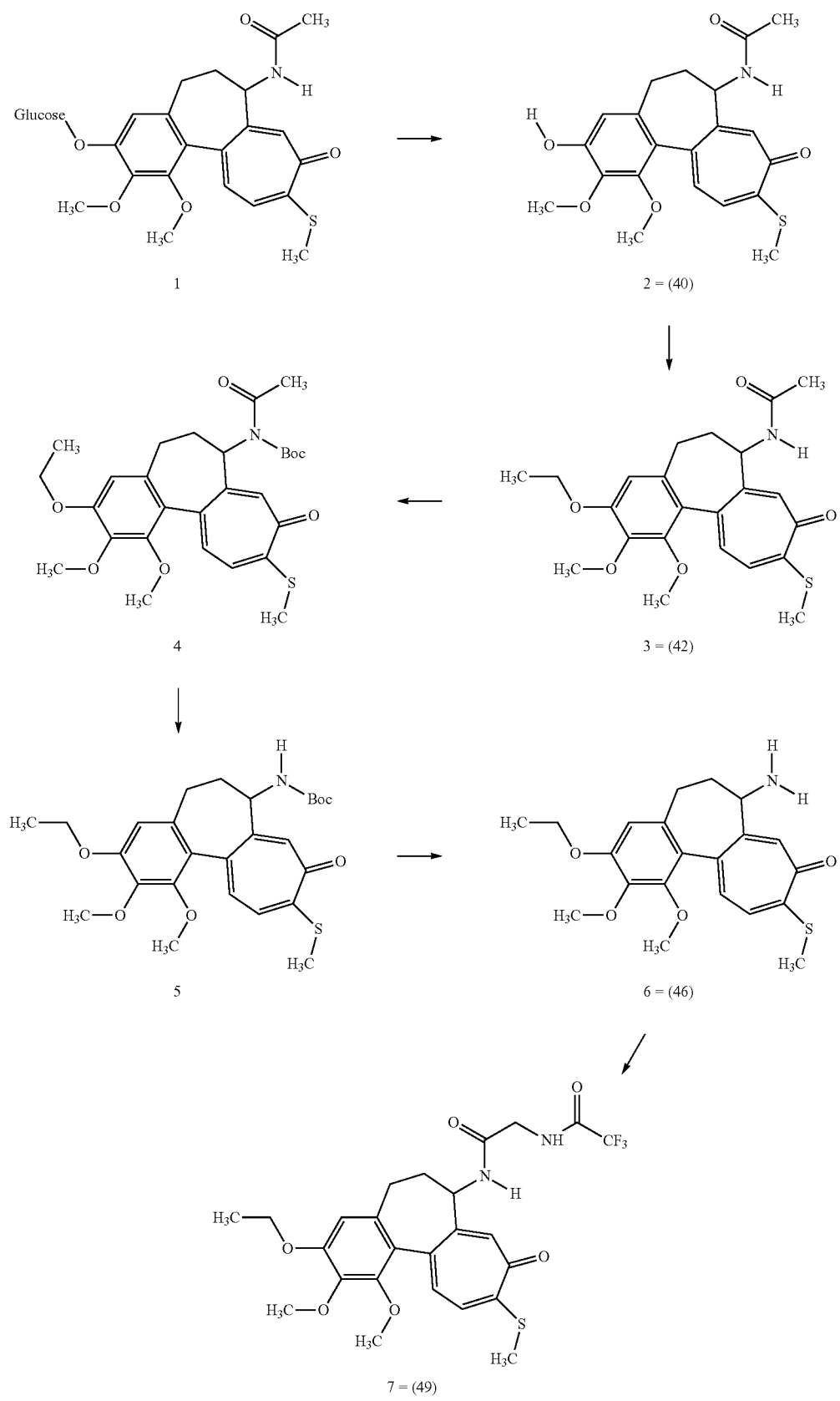

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (50 mg, 0.12 mmol), bromoethane (21 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (35 mg, 65%).

A mixture of 3 (500 mg, 1.16 mmol), (Boc)2O (2.5 g, 11.63 mol) and DMAP (57 mg, 0.47 mmol) in THF (20 mL) was refluxed overnight. The reaction mixture was washed with water, dried and concentrated to give the crude product which was directly used for the next step.

A solution of 4 (crude) and sodium methoxide (122.0 mg, 2.26 mmol) in methanol (10 mL) was stirred at rt for 1 h. The reaction mixture was poured into water, extracted with dichloromethane, dried and concentrated to give the crude product which was used directly for the next step.

A solution of 5 (crude) and trifluoroacetic acid (10 ml) in dichloromethane (10 mL) was stirred at rt for 2 hours. The reaction solution was concentrated to give the product (0.4 g).

A solution of 6 (50 mg, 0.13 mmol), EDCl (49 mg, 0.26 mmol), HOBT (35 mg, 0.26 mmol), F$_3$CGlyOH (44 mg, 0.26 mmol) and triethylamine (65 mg, 0.65 mmol) in dichloromethane (3 mL) was stirred at rt overnight. The reaction mixture was washed with water, dried and concentrated to give the crude product. The crude product was purified by chromatography to give the desired product (25 mg, 36%).

Compounds (6a), (17a) and (28a)

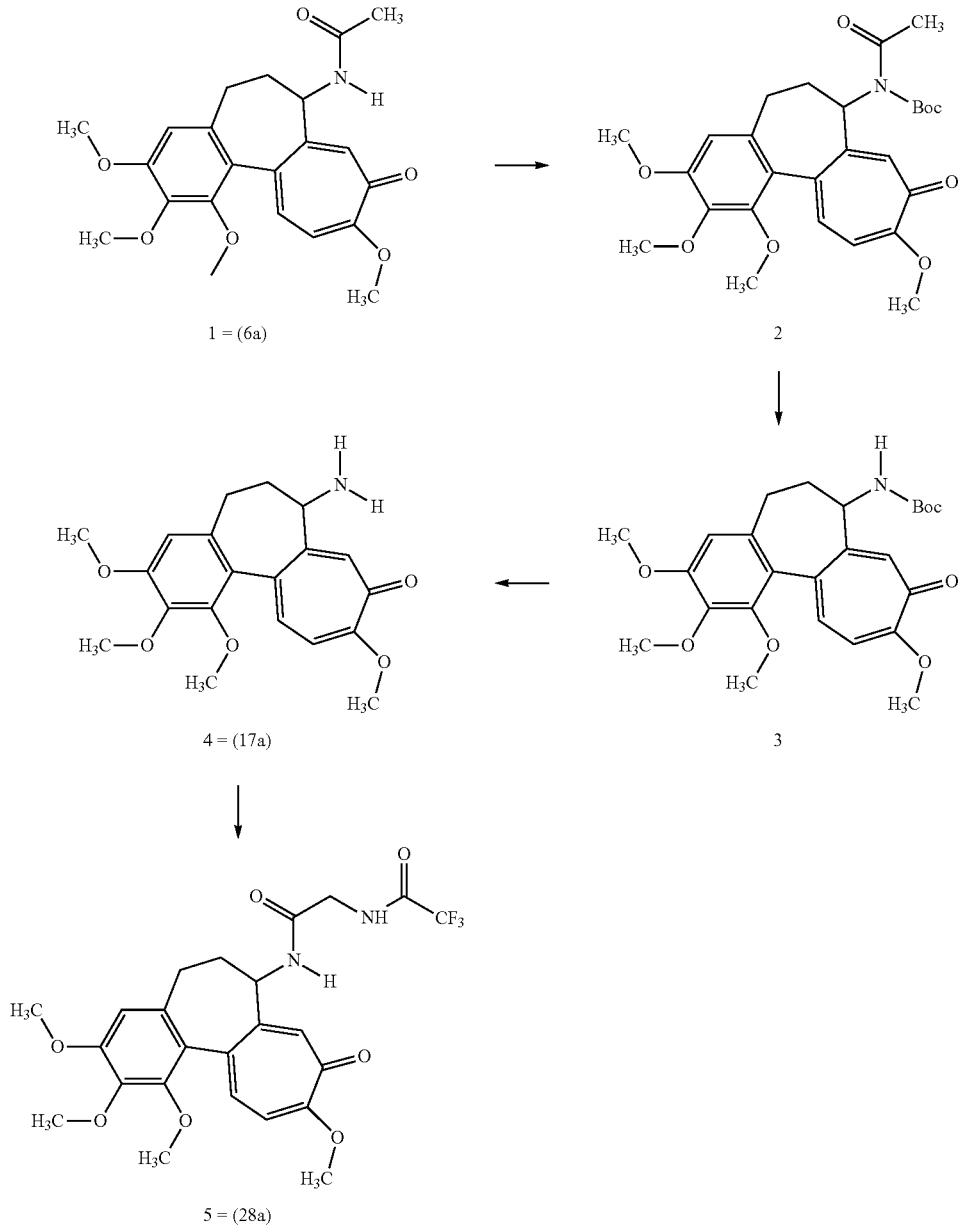

A mixture of 1 (20.0 g, 0.05 mmol), (Boc)2O (109.3 g, 0.50 mol) and DMAP (2.4 g, 0.02 mol) in THF (300 mL) was refluxed overnight. The reaction mixture was washed with water, dried and concentrated to give the crude product which was used directly to next step.

A solution of 2 (crude) and sodium methoxide (5.4 g, 0.1 mol) in methanol (400 mL) was stirred at rt for 2 h. Then water was added and extracted with dichloromethane. The extracts were concentrated to give the crude product which was purified by silica gel column chromatography (20.0 g, 87%).

A solution of 3 (2.95 g, 6.46 mmol) and trifluoroacetic acid (10 mL) in dichloromethane (10 mL) was stirred at rt for 3 hr. The reaction solution was concentrated to give the product (2.1 g, 91%).

A solution of 4 (200 mg, 0.56 mmol), DCC (138 mg, 0.67 mmol), DMAP (82 mg, 0.67 mmol), and triethylamine (115 mg, 1.12 mmol) in dichloromethane (5 mL) was stirred at rt overnight. The reaction mixture was washed with water and concentrated to give the crude product. The crude product was purified by silica gel column chromatography to give they desired product (110 mg, 39%).

Compound (83)

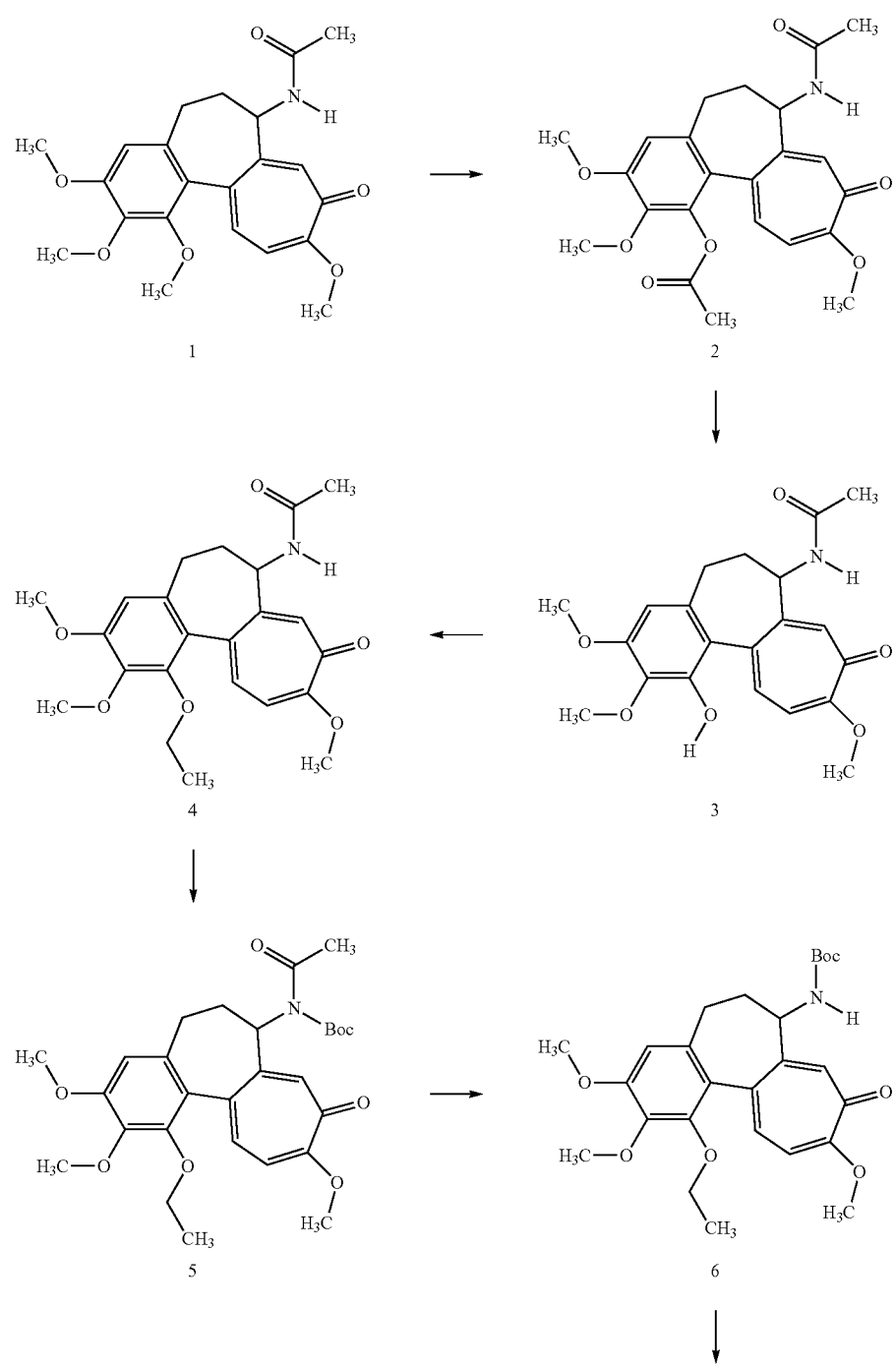

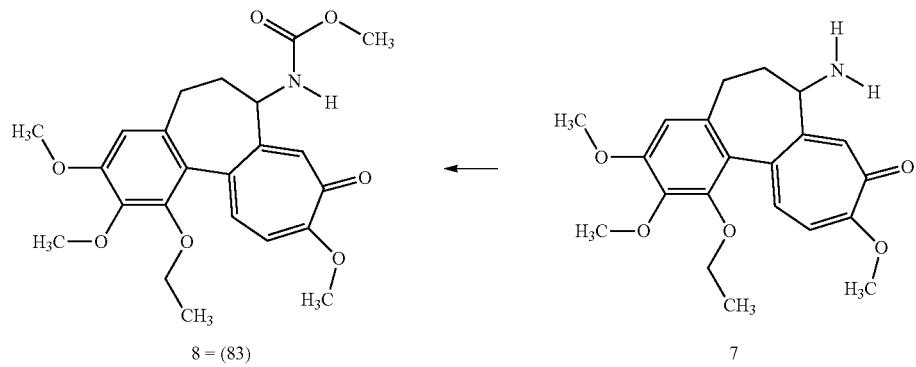

8 = (83)　　　　　7

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), bromoethane (450 mg, 4.16 mmol) and potassium carbonate (1150 mg, 8.31 mmol) in DMF (20 mL) was stirred at 90° C. for 2 h. The reaction mixture was poured in water, extracted with ethyl acetate and concentrated to give the crude product. The crude product was purified by silica gel column chromatography to give the desired product (0.5 g, 60%)

A mixture of 4 (700 mg, 1.69 mmol), (Boc)2O (3.7 g, 16.95 mol) and DMAP (83 mg, 0.68 mmol) in THF (15 mL) was refluxed overnight. The reaction mixture was washed with water, dried and concentrated to give the crude product which was used directly for the next step.

A solution of 5 (crude) and sodium methoxide (365.0 mg, 6.76 mmol) in methanol (15 mL) was stirred at rt for 2 h. Then water was added and extracted with dichloromethane. The extracts were concentrated to give the crude product. The crude product was purified by silica gel column chromatography to give the desired product (0.6 g).

A solution of 6 (600 mg, 1.27 mmol) and trifluoroacetic acid (5 mL) in dichloromethane (5 mL) was stirred at rt for 3 h. The reaction solution was concentrated to nine the product (0.45 g, 96%).

To a solution of 7 (50 mg, 0.13 mmol) and triethylamine (27 mg. 0.27 mmol) in dichloromethane (3 mL) was added methyl carbonochloridate (19 mg, 0.20 mmol) at 0° C. The resulting solution was stirred at rt for 1 h. The reaction mixture was washed with water and concentrated to give the crude product. The crude product was purified by chromatography to give the desired product (15 mg, 26%).

Compound (84)

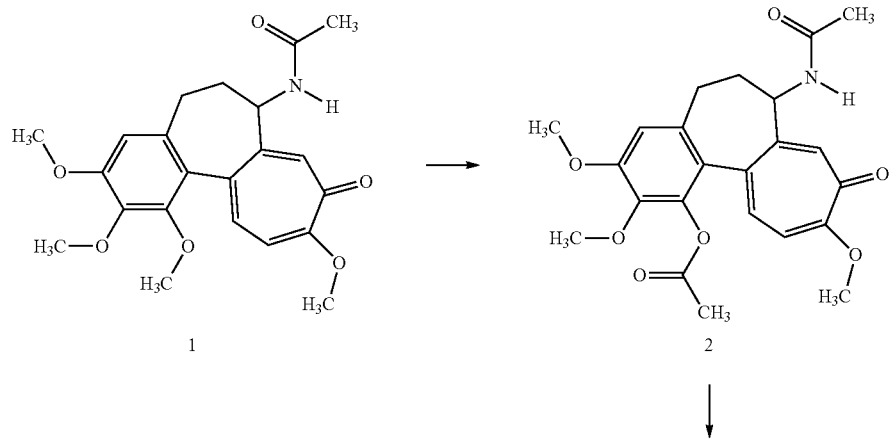

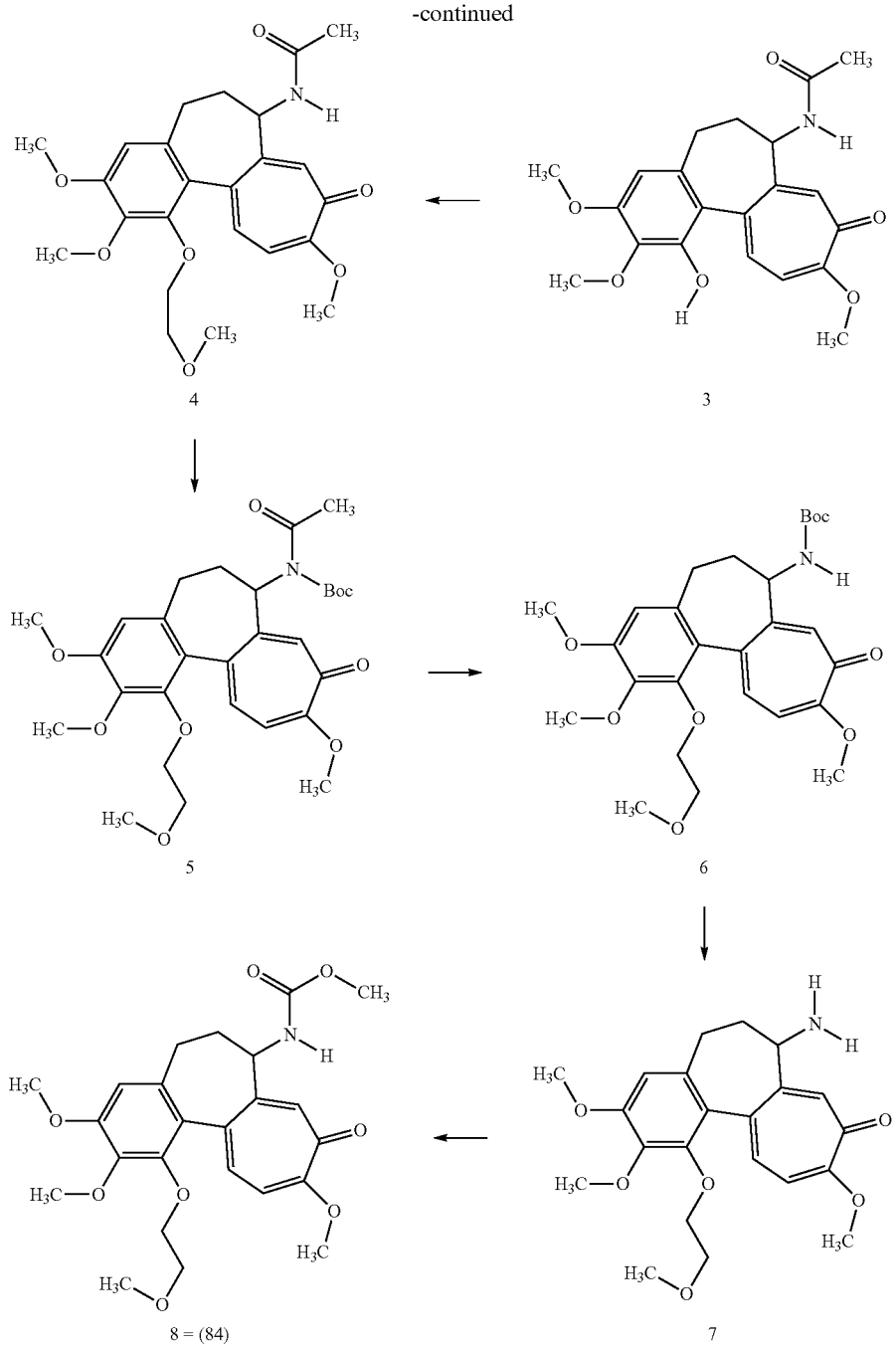

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stirred at rt for an hour. The aqueous phase was extracted and concentrated to give the crude product. The product was obtained by recrystallization (0.2 g, 21%, two steps).

A mixture of 3 (800 mg, 2.01 mmol), 1-bromo-2-methoxyethane (580 mg, 4.16 mmol) and potassium carbonate (1.15 g, 8.31 mmol) in DMF (20 mL) was stirred at 75° C. for 3 h. The reaction mixture was poured in water, extracted with ethyl acetate and concentrated to give the crude product. The crude product was purified by silica gel column chromatography to give the desired product (0.5 g, 54%)

A mixture of 4 (500 mg, 1.13 mmol), (Boc)2O (2.5 g, 11.29 mmol) and DMAP (55 mg, 0.45 mmol) in THF (10 mL) was refluxed overnight. The reaction mixture was washed with water, dried and concentrated to give the crude product which was used directly for the next step.

A solution of 5 (crude) and sodium methoxide (244.0 mg, 4.52 mmol) in methanol (15 mL) was stirred at rt for 2 h. Then water was added and extracted with dichloromethane. The extracts were concentrated to give the crude product. The crude product was purified by silica gel column chromatography to give the desired product (0.4 g).

A solution of 6 (0.6 g, 1.20 mmol) and trifluoroacetic acid (5 ml) in dichloromethane (5 mL) was stirred at rt for 3 hours. The reaction solution was concentrated to give the product (0.45 g, 94%).

To a solution of 7 (50 mg, 0.12 mmol) and triethylamine (25 mg, 0.25 mmol) in dichloromethane (3 mL) was added methyl carbonochloridate (18 mg, 0.19 mmol) at 0° C. The resulting solution was stirred at rt for 1 h. The reaction mixture was washed with water and concentrated to give the crude product. The crude product was purified by chromatography to give the desired product (16 mg, 28%).

Compound (85)

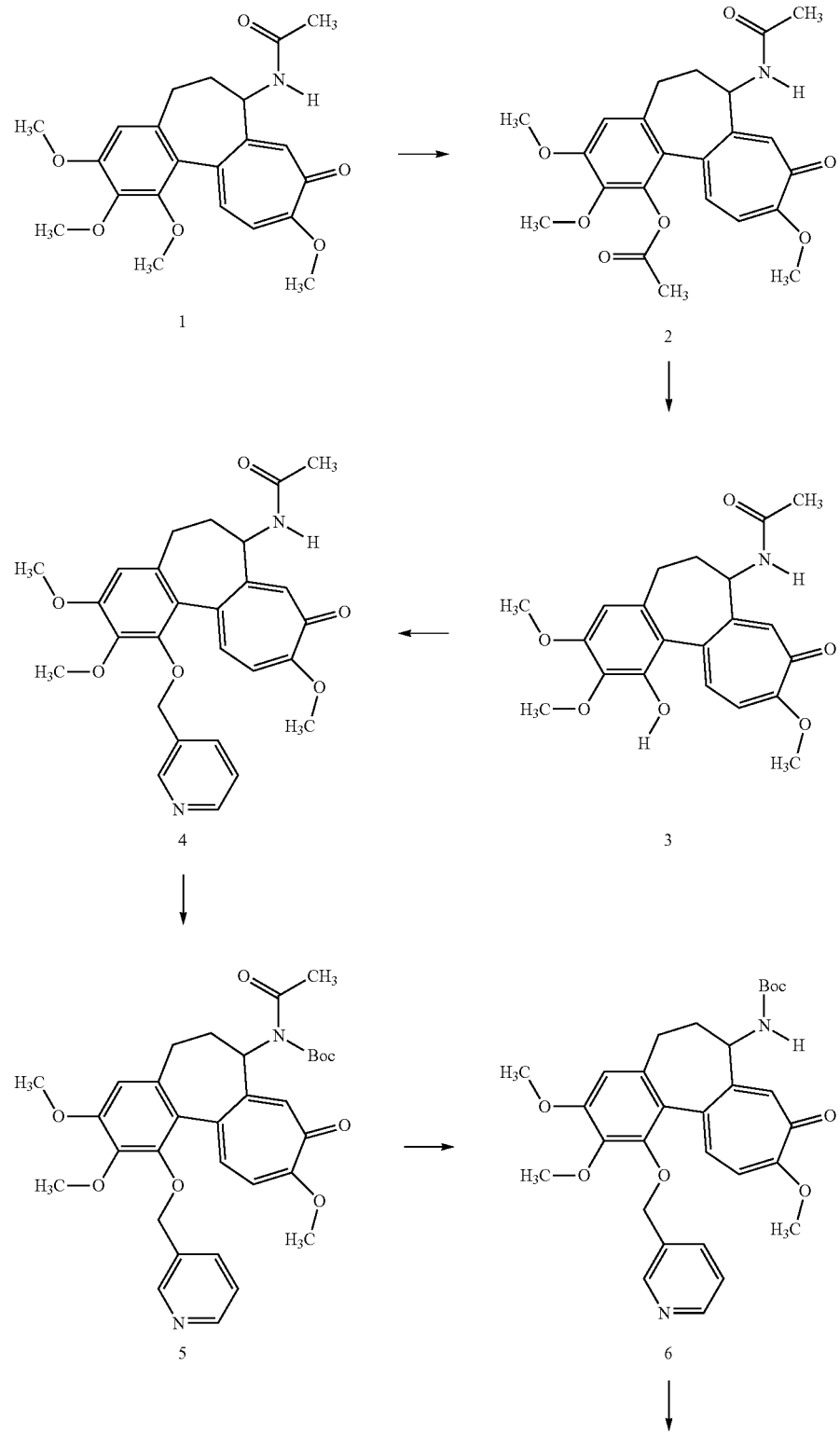 [SMILES: COc1cc2c(c(OC)c1OC)-c1ccc(OC)c(=O)cc1C(NC(C)=O)CC2 ; COc1cc2c(c(OC(C)=O)c1OC)-c1ccc(OC)c(=O)cc1C(NC(C)=O)CC2 ; COc1cc2c(c(OCc3cccnc3)c1OC)-c1ccc(OC)c(=O)cc1C(NC(C)=O)CC2 ; COc1cc2c(c(O)c1OC)-c1ccc(OC)c(=O)cc1C(NC(C)=O)CC2 ; COc1cc2c(c(OCc3cccnc3)c1OC)-c1ccc(OC)c(=O)cc1C(N(C(C)=O)C(=O)OC(C)(C)C)CC2 ; COc1cc2c(c(OCc3cccnc3)c1OC)-c1ccc(OC)c(=O)cc1C(NC(=O)OC(C)(C)C)CC2]

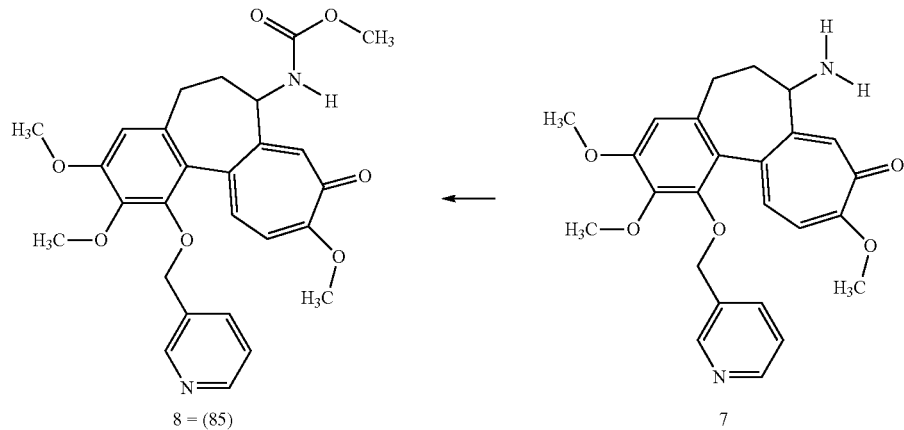

8 = (85)         7

To a solution of 1 (1.0 g, 2.51 mmol), and acetyl chloride (3 mL) was added in tetrachloride (1 mL), and the mixture was stirred at rt for 40 h. The crude product was directly used for the next step.

A solution of 2 (crude) and lithium hydroxide (4 eq.) in methanol/water was stored at rt for an hour. The aqueous phase was extracted and concentrated to give the crude product. The product was obtained by recrystallization (0.2 g, 21%, two steps).

A mixture of 3 (1.0 g, 2.6 mmol), 3-(chloromethyl) pyridine (0.64 g, 3.9 mmol) and potassium carbonate (1.08 g, 7.8 mmol) in DMF (20 mL) was stared at 90° C. for 8 h. The reaction mixture was poured in water, extracted with ethyl acetate and concentrated to give the crude product. The crude product was purified by silica gel column chromatography to give the desired product (0.7 g, 58%)

A mixture of 4 (700 mg, 1.47 mmol), (Boc)2O (3.2 g, 14.71 mol) and DN P (72 neg. 0.59 mmol) in THF (20 mL) was refluxed overnight. The reaction mixture was washed with water. dried and concentrated to give the crude product which was purified by silica gel column, chromatography to give the product (0.7 g, 87%).

A solution of 5 (0.7 g, 1.22 mmol) and sodium methoxide (131.0 mg, 2.43 mmol) in methanol (10 mL) was stirred at it for 1 h. The reaction mixture was poured into water, extracted with dichloromethane, dried and concentrated to give the crude product which was used directly for the next step.

A solution of 6 (crude) and trifluoroacetic acid (10 ml) in dichloromethane (10 mL) was stirred at it for 2 hours. The reaction solution was concentrated to give the product (0.3 g).

To a solution of 7 (50 mg, 0.12 mmol) and triethylamine (35 mg, 0.35 mmol) in dichloromethane (3 mL) was added methyl carbonochloridate (16 mg, 0.17 mmol) at 0° C. The resulting solution was stirred at it for 1 h. The reaction mixture was washed with water and concentrated to give the crude product. The crude product was purified by chromatography to give the desired product (12 mg, 21%).

Compound (89)

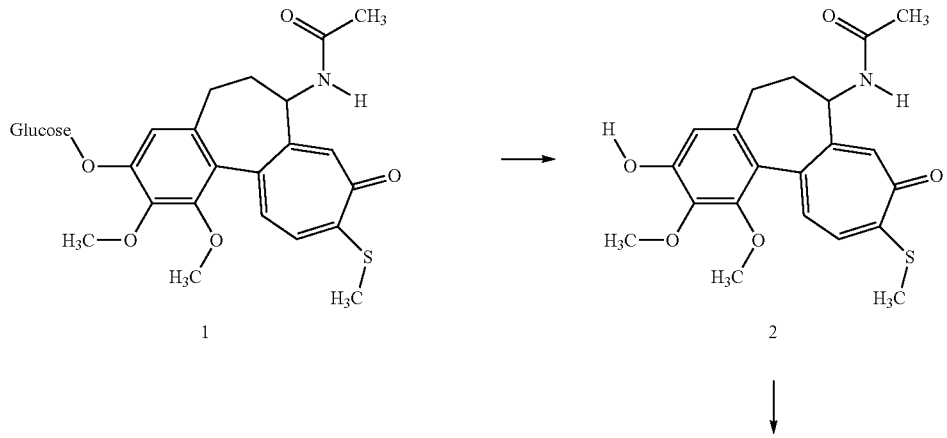

1         2

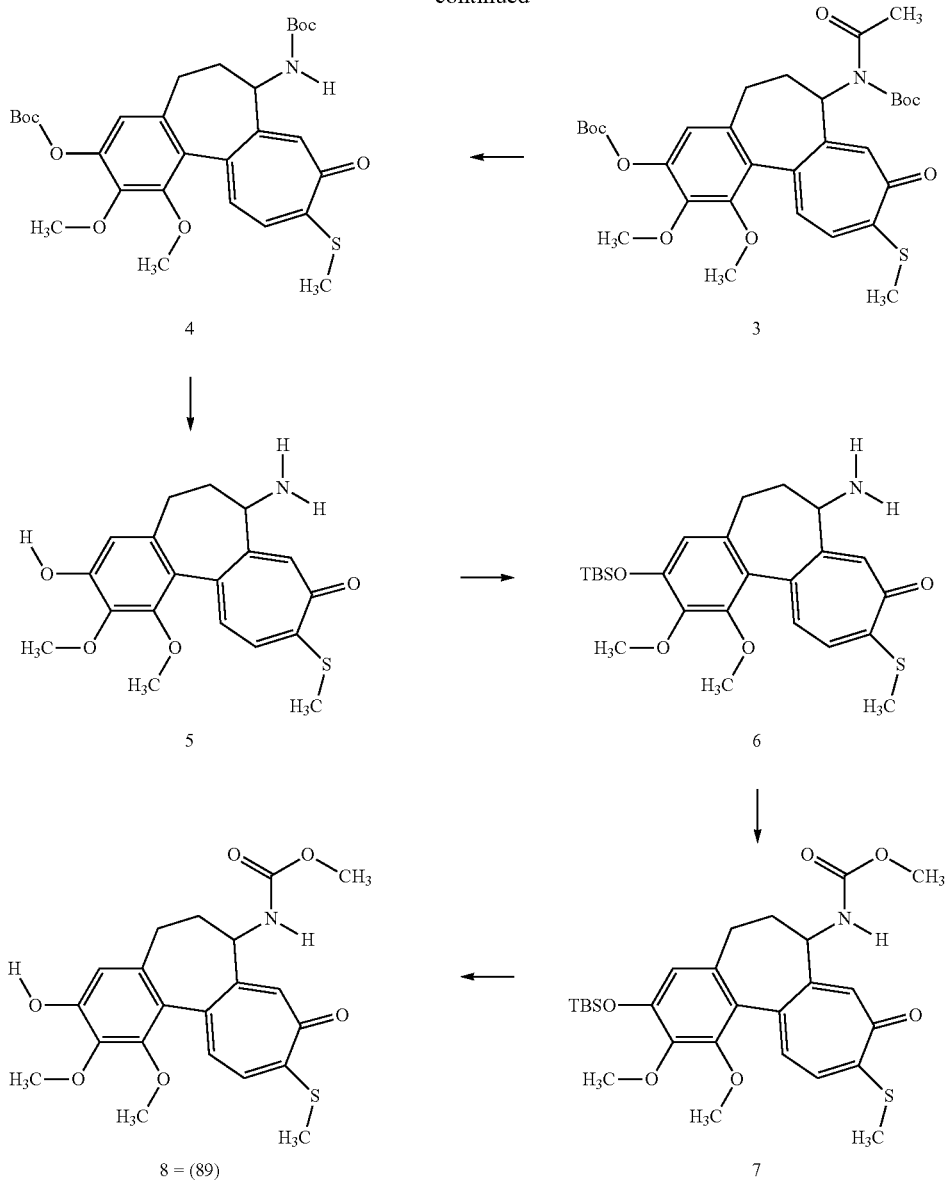

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (600 mg, 1.50 mmol), (Boc)2O (3.3 g, 14.96 mmol) and DMAP (73 mg, 0.60 mmol) in THF (20 mL) was refluxed overnight. The reaction mixture was washed with water, dried and concentrated to give the crude product which was directly used for the next.

A solution of 3 (crude) and sodium methoxide (120.0 mg, 2.3 mmol) in methanol (10 mL) was stirred at rt for 1 h. The reaction mixture was poured into water, extracted with dichloromethane, dried and concentrated to give the crude product which was used directly for the next.

A solution of 4 (crude) and trifluoroacetic acid (10 mL) in dichloromethane (10 mL) was stirred at rt for 2 hours. The reaction solution was concentrated to give the product (0.4 g).

To a solution of 5 (50 mg, 0.14 mmol) and Im (9 mg, 0.14 mmol) in dichloromethane (3 mL) cooled to 0° C. was added tert-butyldimethylchlorosilane (21 mg, 0.14 mmol). The resulting mixture was stirred at rt for 10 min. The reaction mixture was washed with water and concentrated to give the crude product. The crude product was purified by chromatography to give the desired product (30 mg, 45%).

To a solution of 6 (100 mg, 0.13 mmol) and triethylamine (64 mg, 0.64 mmol) in dichloromethane (3 mL) was added methyl carbonochloridate (40 mg, 0.42 mmol) at 0° C. The resulting solution was stirred at rt for 1 h. The reaction mixture was washed with water and concentrated to give the crude product. The crude product was purified by chromatography to give the desired product (50 mg, 45%).

To a solution of 7 (50 mg, 0.09 mmol) in tetrahydrofuran (3 mL) was added TBAF (29 mg, 0.11 mmol). The resulting mixture was stirred at rt for 30 min. The reaction mixture was concentrated and purified by chromatography to give the desired product (20 mg, 51%).

Compound 90
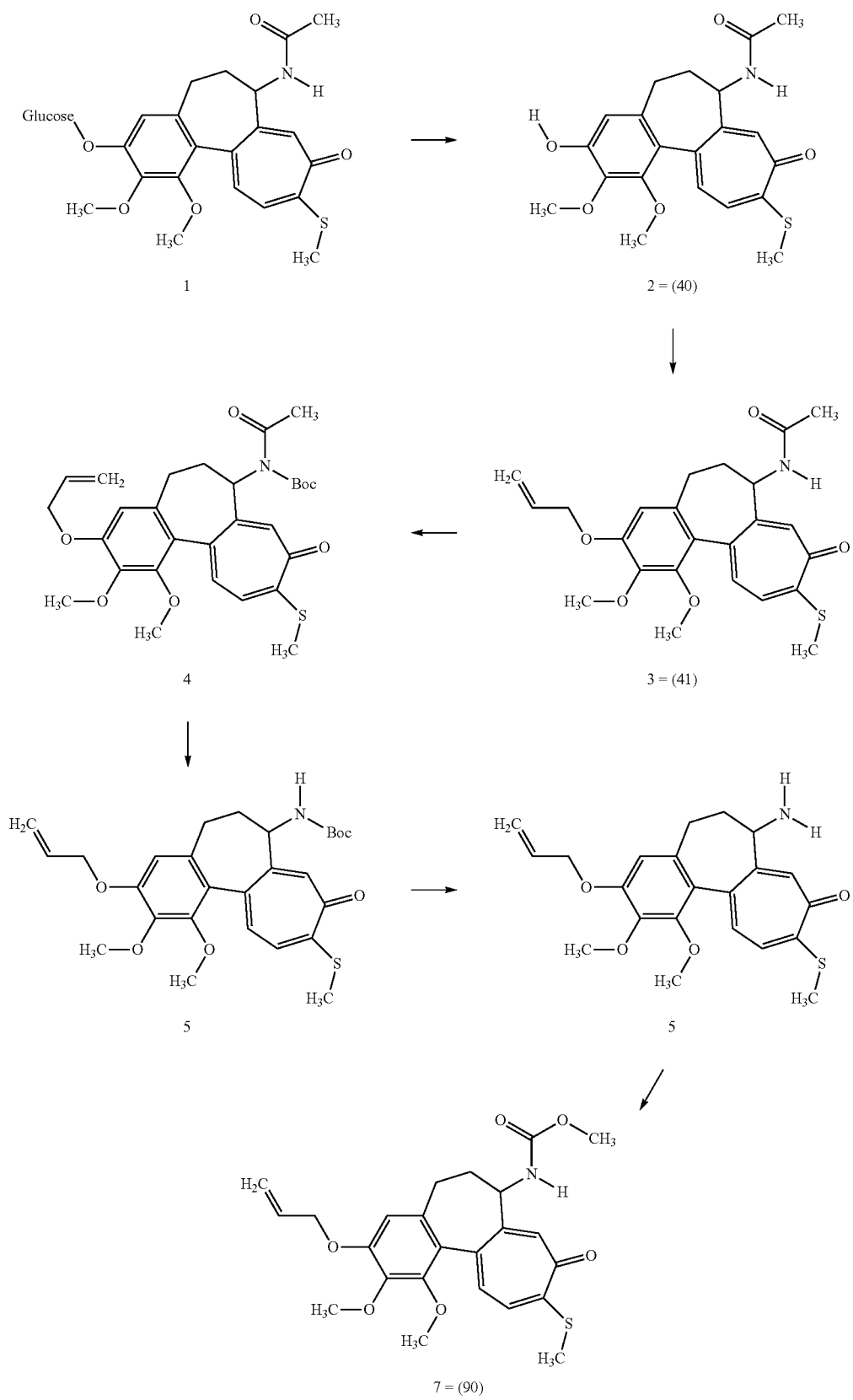

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (50 mg, 0.12 mmol), 3-bromoprop-1-ene (23 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (30 mg, 55%).

A mixture of 3 (500 mg, 1.13 mmol), (Boc)2O (2.5 g, 11.31 mol) and DMAP (55 mg, 0.45 mmol) in THF (20 mL) was refluxed overnight. The reaction mixture was washed with water, dried and concentrated to give the crude product which was directly used for the next step.

A solution of 4 (crude) and sodium methoxide (120.0 mg, 2.21 mmol) in methanol (10 mL) was stirred at rt for 1 h. The reaction mixture was poured into water, extracted with dichloromethane, dried and concentrated to give the crude product which was used directly for the next step.

A solution of 5 (crude) and trifluoroacetic acid (10 mL) in dichloromethane (10 mL) was stirred at rt for 2 hours. The reaction solution was concentrated to give the product (04 g).

To a solution of 6 (50 mg, 0.13 mmol) and triethylamine (25 mg, 0.25 mmol) in dichloromethane (3 mL) was added methylcarbonochloridate (24 mg, 0.25 mmol) at 0° C. The resulting solution was stirred at rt for 1 h. The reaction mixture was washed with water and concentrated to give the crude product. The crude product was purified by chromatography to give the desired product (20 mg, 35%).

Compound (91)

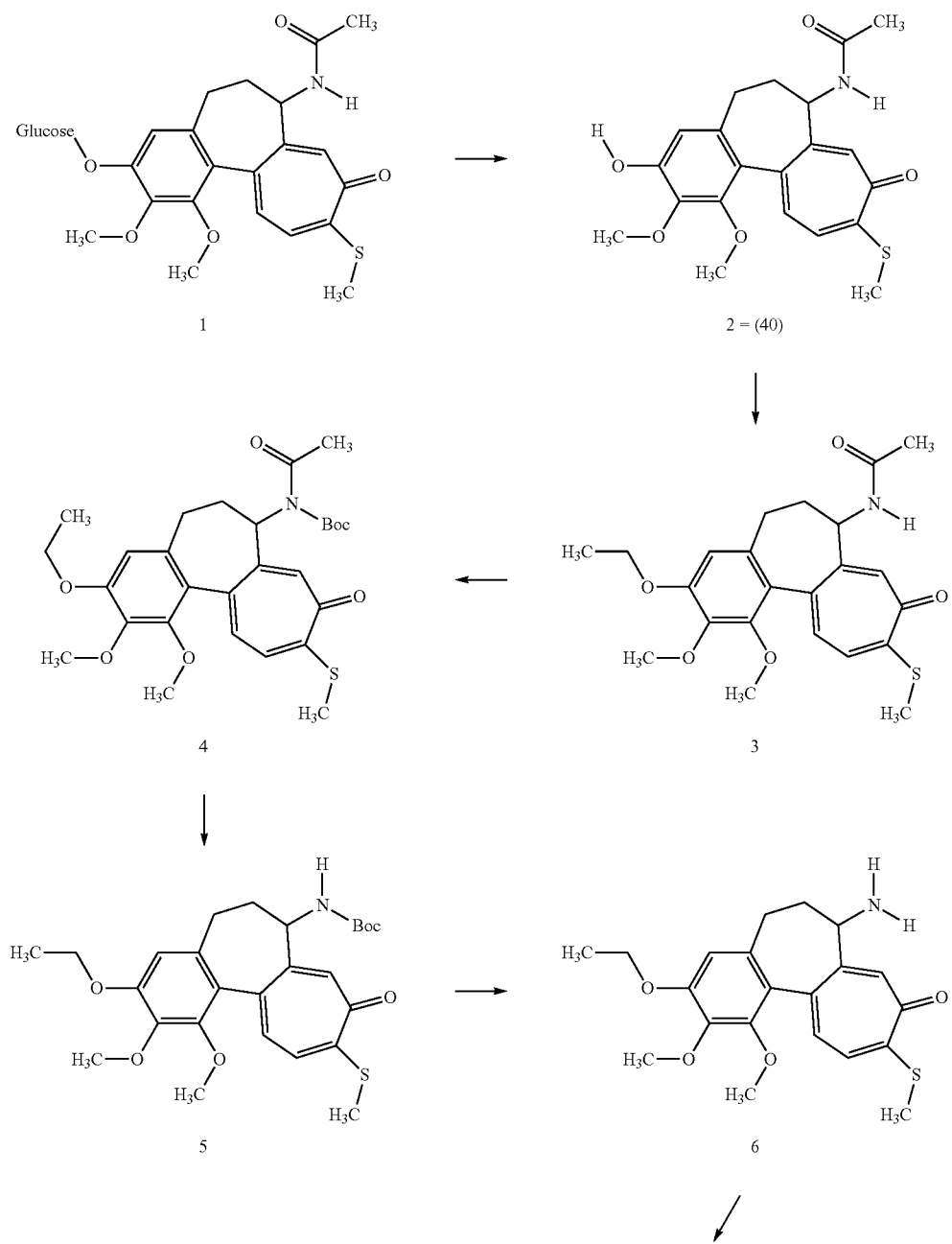

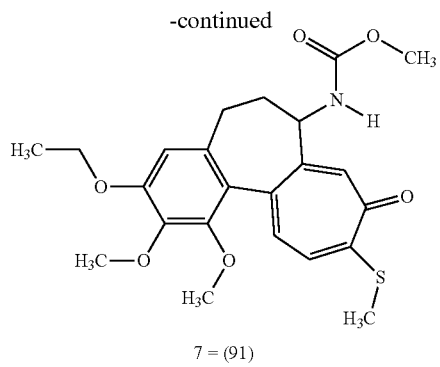

7 = (91)

A mixture of 1 (4.0 g) in phosphoric acid (120 mL) was stirred at rt overnight. The mixture was poured on ice, adjusted to pH 5 by the addition of 15% aq. sodium hydroxide, followed by several extractions with dichloromethane. The combined organic layers were concentrated to give the crude product. The crude product was purified by crystallized with acetone to afford the title compound (1.8 g, 67%).

A mixture of 2 (50 mg, 0.12 mmol), bromoethane (21 mg, 0.19 mmol) and potassium carbonate (52 mg, 0.37 mmol) in acetone (3 mL) was refluxed for 2 h. The reaction mixture was filtered and the filtrate was concentrated to give the crude product. The crude product was purified by chromatography to give the desired product (35 mg, 65%).

A mixture of 3 (500 mg, 1.16 mmol), (Boc)2O (2.5 g, 11.63 mol) and DMAP (57 mg, 0.47 mmol) in THF (20 mL) was refluxed overnight. The reaction mixture was washed with water, dried and concentrated to give the crude product which was directly used for the next step.

A solution of 4 (crude) and sodium methoxide (122.0 mg, 2.26 mmol) in methanol (10 mL) was stirred at rt for 1 h. The reaction mixture was poured into water, extracted with dichloromethane, dried and concentrated to give the crude product which was used directly for the next step.

A solution of 5 (crude) and triethylamine (10 mL) in dichloromethane (10 mL) was stirred at rt for 2 hours. The reaction solution was concentrated to give the product (0.4 g).

To a solution of 6 (50 mg, 0.13 mmol) and triethylamine (25 mg, 0.25 mmol) in dichloromethane (3 mL) was added methyl carbonochloridate (24 mg, 0.25 mmol) at 0° C. The resulting solution was stirred at rt for 1 h. The reaction mixture was washed with water and concentrated to give the crude product. The crude product was purified by chromatography to give the desired product (20 mg, 35%).

CEM Cell Growth and Treatment with Colchicine Compounds (2-16 and 28-38)

Preparation of Media with Colchicine Derivatives (2-16) and (28-38)

The colchicine derivatives (2-16) and (28-38) treated media were prepared using: 1 nM, 10 nM, 20 nM, 100 nM, 500 nM and 1000 nM of (2-16) or (28-38) placed in a 1.5 mL glass vials and dissolved in 10 μL of dimethyl sulfoxide. Dimethyl sulfoxide was the solvent for the (2-16) and (28-38) derivatives. Once dissolved, the dimethyl sulfoxide (2-16) and dimethyl sulfoxide (28-38) mixtures were added to the media and incubated overnight in 37° C. No decrease in the growth of cells placed in 10 μL of dimethyl sulfoxide only was observed.

Cell Cultures

CEM cells (American Type Culture Collection, Manassas, Va.) were maintained in tissue culture flasks and cultured as monolayer in 20 mL of RPMI media containing 10% Fetal Bovine Serum (FBS). When the number of cells in the culture flask reached 5-6×10$^6$ cells/mL the culture was harvested and then inoculated into six Hollow Fiber Bioreactors (HFB, FiberCells System, Frederick, Md.) and were continuously cultured in 37° C. and 5% $CO_2$. HFB consists of a single, hydrophilic and polysulfone fiber with 0.1 μm diameter pores. The media circulating within the HFB cartridge and polysulphone tubing, at flow rate of 14 mL/min, brings oxygen and nutrients to cells and removes $CO_2$ and other waste. Collagen solution was used to create an extra cellular matrix between the cells and the fiber. The polysulphone fiber was coated with protein by flushing with 10 mL of coating solution containing 1 mg collagen per 1 mL Phosphate Buffered Saline (PBS). The pH was maintained in the extra-capillary space throughout the duration of experiments between 6.8 and 7.0. Due to the perfusion the HFB absorbed sufficient oxygen from the reservoir with fresh media to keep cells alive. The perfusion medium was changed weekly when the glucose level reached 2 g/L measured with a glucometer. The oxygen concentration in 100 mL of media was 7.6 μg/mL, due to its solubility at 37° C.

Viability of Cells

Viability was assessed using trypan blue (K. Takahashi, G. Loo, Biochem. Pharm. 67 (2004) 315-324). Briefly, CEM cells were harvested from HFB, seeded in 6 well microplates and exposed to 0.4% (w/v) trypan blue dye solution. Cell number was determined manually with a hemacytometer chamber (Hausser Scientific, Horsham, Pa.).

Treatment of Cells

Approximately 4×10$^4$ CEM cells/ml were treated on culture plates and placed for the 72 h incubation with (2-16) and (28-38) derivatives. All compounds were used for in vitro experiments and then the derivatives were selected for HFB studies to treat 10$^9$ CEM cells/mL in the 3-D cultures. The cells were treated 4 weeks after the cells' inoculation in the HFB. After 72 h, the growth was inhibited over 50% for 20 nM and higher concentrations in cells treated with (6), (13), (28) and (35).

MRI

All MRI experiments were performed using a 9.4 Tesla with 21 cm bore magnet (Magnex, U.K.) and TMX console (NRC-IBD, Canada). $^{19}$F MR images were acquired using double ($^{19}$F and $^1$H) tuned transmit/receive radio frequency (RF) volume coil operating at 376 MHz and 400 MHz corresponding to $^{19}$F and $^1$H Larmour frequency at 9.4 Tesla, respectively. $^1$H MR images were collected in the same imaging session that $^{19}$F MRI. Proton MR provided anatomical images of the culture. The MRI images monitored the localization of cells around the fiber in HFB as well as the volume of the cells. Moreover, $^{19}$F MRI selectively visualizes only intracellular fluorine uptake with no background, therefore allows cell count. The cells before and after treatment with (6), (13), (28) and (35) were imaged with $^1$H MRI, this allowed changes to be observed in the 3-D cell aggregation. The cells treated with 20 nM (28) and (35) were also imaged with $^{19}$F MRI to measure fluorine content using $^{19}$F NMR signal intensity (SI) in each HFB treated with (28) and (35). Using the calibration curves for $^{19}$F SI values we estimated the number of CEM cells labeled with $^{19}$F-derivatives of colchicine. To obtain the calibration curves (for each derivative separately) the phantoms consisting of HFB tubes filled with 1 nM, 10 nM, 20 nM, 100 nM, 500 nM and 1000 nM of (28) or (35) and $10^3$ cells, $10^4$ cells, $10^5$ cells, $10^6$ cells, $10^7$ cells, $10^8$ cells and $10^9$ cells were used. The linear regression was used to find the SI dependence on cell numbers. The cell numbers estimated from $^{19}$F MR imaging were compared to the cell viability obtained from trypan blue assays. For $^1$H MRI, a spin echo pulse sequence was used with Time to Echo (TE)/Time to repetition (TR)=16.5/5000 ms. For $^{19}$F MR imaging Inversion Recovery (IR) spin-echo method with Inversion Time (IT) of 400 ms and TE/TR=16.5/5000 ms was used. One 1 mm slice was acquired with a matrix size of 256×256 and a field of view of 3×3 cm for both $^{19}$F and $^1$H. Viability assessed by trypan blue showed viable cells, while $^{19}$F SI counted nonviable cells with intracellular uptake of the fluorine derivatives of colchicine. Moreover, $^{19}$F MR images showed distribution of derivatives in cell cultures.

HPLC-UV

Digested cell samples were fractionated with a Gold HPLC chromatograph system equipped with a Gold 166 Ultra Violet (UV) Detector and 32-Karat software (Beckman-Coulter, Mississauga, ON, Canada). For reversed-phase HPLC, a Vydac 218 TP54 Protein & Peptide C18 analytical column, 300 Å pore size, 0.46 cm×25 cm (Separation Group, Hesperia, Calif., U.S.A.) was used. The chromatograph was equipped with a Rheodyne injector (5 μL). UV detection was performed at 245 nm. Eluent A consisted of 5% acetonitrile (ACN) water solution and eluent B of 0.01% trifluoroacetic acid in 95% ACN water solution. A linear gradient from 5 to 70% ACN was applied over 60 min.

Statistical Analysis

Results were expressed as a mean±SD. Differences between groups at each time-point were identified by one-way Anova. Statistical comparison between two independent variables was determined by two-way Anova with Dunnet's correction performed post-hoc to correct multiple comparisons. The p-values <0.05 were considered statistically significant. All data reported here are from sets of 3 separate experiments. Error bars in all graphs represents the standard error of the mean. Data were analyzed using the Sigma Stat Soft (Chicago, Ill.) software.

Results

Colchicine analogues synthesized and tested for their ability to inhibit cell growth ex vivo were separated into three groups presented in FIGS. 1 to 3 according to their chemical structures and preparation. The synthesis of the colchicine derivatives started with the conversion of the known classical colchicine structure to the ether or ester structure at the C1 position. Substitution and elongation of the alkyl side chain at the C1 position was accomplished by following etherification protocol in the presence of $SnCl_4$ protected salt. Removal of the $CH_3COO$— group at C1 in product (2) using hydrolysis was activated by $K_2CO_3$ (FIG. 1). The use of this procedure resulted in 71% yield of (3). Acylation of the (2) afforded ester (4-5) derivatives (FIG. 2) while alkylation gives ether (6-16) derivatives (FIG. 3). Among these compounds, fluorine derivatives (28-38) were synthesized using introduction of the (—$COCH_2NHCOCF_3$) group in side chain at the C7 position.

Figure 5:
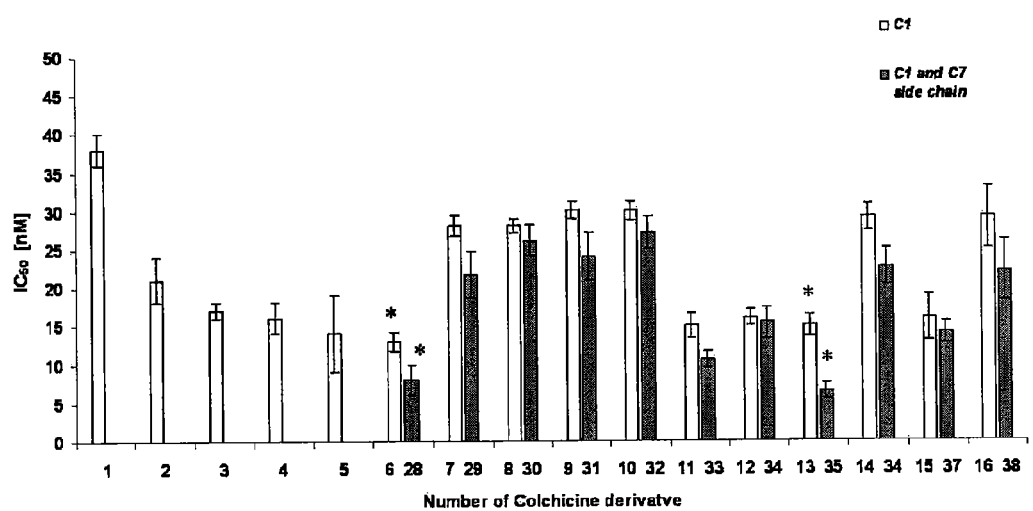
FIG. 5 shows $IC_{50}$ values for compounds (1) to (38)
Figure 6:
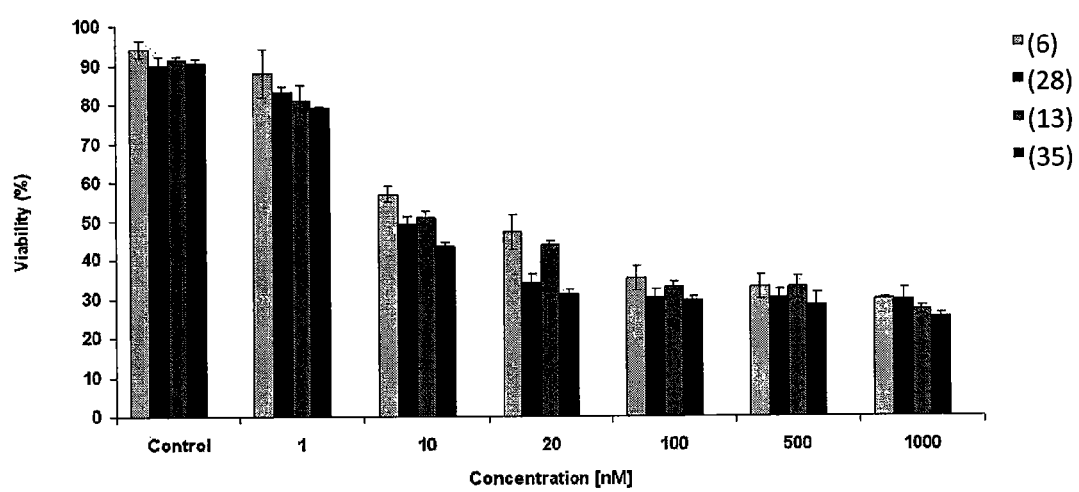
FIG. 6 shows viability of cells treated with (6), (13), (28) and (35)
Figure 7:
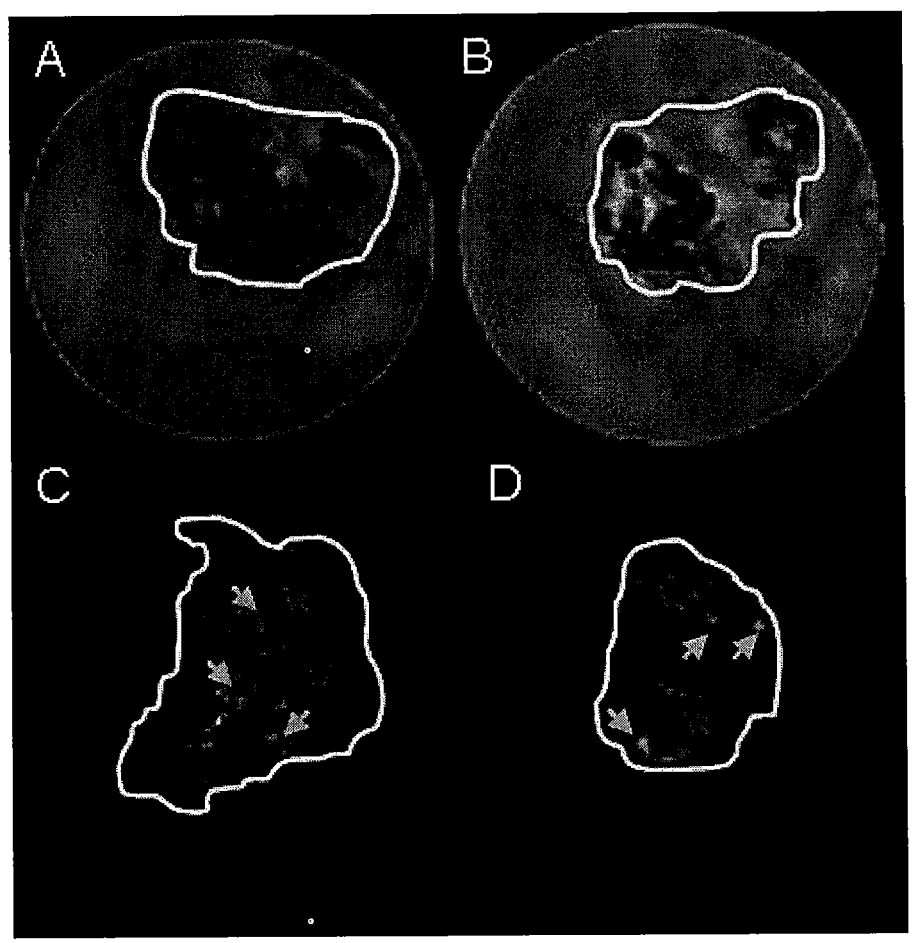
FIG. 7 shows $^1H$ MRI of cells treated with (6) A; $^1H$ MRI of cells treated with (13) B; $^{19}F$ MRI of cells treated with (28) C; $^{19}F$ MRI of cells treated with (35) D; in C and D, the light grey arrows indicate a region with higher fluorine derivatives uptake and the darker grey arrows indicate a region with lower uptake of fluorine derivatives.

The 72 h incubations of CEM cells with (6-16) and (28-35) decreased cell viability showing the ability of the analogues to accumulate and interact within cells. The observed $IC_{50}$ of the cell growth inhibition using colchicine analogues is summarized in FIG. 5. The analogues of (6-16) exhibited a similar effect with the main value $IC_{50}$=13±1 nM. However, (28-35) analogues showed a higher decrease in cell viability and the main $IC_{50}$=7±2 nM. The fluorinated analogues (28-35) were the most effective compounds in all studied series (1-38). The compounds (6) and (13) showed significant changes in $IC_{50}$ values. Based on these results, compounds (6) and (13) and their fluorinated analogues (28) and (35) were studied in HFB device. The influence of the investigated compounds on 3-D CEM cell growth was confirmed with cell viability binding assays. As shown in FIG. 6, the compounds (6) or (13) and fluorinated analogues (28) or (35) were able to induce the high growth inhibition effect in HFB cultures. The viability of the control (untreated) cells during culture was 93±2%. A configuration of 3-D cell structure was provided by $^1$H image of cells treated with (6) and (13). The loss of cell number during the uptake of the derivatives (FIGS. 7A-7D) was visible within 72 h. The study showed that the cell exposure to 1000 nM of (28) and (35), the number of viable cells decreased from $10^9$ cells/mL to 3.45×$10^8$ cells/mL and from $10^9$ cells/mL to 2.9×$10^8$ cells/mL, respectively, within 72 h.

The distribution of the cells, measured with MRI, was highly dependent on the cells' densities (FIGS. 7A-7D). A significantly higher number of cells were killed in the regions where the cells' density was high. The mean $^{19}$F SI of the cells treated with (28) increased during treatment and corresponding to a mean cells concentration of 6.03×$10^8$ cells/mL. The mean CEM cell density in the region with lower densities corresponds to 2.4×$10^8$ cells/mL while the mean number of cells with higher cell densities 3.5×$10^8$ cells/mL. At the same time the viability of cells in HFB treated with (28) was 35% and corresponding to 3.45×$10^8$ cells/mL viable cells in HFB.

Figure 8:
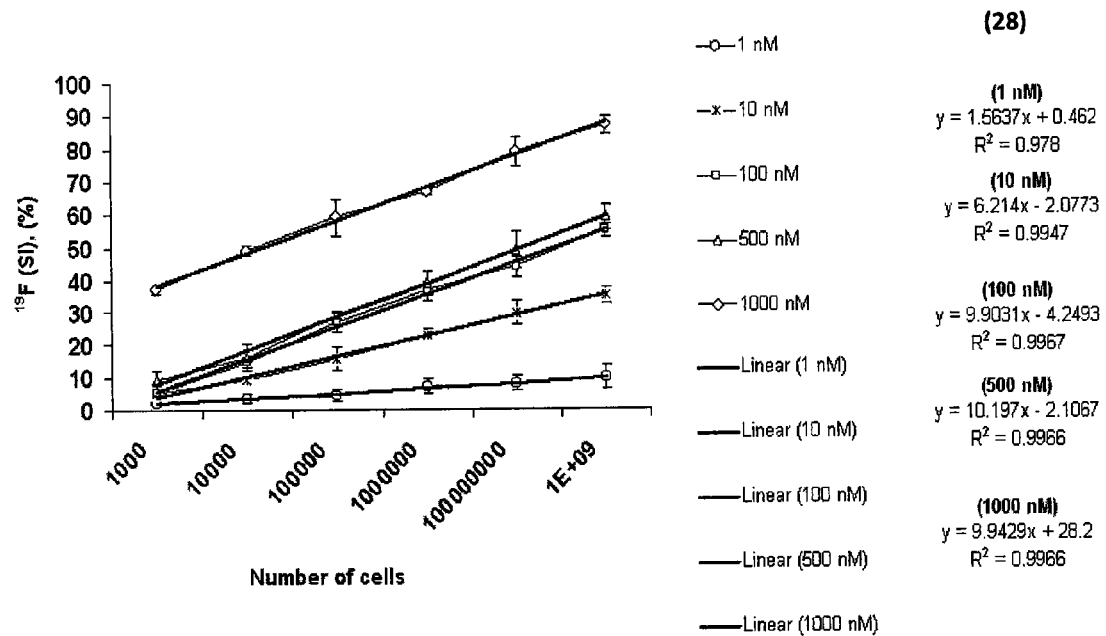
FIG. 8 shows an increase of $^{19}F$ SI for (28) vs. number of cells (100% corresponds to SI of (28) without cells)
Figure 9:
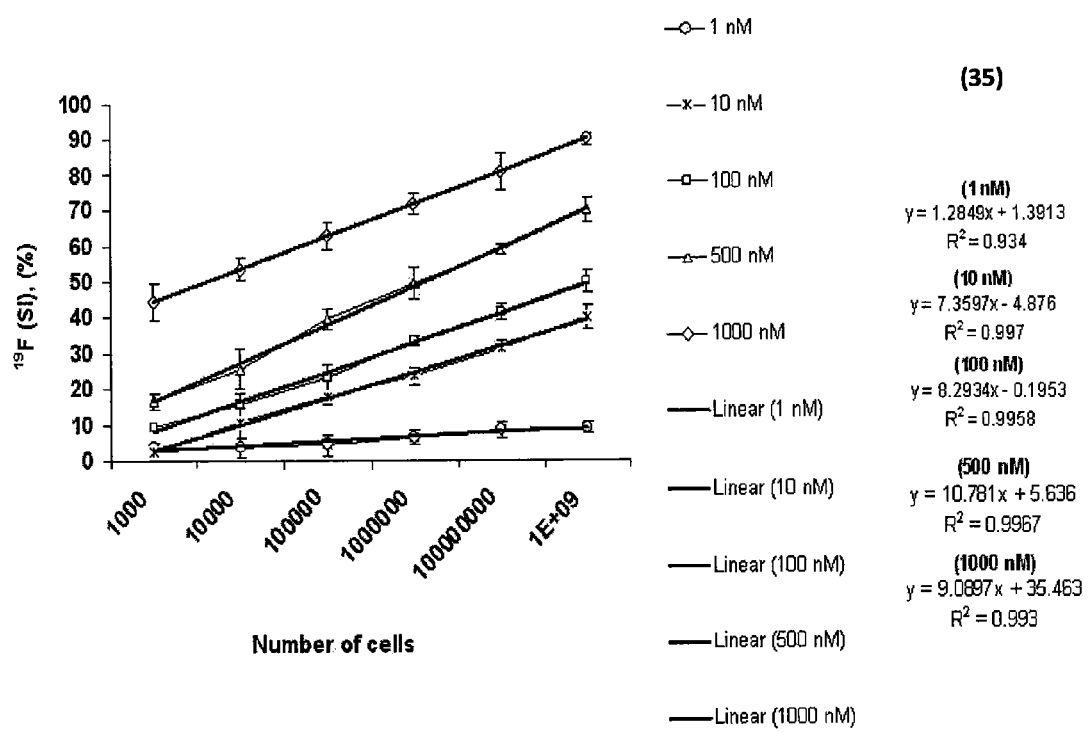
FIG. 9 shows an increase of $^{19}F$ SI for (35) vs. number of cells (100% corresponds to SI of (35) without cells)

The mean $^{19}$F SI of the cells treated with (35) also increased during treatment and corresponded to a mean cell concentration of 6.9×$10^8$ cells/mL. The viability of cells in HFB treated with (35) was 30% and corresponded to live cells 2.9×$10^8$ cells/mL after 3 days of treatment. The mean CEM cell density in the region with lower densities corresponded to 1.4×$10^8$ cells/mL while the mean numbers of cells with higher cell densities was 4.8×$10^8$ cells/mL. As expected, the $^{19}$F SI values were dependent on the concentration of cells and fluorine derivatives in the cells treated with (28) (FIG. 8) and (35) (FIG. 9).

Moreover, it was found, that 3-D high density of tissues was needed for the study due to the limited MRI sensitivity. It was also found, that the HFB provides high enough concentration of 3D cell cultures to obtain $^{19}$F MR images thus the combined MRI techniques and HFB device can be used for studying drug efficacy and cell viability.

Figure 10:
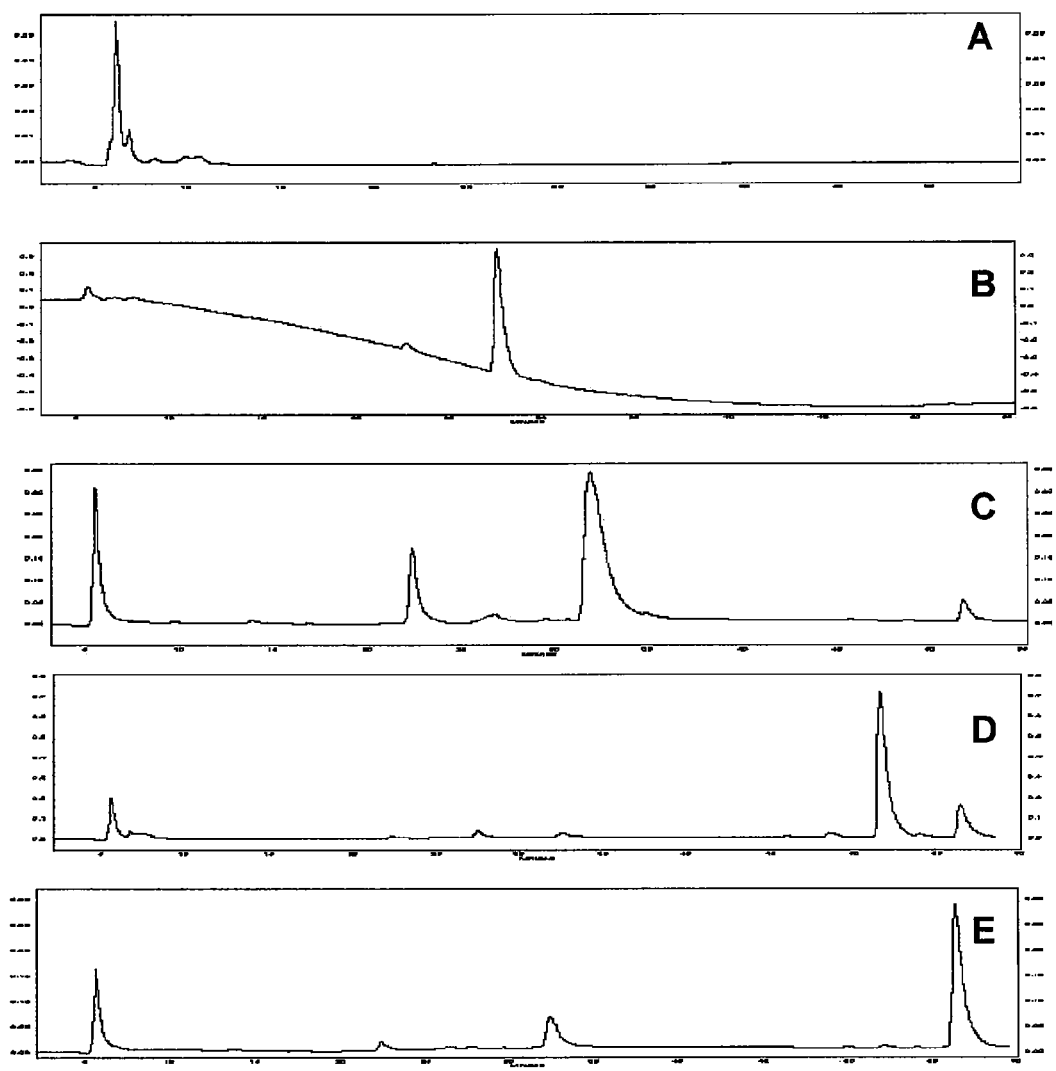
FIG. 10 shows HPLC chromatograms of derivatives: CEM cells (A), (6) (B), (13) (C), (28) (D) and (35) (E)

The results of the HPLC analysis of the treated CEM cells ex vivo are shown in FIGS. 10A-10E. As shown in FIGS. 10C and 10D, CEM cells in response to treatment with (13)

and (35) expressed the minor histocompatibility complex (MHC (class I) receptor eluted at 53 min. When the viability was 45% and 35%, the expression of MHC (class I) receptor was observed with intensities of 0.05 V and 0.7 V, respectively. MHC (class I) receptor treated with IgG showed decrease in viability of cells for 10% as compared with cells before treatment. The exposure of cells to (6), (13) and (28) showed a new HPLC peak with low intensity, the Tn receptor. The signal of Tn in cells treated with (13) had an intensity 10 times higher in 45% viable cell culture than treated with (6) in 50% viable cell culture and (28) in 38% viable cell culture. It was assumed that signals eluted at 30-35 min were unreacted derivatives with variable intensity of 0.1 V for (28) and (35) as well as 0.35 V for (13) and 0.9 V for (6). The viability of cell cultures were higher for samples where unreacted colchicine derivatives were presented with higher intensities and were as follow: 38%±4 for (28), 35%±5 for (35), 45%±2 for (13) and 50%±4 for (6). An additional signal eluted at 57 min occurred in samples treated with (35) and (28) (FIGS. 10D and 10E). The signals at 57 min differ at about 5 min in elution present one from cascade of apoptotic protein in treated cells. The peak intensity of 0.3 V (28) and 0.2 V (35) corresponded to viability of cells 38% (28) and 35% (35) and unreacted derivatives 0.1 (28), 0.1 (35), respectively. The undefined additional peaks with very low intensities, less then 0.05 V, are the metabolites of derivatives or unreacted compounds.

CEM Cell Growth and Treatment with Thiocolchicine Compounds (40-42 and 44-49)

Cell Cultures

CEM cells, American Type Culture Collection (Manassas, Va.), were maintained in tissue culture flasks and cultured as monolayer in 20 ml of RPMI media containing 10% Fetal Bovine Serum (FBS) and divided from $5\times10^5$ cells/mL to $2.5\times10^4$ cells/mL two times per week. When the number of the cells in the culture flask reached $5-6\times10^6$ cells/ml the culture was harvested and then inoculated into six Hollow Fiber Bioreactors (HFB, FiberCells System Inc., Frederick, Md.) and then continuously cultured in 37° C. and 5% $CO_2$. The HFB consists of a single, hydrophilic and polysulfone fiber with 0.1 μm diameter pores. The media circulate within the HFB cartridge and polysulphone tubing, at flow rate of 14 mL/min, bringing oxygen and nutrients to cells and removing $CO_2$ and other waste. Collagen solution was used to create an extracellular matrix between cells and fiber. The polysulfone fiber was coated with protein by flushing with 10 mL of coating solution containing 1 mg collagen per 1 mL Phosphate Buffered Saline (PBS). In this manner, CEM cells growing originally in suspension build up a 3-D solid tumor. During 4 weeks of culturing, the media were replaced each week.

Preparation of Media with Colchicine Derivatives (40), (41) and (42)

The Colchicine derivatives (40), (41) and (42) treated media were prepared using 1 nM, 10 nM, 20 nM, 100 nM, 500 nM and 1000 nM of (40) or (41) or (42) placed in a 1.5 mL glass vial and dissolved in 10 μL of dimethyl sulfoxide. Dimethyl sulfoxide is a solvent of the (40), (41), and (42) derivatives. Once dissolved, the dimethyl sulfoxide (40), (41) or (42) mixture was added to media and incubated overnight in 37° C.

Preparation of Media with Colchicine Derivatives (47), (48) and (49)

The media were supplemented with 1 nM, 5 nM, 10 nM, 20 nM, 100 nM, 500 nM and 1000 nM of (47), (48) or (49) derivatives dissolved in 10 μL of dimethyl sulfoxide. The (47), (48) or (49) derivatives were dissolvable in media solution. However, the dimethyl sulfoxide regime used for (40), (41) or (42) derivatives was also used for (47), (48) or (49).

Treatment of Cell

Approximately $4\times10^4$ CEM cells/ml were treated on culture plates and placed for the 72 hours incubation with (40), (41), (42), (47), (48) and (49) derivatives. After 72 hours, the growth was inhibited more than 50% for 20 nM of (40), 10 nM of (41) and (42), 5 nM of (47), (48) and (49). Therefore, we selected these concentrations for $10^9$ CEM cells/mL concentrations for cell treatment in HFB, after 4 weeks in culture.

Viability

The number of cells was determined using Trypan blue (Sigma-Aldrich, Oakville, ON) exclusion method (K. Takahashi, G. Loo, Biochem. Pharmacol. 67 (2004) 315-324). Briefly, CEM cells were harvested from HFB, seeded in 6 well microplates and exposed to 0.4% (w/v) trypan blue dye solution. Cell number was determined manually with a hemacytometer chamber (Hausser Scientific, Horsham, Pa.).

Cell Preparation for $^1H$ and $^{19}F$ Magnetic Resonance Imaging (MRI)

$^1H$ and $^{19}F$ MR measurements of the cells in the HFB were performed in control (n=2, HFB) and treated cells (n=6, HFB) using 1 nM, 5 nM, 10 nM, 20 nM, 100 nM, 500 nM and 1000 nM of (40), (41), (42), (47), (48) and (49) derivative respectively. Throughout the MRI experiments, the HFBs were maintained under incubator-like conditions (37° C., 5% $CO_2$ and 95% air). All MR images were collected with 9.4 Tesla/21 cm magnets (Magnex, UK) and TMX console (NRC-IBD). The HFBs with cell cultures were placed in double tuned transmit/receive radio frequency (RF) volume coil operating at 376 MHz and 400 MHz corresponding to $^{19}F$ and $^1H$ Larmour frequency at 9.4 Tesla, respectively. All $^1H$ and $^{19}F$ imaging parameters were the same for each HFB treated with (40), (41), (42) and (47), (48) and (49) derivatives, respectively. For $^1H$ MR imaging, a spin echo pulse sequence was used with Time to Echo (TE)/Time to Repetition (TR)=16.5/5000 ms. For $^{19}F$ MR imaging, Inversion Recovery (IR) spin-echo method with Inversion Time (IT) equal to 400 ms and TE/TR=16.5/5000 ms were used. A single slice of 1 mm thickness was acquired with matrix size of 256×256 and field of view 3 cm×3 cm.

High Performance Liquid Chromatography-Ultra Violet (HPLC-UV) Analysis

Digested cell samples were fractionated with a Gold HPLC chromatograph system equipped with a Gold 166 Ultra Violet (UV) Detector and 32-Karat software (Beckman-Coulter, Mississauga, ON). For reversed-phase HPLC, a Vydac 218 TP54 Protein & Peptide C18 analytical column, 300 Å pore size, 0.46 cm×25 cm (Separation Group, Hesperia, Calif.) was used. The chromatograph was equipped with a Rheodyne injector (5 μL). UV detection was performed at 245 nm. Eluent A consisted of 5% acetonitrile (ACN) water solution and eluent B of 0.01% trifluoroacetic acid in 95% ACN water solution. A linear gradient from 5 to 70% ACN was applied over 60 min.

Antibody Targeting of MHC Class I Receptor

The stock solution of 0.2 mg/ml antibodies in PBS pH 7.2 with 10 mg/ml bovine serum albumin (BSA) was used to treat $10^9$ cell/mL.

Statistical Analysis

Results were expressed as a mean±SD. Differences between groups at each time-point were identified by one-way Anova. Statistical comparison between two independent variables was determined by two-way Anova with Dunnet's correction performed post-hoc to correct multiple comparisons. The p-values <0.05 were considered statistically significant. All data reported here are from sets of 6 separate experiments. Error bars in all graphs represents the standard error of the mean. Data were analyzed using the Sigma Stat Soft (Chicago, Ill.) software.

Results

Thiocolchicine (39) was the starting compounds for the preparation of a series of thiocolchicine derivatives (40-42), (44-46) and (47-49) (FIG. 4). It was possible to produce (41) and (42) compounds by the alkylation reaction of (40) compound where R was a hydrogen atom at C3. For this purpose an aqueous alkaline sodium salt solution was reacted with derivative (40) in the presence of acetone and usually the yield was higher then 50% while proceeding in this manner. Hydrolysis of acetamides (40), (41) and (42) with 20% of methanolic HCl gave the amines (44), (45) and (46), respectively. The choice of introduction of the trifluoroacetyl group in amino acids fragment at the C-7 resulted in (47), (48) and (49) compounds. These functionalized N-fluoroacethylthiocolchicines were prepared from (44), (45) and (46) compounds, respectively.

The control CEM cells cultured in the HFB reached density of $10^9$ cells/mL with the viability greater than 95% within 4 weeks. Specifically, conventional culture CEM cells was used to establish originally $IC_{50}$ values. The growth inhibitory activity of thiocolchicine with $IC_{50}=8.5$ nM was about 5-fold lower than $IC_{50}$ of Colchicine (40 nM). Considering Thiocolchicine as the model compound, the effect of the substitution of 3-methoxy or 7-acetamido group on the ring A or B in the Thicolchicine derivatives series was evaluated on the CEM cell lines growth. Therefore, the $IC_{50}$ values was determined for all synthesized compounds. All Thicolchicine derivatives demonstrated strong cytotoxicity with mean $IC_{50}$ values of 6.8±3 nM. Compound (40), with substitution at the C-3 position, showed $IC_{50}=5.1±1.3$ nM that was lower than the $IC_{50}$ values of (41) and (42).

In vitro structures (47), (48) and (49) in the presence of fluorine nuclei at the C-7 in the form of (—COCH$_2$NHCOCF$_3$) group were examined. The significant differences (p-value <0.05) in $IC_{50}$ values were observed for (47), (48) and (49) and compared with (44), (45), (46) and (40), (41) and (42), respectively, in vitro. The $IC_{50}$ values of (47), (48) and (49) were about 8-fold lower than $IC_{50}$ of (39). Thicolchicine derivatives with substitution at C-7 and C-3 showed about 5-fold lower $IC_{50}$ than Thiocolchicine derivatives with substitution at C-3. There was no decrease in cell growth for cells placed in 10 µL of dimethyl sulfoxide only.

Figure 11:
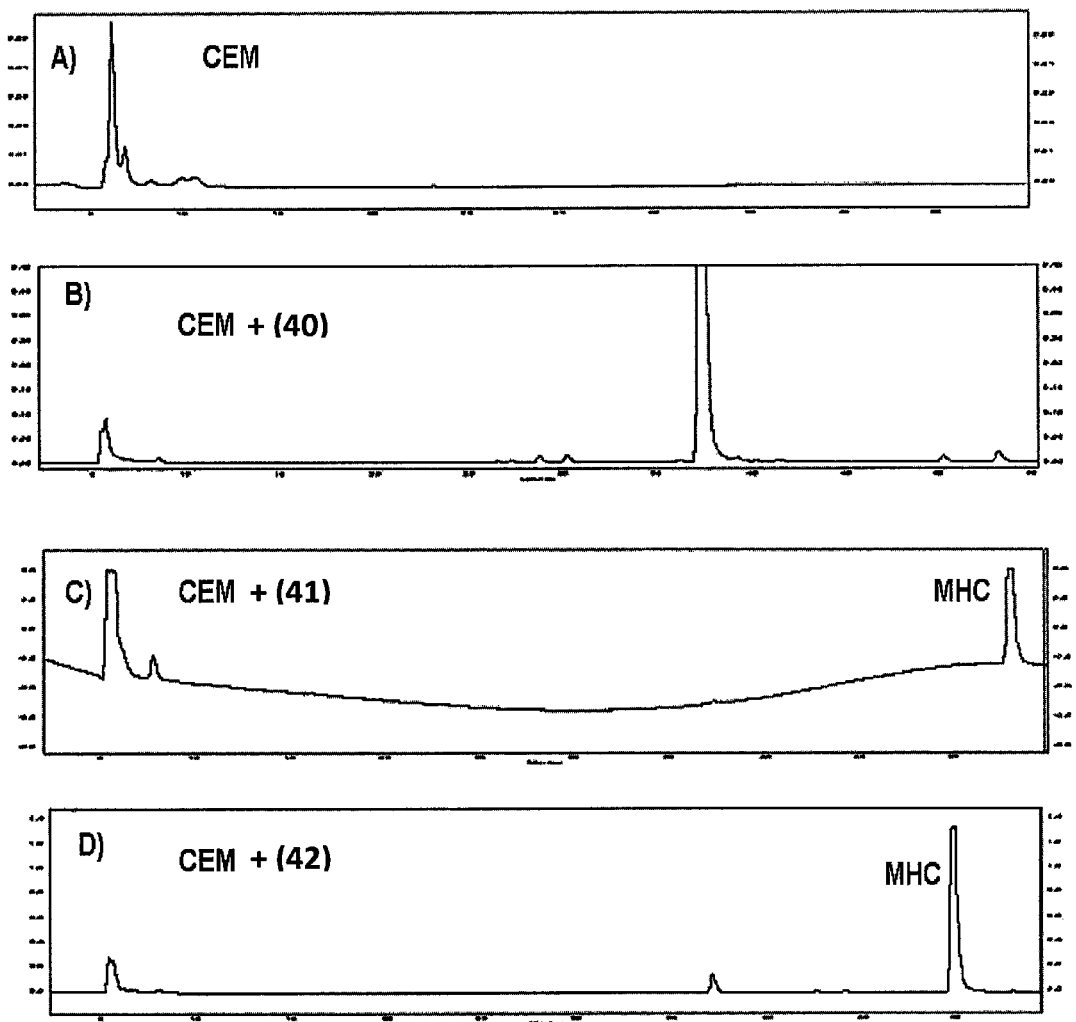
FIG. 11 shows HPLC-UV chromatograms of untreated CEM cells (A); CEM cells treated with (40) (B); CEM cells treated with (41) (C); and CEM cells treated with (42) (D)

The results of the HPLC analysis of the untreated and treated CEM cells are shown in FIG. 11. The chromatograms showed expression of minor histocompatibility complex (MHC class I) receptor eluted at 53 min in samples treated with (41) and (42). Treatment with monoclonal antibody directed to MHC (class I) receptor resulted in more than 90% killing effect. Compounds (41) and (42) were more active in growth inhibition. The HPLC fraction of the untreated cells contains only a major peak at 5 min. Thus, the changes in profiles of treated cells correspond to the changes in cell viability and cellular pathogenesis.

Figure 12:
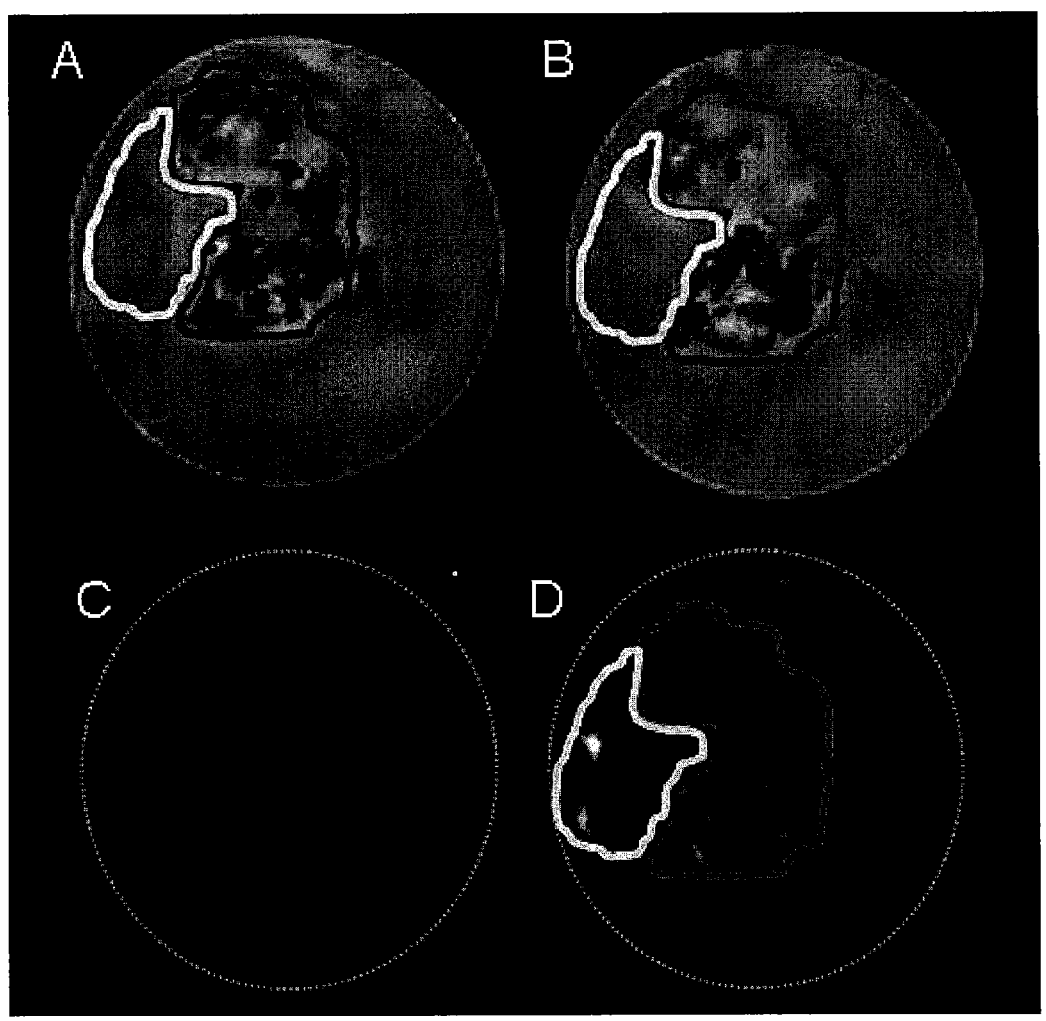
FIG. 12 shows MR images of the CEM cells in the hollow fiber bioreactor at 9.4 Tesla; the dark grey solid line indicates the area of high cell densities and the white solid line indicates low cell density regions; the images: $^1H$ MRI of cells before treatment with (47) (A); after 72 h treatment with (47) derivative (B); Spin echo (SE) pulse sequence (TR/TE=5000/12.8 ms, FOV=3 cm×3 cm, slice thickness 1 mm and matrix 256×256) was used; $^{19}F$ MRI of cells before treatment with (47) (C), after 72 h treatment with (47) derivative (D); the dotted line in (C) and (D) indicates the contour of HFB; Inversion Recovery (IR) spin echo method with Inversion Time (IT) equal to 400 ms and TE/TR=16.5/5000 ms, slice thickness 1 mm and matrix 256×256 was used.

The use of three dimensional (3-D) cultured cells proved that CEM cells originally cultured in suspension can form high density structure suitable for MRI experiments. The thiocolchicine derivatives suppressed cell number during 72 h of treatment and these changes are visible in FIG. 12B as compared to initial tumor size at FIG. 12A. $^1$H MR image shows cell aggregation in HFB before and after 72 h treatment. Because, synthesized compounds (47), (48) and (49) have fluorine nuclei, $^{19}$F MRI was used to show changes in 3-D cell formation after 72 h. The $^{19}$F images (FIG. 12C) showed regions of suppressed cells while compared to $^1$H (FIG. 12B) performed at the same HFB cartridge. The MRI experiments (FIG. 12B and FIG. 12C) were performed at the time required to reach $IC_{50}$ and was 72 h. However, $^{19}$F MRI showed only 1.5 ppm difference between single peaks of the trifluoromethyl groups at spectra performed on (47), (48) and (49) compounds.

Cytotoxicity of Colchicine Derivatives Against Cancer Cell Lines

Materials and Methods

Cell lines used were A549 (Human lung carcinoma), HeLa (Human cervical carcinoma), MCF-7 (Human mammary gland adenocarcinoma), CEM (Human T-lymphoblastoid from ALL (Acute lymphoblastic leukemia)), M010B (Human glioma), M006X (Human glioma) and Jurkat (Human T-cell leukemia).

Tubulin Model Preparation

Figure 13:
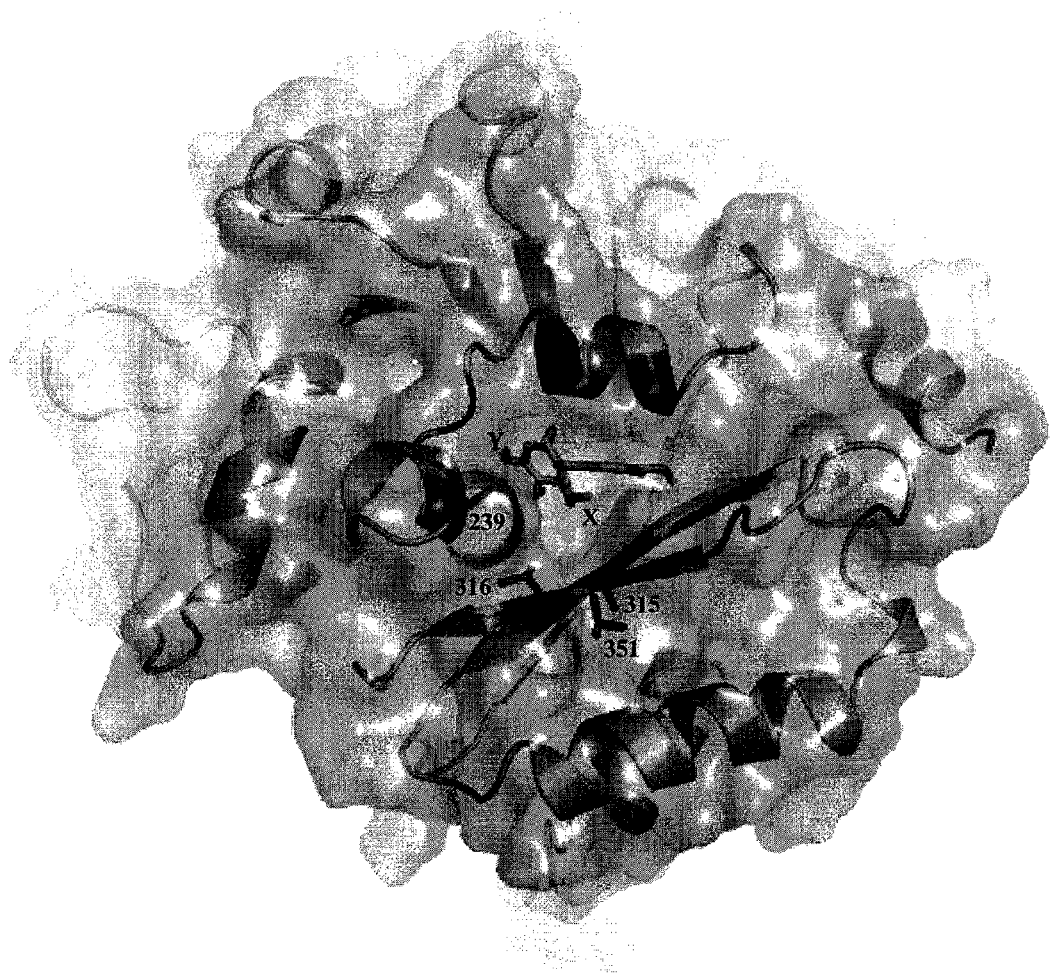
FIG. 13 shows differences between residues found within the colchicine binding site.

Consensus sequences for human β-tubulin isotypes have been previously described (Huzil J. T. et al., Nanotechnology. 2006:17:S90-S100). Residues making up the colchicine binding site were determined by examining the B chain within the 1 SA0 pdb coordinates (Ravelli R. B. et al., Nature. 2004; 428:198-202.). Using PyMol v1.0 (Delano W L. The PyMOL Molecular Graphics System. 2002), residues with any atom found within 6 Å from colchicine were selected. From this subset of residues, a minimal set of contact residues found within the colchicine binding site was defined (FIGS. 13A and 13B). Examination of primary sequences for βI, βIIa, βIIb, βIII, βIVa, βIVb and βV, based on this reduced contact set, placed the tubulin isotypes into one of three colchicine binding sites; Type I (βI and βIV), Type II (βII) and Type III (βIII and βV) (FIG. 13A). The template 3-tubulin structure obtained from the 1SA0 B chain coordinates (Ravelli et al., 2004, Nature, 428, 198-202), was then used to create the models by replacing appropriate residues from a standard conformer library using the mutate function found in PyMol v1.0 (Delano W L. The PyMOL Molecular Graphics System. 2002).

Minimization of each binding site models was performed in the GROMACS molecular dynamics (MD) package (version 3.2.1) (Lindahl F. et al., GROMACS 3.0: A package for molecular simulation and trajectory analysis. J. Mol. Mod. 2001; 7:306-17) using the CHARMm (Chemistry at HARvard Molecular Mechanics) molecular force field (Brooks B. R., Brooks CLr, Mackerell A D. J. et al., CHARMM: The biomolecular simulation program. J. Comput. Chem. 2009). Convergence criteria for Steepest Descents and Conjugate Gradient minimization were set at a gradient of 0.05 kcal mol-1 Å-1. Following minimization, a short simulated annealing run (100 ps) was performed in a fully solvated periodic box (100×100×100 Å). Unconstrained charges were counterbalanced with sodium ions and long range electrostatics were calculated using particle-mesh Ewald's (PME).

Colchicine Derivative Generation

The structure of colchicine as bound to tubulin was extracted from the pdb structural file 1SA0 (Ravelli R. B. et al., Nature. 2004; 428:198-202) and imported into MarvinSketch (ChemAxon, Hungary). Derivatization of the C1 and C3 methoxy groups (FIGS. 2-4) was accomplished by building modifications using the 3D drawing tools. Each of the derivatives was then exported in 3D coordinates as MDL Molfiles (Symyx Technologies, U.S.A.).

Colchicine Parameterization and Minimization

Colchicine and its derivative structures were prepared and parameterized using the CHARMm force field (Brooks B. R., Brooks CLr, Mackerell A D. J. et al., CHARMM: The biomolecular simulation program. J. Comput. Chem. 2009) as implemented in Discovery Studio v2.1 (Accelrys, Inc., U.S.A.). Prior to the reintroduction of each derivative into the Type I, II and III binding site models, an in vacuo minimization step was performed. Because the initial colchicine coordinates were obtained from a crystallographic structure, harmonic restraints (10 kcal mol$^{-1}$) were placed on the carbon atoms contained in each of the three rings. Hydrogens were added, bond orders fixed and atomic positions optimized using the CHARMm forcefield and the Adopted Basis set Newton Raphson (ABNR) protocol until the root mean deviation (RMS) gradient was less than 0.05 kcal mol$^{-1}$ Å$^{-1}$. The second generation colchicine derivatives were prepared slightly differently; individual systems were placed into a TIP3 water box using GROMACS and minimized. Following a short equilibration, system energies for three separate conditions were obtained. The energy for the solvated tubulin-colchicine complexes E(P+L) was subtracted from the energy obtained from a tubulin colchicine system, where colchicine was not bound to the colchicine binding site E(P–L). A large water box was used to ensure no non-bonded interactions between colchicine and tubulin were introduced in the E(P–L) case.

Computational Colchicine Screening

Docking of the 20 colchicine derivatives to the Type I, II and III binding sites was performed using CDOCKER (Wu G. et al., J. Comput Chem. 2003; 24:1549-62), as implemented in Discovery Studio v2.1 (Accelrys, Inc., U.S.A.). Briefly, a conformational search of the derivatives was carried out using a simulated annealing MD approach with the CHARMm force field (Brooks B. R., Brooks CLr, Mackerell A D. J. et al., CHARMM: The biomolecular simulation program. J. Comput. Chem. 2009). Selection of an input site sphere was defined over the entire colchicine binding site. Each derivative was then heated to a temperature T=700K and annealed to T=300K. Ten such cycles were carried out for each of the 20 colchicine derivatives, producing 600 poses. Each conformation was then subjected to local energy minimization, using the ABNR method described above.

Binding Energy Evaluation

Using MM-GBSA (Molecular Mechanics-Generalized Born Surface Area), the binding energy was evaluated for each system using vacuum electrostatics and solvation was approximated using the Generalized Born model. Binding energies were calculated by obtaining the total potential energy of the system and subtracting the energy of the derivative and that of the empty dimer:

$$E_{bind} = E_{complex} - E_{tubulin} - E_{drug}$$

For the second generation colchicine derivatives, the energy was determined slightly differently:

$$Ebind = E(P-L) - E(P+L)$$

Drug-binding to Purified Tubulin Isotypes

Tubulin was purified from bulk microtubule protein by phosphocellulose chromatography (Fellous A., et al., Eur. J. Biochem. 1977; 78:167-74). The αβII and αβIII tubulin dimers were subsequently purified by immunoaffinity chromatography using monoclonal antibodies as previously described (Banerjee A. et al., J. Biol. Chem. 1992; 267: 13335-9; and Baneljee A. et al., J. Biol. Chem. 1988; 263:3029-34). For kinetic fluorescence measurements, 500 µL aliquots of tubulin (0.1 mg/ml) were incubated at 37° C. in quartz fluorescence cuvettes (path length 0.5 cm) in the presence of a series of drug concentrations. Kinetics were performed under pseudo-first-order conditions using drugs in large excess over tubulin. The excitation and emission wavelengths used were 380 nm and 437 nm, respectively.

The corrected fluorescence values were plotted as a function of time (t) and fitted to the curve:

$$F_{max} - F_t = Ae^{(-k_{on,app})(t)}$$

Under these conditions, $k_{on,app}$ is a good index of the degree of interaction between a drug and a tubulin isotype. An expected linear plot of $Ln(F_{max}-F_t)$ versus t has a slope $k_{on,app}$. The $k_{on,app}$ values were plotted as a function of the values previously reported for αβII, and αβIII, 132 and 30 M-1 s-1 respectively (Banerjee A. et al., J. Biol. Chem. 1992; 267:13335-9).

Cytotoxicity

Drug solutions were prepared by dissolving it into 4.5% dimethylsulfoxide and diluting with distilled water to a final concentration of 1 mM. A series of dilutions were prepared and a wavelength scan of the diluted solution was used to determine the wavelength of maximum absorbance for each compound. Five standardized drug concentrations were scanned at this pre-determined wavelength to obtain an estimate of the compound's extinction coefficient.

A primary MTS assay was used to test the optimal number of cells for cytotoxicity assays. Cells were trypsinized, counted and introduced into seven lanes of a 96-well plate at different cell numbers (eight replicates per lane). Optimal cell numbers were determined after 72 and 96 hours of growth and were used in subsequent cytotoxicity assays. Adherent cells were plated into nine lanes of a 96-well plate at the pre-determined cell number and twenty-four hours later, set concentrations of colchicine derivatives were added to eight of the lanes containing cells. The same drug solutions were prepared with suspension cell lines at the predetermined cell concentrations, plated and grown with the corresponding colchicine derivatives for 48 and 72 hours. Cell viability was determined using the Cell Titer 96 AQueous One Solution Cell Proliferation Assay (Promega, U.S.A.).

Cytotoxicity Data Fitting

Fits were performed using a dose-response model ideal for data showing an initial response plateau, a transition region, and a final response plateau.

$$\text{response} = \frac{I_{bot} - I_{top}}{1 + 10^{HILL}(\log IC_{50} - [conc])} + I_{top}$$

HILL is a measure of the steepness of the transition region and was fixed at a value of 2.5. $I_{top}$ is the response obtained at very low/no drug concentration. The data and all parameters were normalized to $I_{top}-I_{bot}$, a measure of the maximum effect of the drug. A Monte Carlo method (N. Metropolis (1987), "The beginning of the Monte Carlo method", Los Alamos Science Special Issue dedicated to Stanislaw Ulam: p 125-130) was then used to measure the sensitivity of the parameters to small changes in the data, and standard deviations for the parameters were calculated (Tables 1 and 2).

TABLE 1 logIC$_{50}$ values [log$_{10}$ M] for colchicine and various colchicine derivatives, determined by cytotoxicity testing on six different cell lines.

| | A549 | HeLa | MCF-7 | CEM | M010B | M006X |
|---|---|---|---|---|---|---|
| CH | −6.46 ± 0.04 | −6.86 ± 0.05 | −7.83 ± 0.06 | −8.03 ± 0.04 | −7.70 ± 0.05 | −8.35 ± 0.29 |
| 2 | −5.89 ± 0.06 | −6.48 ± 0.13 | −6.32 ± 0.10 | −6.65 ± 0.08 | X | X |
| 3 | −5.29 ± 0.11 | X* | −5.25 ± 0.10 | X | X | X |
| 4 | −5.07 ± 0.04 | −5.41 ± 0.13 | −5.23 ± 0.07 | −5.39 ± 0.11 | X | X |
| 5 | −5.09 ± 0.06 | −5.46 ± 0.13 | −5.25 ± 0.08 | −5.51 ± 0.13 | −5.22 ± 0.06 | −6.12 ± 0.04 |
| 6 | −7.83 ± 0.10 | −7.89 ± 0.06 | −7.42 ± 0.13 | −8.64 ± 0.08 | −7.94 ± 0.04 | −8.41 ± 0.08 |
| 7 | −7.66 ± 0.08 | −8.25 ± 0.09 | −8.10 ± 0.05 | −8.49 ± 0.10 | X | X |
| 7a | −6.52 ± 0.13 | −6.66 ± 0.11 | −6.17 ± 0.06 | −6.76 ± 0.08 | −6.60 ± 0.14 | −7.12 ± 0.06 |
| 8 | −7.80 ± 0.07 | −7.68 ± 0.09 | −7.50 ± 0.12 | −8.48 ± 0.10 | −7.49 ± 0.13 | −7.98 ± 0.03 |
| 9 | −6.66 ± 0.10 | −7.35 ± 0.09 | −7.10 ± 0.05 | −7.46 ± 0.08 | −6.74 ± 0.08 | −7.47 ± 0.09 |
| 10 | −5.77 ± 0.10 | −6.17 ± 0.07 | −6.27 ± 0.08 | −6.45 ± 0.09 | −5.66 ± 0.10 | −6.42 ± 0.09 |
| 11 | −6.47 ± 0.12 | −7.23 ± 0.09 | −7.05 ± 0.04 | −7.45 ± 0.09 | −6.74 ± 0.08 | −7.40 ± 0.09 |
| 12 | −6.00 ± 0.04 | −6.43 ± 0.15 | −6.30 ± 0.12 | −6.46 ± 0.09 | −6.39 ± 0.11 | −6.47 ± 0.12 |
| 13 | −4.51 ± 0.32 | −5.33 ± 0.14 | −5.19 ± 0.09 | −5.50 ± 0.10 | −4.90 ± 0.09 | −5.67 ± 0.12 |
| 15 | −6.23 ± 0.08 | −6.22 ± 0.09 | −6.35 ± 0.12 | −6.57 ± 0.11 | −6.38 ± 0.14 | −6.45 ± 0.13 |
| 16 | −4.95 ± 0.07 | −5.33 ± 0.11 | −5.22 ± 0.08 | −5.53 ± 0.10 | −5.20 ± 0.08 | −5.44 ± 0.12 |
| 40 | −7.38 ± 0.14 | −7.77 ± 0.09 | −7.37 ± 0.11 | −8.47 ± 0.13 | −7.65 ± 0.10 | −8.34 ± 0.12 |
| 41 | −8.50 ± 0.11 | −8.45 ± 0.11 | −8.31 ± 0.12 | −8.29 ± 0.10 | X | X |
| 42 | −8.37 ± 0.10 | −8.47 ± 0.14 | −8.28 ± 0.10 | −8.64 ± 0.09 | −8.27 ± 0.12 | −8.83 ± 0.08 |
| 43 | −8.76 ± 0.11 | −8.66 ± 0.12 | −8.71 ± 0.10 | −8.55 ± 0.09 | −8.51 ± 0.15 | X |

*Insufficient data
†Did not dissolve at normal pH

TABLE 2

Fraction of cells that survive at the highest drug concentrations (Ibot) values for colchicine and various colchicine derivatives, determined by cytotoxicity testing on six different cell lines.

| | A549 | HeLa | MCF-7 | CEM | M010B | M006X |
|---|---|---|---|---|---|---|
| CH | 0.118 ± 0.042 | 0.061 ± 0.048 | 0.377 ± 0.010 | 0.016 ± 0.021 | 0.107 ± 0.017 | 0.026 ± 0.005 |
| 2 | 0.283 ± 0.022 | 0.074 ± 0.031 | 0.424 ± 0.019 | 0.027 ± 0.021 | X | X |
| 3 | 0.235 ± 0.048 | X* | 0.518 ± 0.033 | X | X | X |
| 4 | 0.332 ± 0.028 | 0.058 ± 0.048 | 0.399 ± 0.021 | −0.031 ± 0.049 | X | X |
| 5 | 0.265 ± 0.043 | 0.025 ± 0.044 | 0.451 ± 0.025 | −0.003 ± 0.048 | 0.258 ± 0.024 | 0.031 ± 0.018 |
| 6 | 0.249 ± 0.030 | 0.089 ± 0.026 | 0.605 ± 0.015 | −0.062 ± 0.026 | 0.108 ± 0.013 | 0.039 ± 0.011 |
| 7 | 0.229 ± 0.014 | 0.066 ± 0.022 | 0.464 ± 0.009 | 0.000 ± 0.014 | X | X |
| 7a | 0.222 ± 0.026 | 0.051 ± 0.032 | 0.406 ± 0.014 | 0.022 ± 0.020 | 0.239 ± 0.031 | 0.197 ± 0.024 |
| 8 | 0.246 ± 0.013 | 0.044 ± 0.020 | 0.433 ± 0.013 | 0.000 ± 0.013 | 0.181 ± 0.020 | 0.072 ± 0.014 |
| 9 | 0.227 ± 0.021 | 0.082 ± 0.018 | 0.484 ± 0.009 | −0.004 ± 0.015 | 0.299 ± 0.017 | 0.037 ± 0.015 |
| 10 | 0.256 ± 0.032 | 0.080 ± 0.026 | 0.387 ± 0.016 | 0.012 ± 0.022 | 0.250 ± 0.031 | 0.088 ± 0.022 |
| 11 | 0.223 ± 0.024 | 0.078 ± 0.023 | 0.388 ± 0.012 | 0.012 ± 0.016 | 0.288 ± 0.017 | 0.063 ± 0.016 |
| 12 | 0.245 ± 0.024 | 0.040 ± 0.038 | 0.390 ± 0.025 | −0.015 ± 0.021 | 0.328 ± 0.022 | 0.051 ± 0.027 |
| 13 | 0.218 ± 2.644 | 0.059 ± 0.059 | 0.364 ± 0.038 | −0.026 ± 0.039 | 0.305 ± 0.053 | 0.055 ± 0.046 |
| 15 | 0.288 ± 0.020 | 0.039 ± 0.034 | 0.381 ± 0.024 | −0.016 ± 0.032 | 0.382 ± 0.028 | 0.058 ± 0.030 |
| 16 | 0.189 ± 0.052 | −0.001 ± 0.051 | 0.331 ± 0.033 | −0.014 ± 0.042 | 0.266 ± 0.036 | 0.026 ± 0.043 |
| 40 | 0.230 ± 0.027 | 0.039 ± 0.026 | 0.459 ± 0.013 | 0.015 ± 0.022 | 0.118 ± 0.026 | 0.061 ± 0.029 |
| 41 | 0.243 ± 0.012 | 0.039 ± 0.016 | 0.472 ± 0.016 | −0.050 ± 0.022 | X | X |
| 42 | 0.256 ± 0.015 | 0.046 ± 0.026 | 0.538 ± 0.010 | 0.026 ± 0.018 | 0.327 ± 0.023 | 0.184 ± 0.021 |
| 43 | 0.198 ± 0.024 | 0.025 ± 0.025 | 0.399 ± 0.015 | 0.010 ± 0.014 | 0.214 ± 0.022 | X |

*Insufficient data
†Did not dissolve at normal pH

Results

Isotype Sequence Analysis

The tertiary structure of tubulin can be divided into three distinct domains: domain I (residues 1-198), domain II (residues 199-373) and domain III (residues 374-428) (Nogales E. et al., Nature. 1995; 375:424-7). The βI, βIIa, βIIb, βIII, βIVa, βIVb and βV isotypes respectively share 87.4%, 88.1% and 96.3% identity within these domains. For residues involved in paclitaxel binding (Nogales E. et al., Nature. 1995; 375:424-7), there was a greater than expected 91.7% sequence identity when compared to the overall identity between β-tubulin isotypes. This higher than average trend continues with the Vinca binding site (Gigant B. et al., Nature. 2005:435:519-22) (92.3% identity) and the GDP binding site (Nogales E. et al., Nature. 1995; 375:424-7) (100% identity). The colchicine binding surface (Ravelli R. B. et al., Nature. 2004; 428:198-202) was found to consist of 18 residues: V236, C239, L246, A248, K252, L253, N256, M257, T312, V313, A314, A315, V316, N348, K350, T351, A352 and I368 (FIG. 13A) and in contrast to the paclitaxel and Vinca binding sites shares only 77.9% identity between the seven β-tubulin isotypes examined.

In general, the binding site is predominantly non-polar with a slight positive charge introduced to the outer lip of the surface by residues K252 and K350. Specific substitutions within the colchicine binding surface were found to be C236S (βIII and βV), A315T (βIII and βV), V316I (βII), and T351V (βIII and βV) (FIG. 13A). Based on the isotype distribution of the substitutions within this site, the β-tubulin isotypes were divided into three classes. The type-I binding site is characterized by the canonical βI sequence and contains, for the most part, the βII and the βIV isotypes. The type-II binding site is identical to the type-I site with the exception of a V316I substitution found within only the βII isotypes. The type-III binding site has the greatest variation (C236S, A315T and T351V) and includes the βIII and βV isotypes. When the substitutions found within the type-II and type-III binding sites were mapped onto the βI-tubulin structure (Lowe J. et al., J. Mol. Biol. 2001; 313:1045-57), all were observed to be located within a region surrounding the colchicine A-ring (FIG. 13B). While none of these substitutions alter the charge of the surface, C239S and A315T change the polarity of the surface interacting with the A-ring, specifically the three non-polar phenolic methoxy groups.

Colchicine Derivatives

Figure 3A:
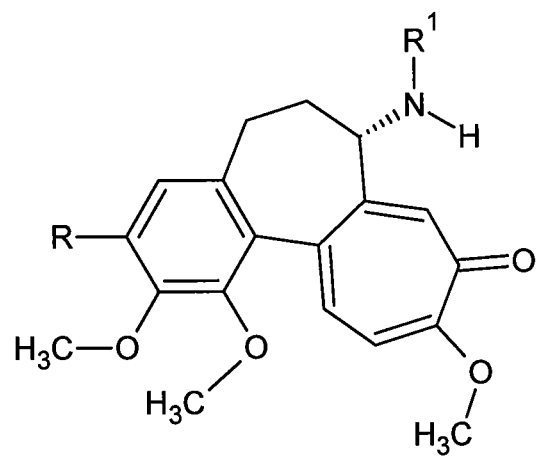
FIG. 3A shows the structure of colchicine with modifications (50) to (54) to colchicine at the R position.

As outlined in FIGS. 2-4, several modifications were made to the basic colchicine and thiocoichicine scaffolds. These modifications were composed of alkane/alkene, ester/ether, aromatic modifications to C1-demethylcolchicine and C3-demethylcolchicine (FIGS. 3 and 3A) or alkane/alkene modifications made to C3-demethylthiocolchicine (FIG. 4). Specific modifications were chosen to probe the spatial and chemical differences between the classes of isotype binding sites. Modifications made at C1 were designed to probe differences found between residues 315, 316 and 351, while those made at C3 were designed primarily to probe a non-polar cavity that is observed in the co-crystal and located beneath colchicine (Ravelli R. B. et al., Nature. 2004; 428:198-202).

Docking of Colchicine Derivatives

The basic strategy employed for computationally probing colchicine derivatives involved the generation of several ligand orientations, followed by MD-based simulated annealing and a final refinement step incorporating steepest descents and conjugate gradient minimization. Using CDOCKER (Accelrys, Inc., U.S.A.), a total of ten replicas for each of the colchicine derivatives were generated and randomly distributed around the center of the binding site models. Following the initial placement of the derivatives, they were each subjected to MD-based simulated annealing and final refinement by minimization, yielding ten docked poses for each derivative and colchicine in each of the three binding site models. The final step in the docking procedure was scoring of the refined docked poses using the Score Ligand Poses protocol of Discovery Studio. Note that the average energy values were used for the ten poses from each experiment to build the binding energy scores. This procedure yielded 630 ligand conformers, whose energy evaluations were performed.

Binding Energy Determination

Figure 14:
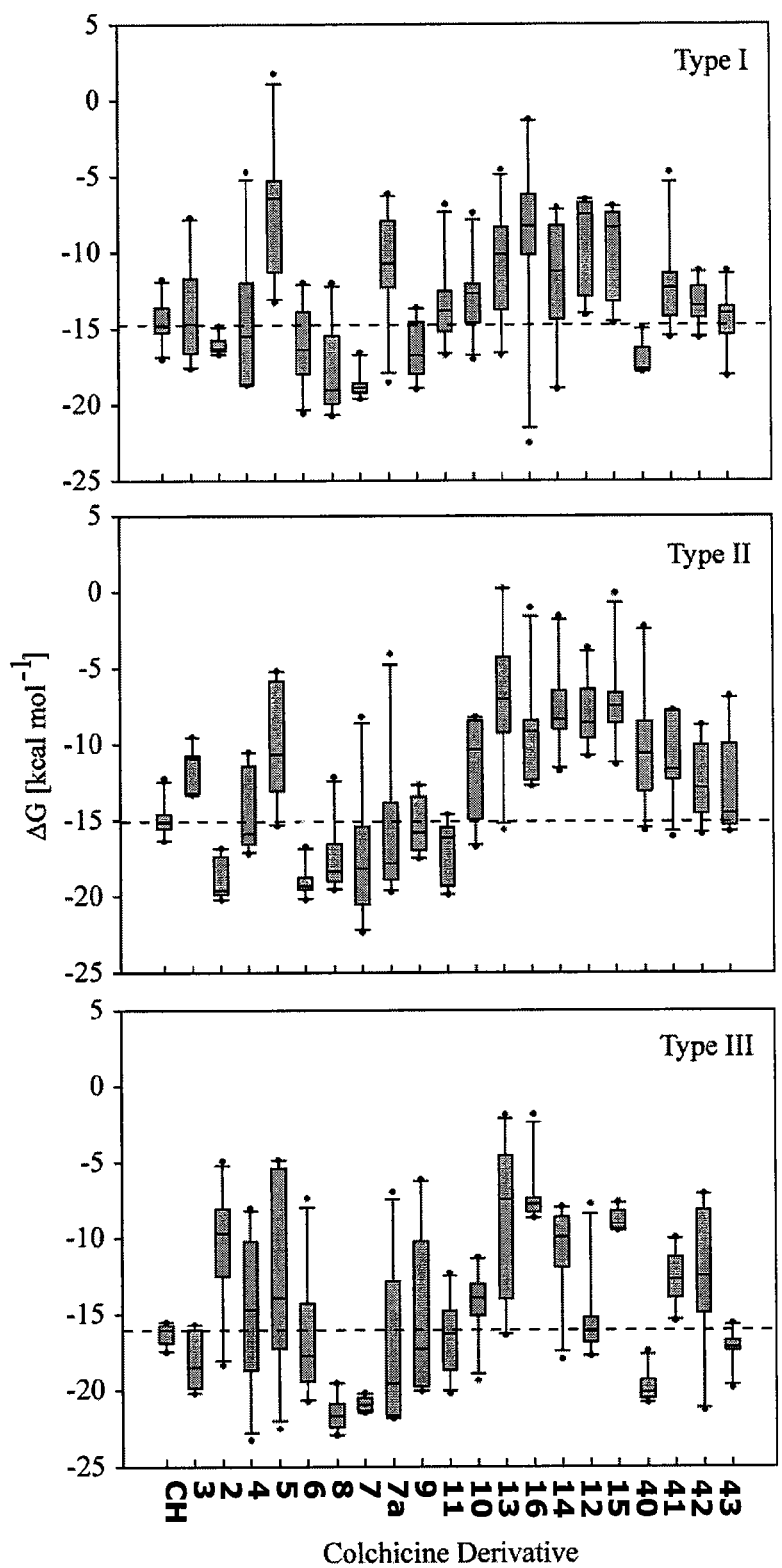
FIG. 14 shows calculated ΔG [kcal mol$^{-1}$] of colchicine and its derivatives binding to the type-I (top), type-II (middle) and type-III (bottom) β-tubulin binding sites and box plots for each of the derivatives ((3)-D-20) and colchicine (CH) were generated from energy evaluations of the ten independent docked poses, whiskers are shown for 5% and 95% confidence values.

Binding energies were determined by calculating the total potential energy of each complete systems determined in the docking steps and then subtracting the energy of the bound ligand and that of the apo-dimer (Tables 3 to 3B). When the mean binding energies for each of the colchicine derivatives were plotted, trends were consistent across all of the models and there was no apparent differentiation between the type-I, type-II or type-III binding sites (FIG. 14; CH represents colchicine). However, in all of the models, the ester/ether and aromatic derivatives at position C1 exhibited elevated binding energies when compared to colchicine, while the alkane/alkene and thiocolchicine derivatives at positions C1 and C3 had superior binding affinities (Table 3 and FIG. 14). These plots also demonstrated the range of binding energies for each of the derivatives, which is suggestive of the overall appropriateness of the docking fit (FIG. 14). Specifically, those derivatives exhibiting higher binding energies than colchicine tended to have a larger distribution in their binding energies, while those with lower overall binding energies had a narrower distribution. This trend seemed to correlate with the polarity of each of the functional groups at the C1 position. To examine the role these modifications had in vitro, all of the colchicine derivatives were then synthesized and tested in both cytotoxicity and tubulin binding assays.

From these calculations, it is clear that modification of the colchicine amide group, increase binding with tubulin in most of the second and third-generation derivatives (Table 3A and 3B). These results also suggest that, on average, modifications made to the best of the first-generation derivatives ((40), (42), (43)) had the lowest energies.

TABLE 3

Calculated and experimental values for colchicine derivative binding. CH is colchicines. The first three columns represent the mean value of ten computational docking experiments. The average binding energies (BE) [kcal mol$^{-1}$] for the three binding site models with standard errors are reported. Column four presents mean logIC$_{50}$ values [log$_{10}$ M] as determined by cytotoxicity testing on A549, HeLa, MCF-7 and CEM cell lines. Columns five and six are the k$_{on}$ rates [M$^{-1}$ s$^{-1}$] for αβII and αβIII isotypes.

| Drug | Type I (BE) | Type II (BE) | Type III (BE) | IC$_{50}$ [log10 M] | k$_{on}$ αβII | k$_{on}$ αβIII |
|---|---|---|---|---|---|---|
| CH | −14.47 ± 0.45 | −14.95 ± 0.36 | −16.29 ± 0.21 | −7.30 ± 0.05 | 132 ± 5 | 30 ± 2 |
| (2) | −16.06 ± 0.18 | −18.78 ± 0.44 | −10.45 ± 1.24 | −6.34 ± 0.09 | 35.9 | 9.4 ± 1.0 |
| (3) | −13.89 ± 1.08 | −11.42 ± 0.43 | −17.99 ± 0.57 | X$^{‡}$ | 36.6$^{†}$ | 12 ± 2.4 |
| (4) | −14.63 ± 1.45 | −14.65 ± 0.82 | −14.73 ± 1.60 | −5.27 ± 0.09 | 33.2 | 21.3 ± 5.2 |
| (5) | −7.04 ± 1.36 | −10.09 ± 1.17 | −12.75 ± 1.93 | −5.33 ± 0.10 | X$^{‡}$ | X |
| (6) | −16.15 ± 0.85 | −19.04 ± 0.31 | −16.36 ± 1.25 | −7.95 ± 0.09 | 45.7 | 15.3 ± 2.2 |
| (7) | −18.72 ± 0.27 | −17.24 ± 1.33 | −20.92 ± 0.14 | −8.12 ± 0.08 | 45.2 | 10.8 ± 0.7 |
| (7a) | −10.83 ± 1.07 | −15.75 ± 1.52 | −17.19 ± 1.69 | −6.53 ± 0.10 | 41.9 ± 0.4 | 10 ± 0.4 |
| (8) | −17.9 ± 0.91 | −17.54 ± 0.73 | −21.52 ± 0.36 | −7.86 ± 0.10 | 67.7 | 14.9 ± 0.6 |
| (9) | −16.27 ± 0.58 | −15.37 ± 0.57 | −15.32 ± 1.69 | −7.15 ± 0.08 | 50.4 | 13.7 ± 0.7 |
| (10) | −12.92 ± 0.79 | −11.59 ± 1.08 | −14.2 ± 0.69 | −6.16 ± 0.08 | 74.9 | 15.1 ± 0.4 |
| (11) | −13.44 ± 0.87 | −16.83 ± 0.63 | −16.44 ± 0.76 | −7.05 ± 0.09 | 37.9 | 9.2 ± 0.7 |
| (12) | −9.07 ± 0.95 | −8.02 ± 0.70 | −15.42 ± 0.91 | −6.30 ± 0.10 | 54.2 | 16 |
| (13) | −10.84 ± 1.15 | −6.91 ± 1.51 | −8.78 ± 1.63 | −5.13 ± 0.17 | 35.1 | 11.6 |
| (14) | −11.85 ± 1.32 | −7.67 ± 0.91 | −10.65 ± 0.93 | X* | X | 16.5 |
| (15) | −10.02 ± 0.97 | −7.24 ± 0.94 | −8.82 ± 0.22 | −6.34 ± 0.10 | 49.4 | 14.1 |
| (16) | −8.9 ± 1.85 | −9.18 ± 1.08 | −7.32 ± 0.63 | −5.26 ± 0.09 | 35.7 | 9.1 |
| (40) | −17.06 ± 0.33 | −10.15 ± 1.31 | −19.84 ± 0.32 | −7.74 ± 0.12 | 201.2 ± 10.5 | 66.9 ± 1.4 |

TABLE 3-continued

Calculated and experimental values for colchicine derivative binding. CH is colchicines.
The first three columns represent the mean value of ten computational docking experiments.
The average binding energies (BE) [kcal mol$^{-1}$] for the three binding site
models with standard errors are reported. Column four presents mean logIC$_{50}$ values
[log$_{10}$ M] as determined by cytotoxicity testing on A549, HeLa, MCF-7 and
CEM cell lines. Columns five and six are the k$_{on}$ rates [M$^{-1}$ s$^{-1}$] for αβII and αβIII isotypes.

| Drug | Type I (BE) | Type II (BE) | Type III (BE) | IC$_{50}$ [log10 M] | k$_{on}$ αβII | k$_{on}$ αβIII |
|---|---|---|---|---|---|---|
| (41) | −12.2 ± 0.94 | −10.79 ± 0.86 | −12.7 ± 0.53 | −8.39 ± 0.11 | 185.2 ± 7.8 | 65.5 ± 1.3 |
| (42) | −13.34 ± 0.42 | −12.3 ± 0.78 | −12.6 ± 1.52 | −8.44 ± 0.11 | 138.3 ± 6.5 | 53.4 ± 0.8 |
| (43) | −14.51 ± 0.63 | −13.02 ± 1.05 | −17.25 ± 0.34 | −8.67 ± 0.11 | 301.4 ± 20.1 | 98.5 ± 3.4 |

\*Did not dissolve at normal pH
† Standard deviation not available
‡ Insufficient data

TABLE 3A

Calculated values for second generation colchicine derivative binding. The average binding energies (BE) [kcal mol$^{-1}$] for the three binding site models are reported. The parent first-generation derivative can be found in the first cell of each block in the table ((7) to (9), (40), (42), and (43)) second-generation derivatives follow.

| Drug | Binding | Drug | Binding |
|---|---|---|---|
| (8) | −245.00 | (40) | −390.00 |
| (55) | −455.00 | (67) | −70.00 |
| (56) | −195.00 | (68) | −625.00 |
| (57) | −700.00 | (69) | −485.00 |
| (76) | −445.00 | (80) | −260.00 |
| (7) | −470.00 | (42) | −330.00 |
| (58) | −265.00 | (70) | −385.00 |
| (59) | 110.00 | (71) | −300.00 |
| (60) | −520.00 | (72) | −660.00 |
| (77) | −550.00 | (81) | −220.00 |
| (7a) | −575.00 | (43) | −290.00 |
| (61) | −515.00 | (73) | −455.00 |
| (62) | −505.00 | (74) | −415.00 |
| (63) | −475.00 | (75) | −665.00 |
| (78) | −705.00 | (82) | −545.00 |
| (9) | −255.00 | | |
| (64) | −390.00 | | |
| (65) | −240.00 | | |
| (66) | −545.00 | | |
| (79) | −510.00 | | |

TABLE 3B

Computed relative binding free energy of ChemRoutes colchicine derivatives in human β-tubulin isotypes (I, IIa, III, IVa) with respect to standard colchicine. Units in kJ/mol.

| Drug | Type I (BE) | Type IIa (BE) | Type III (BE) | Type IVa (BE) |
|---|---|---|---|---|
| (83) | 1.18 | −7.76 | −12.07 | −10.21 |
| (84) | 7.00 | −0.21 | −8.70 | 5.40 |
| (85) | 13.51 | −12.97 | 1.12 | 0.42 |
| (86) | −15.14 | −11.91 | −18.30 | −16.66 |
| (87) | 8.76 | −12.51 | −7.70 | 2.38 |
| (88) | −5.01 | −8.15 | 3.41 | 8.25 |
| (89) | 4.50 | −10.43 | −16.65 | −15.38 |
| (90) | 1.04 | −10.66 | −13.01 | −6.79 |
| (91) | −6.92 | −20.69 | −25.44 | −12.86 |
| (92) | −0.09 | −21.63 | −5.43 | −6.29 |
| (93) | −3.46 | −19.87 | −20.13 | −13.69 |
| (94) | −1.28 | −13.34 | −20.85 | −14.53 |

Cytotoxicity of Synthesized Colchicine Derivatives

Figure 15:
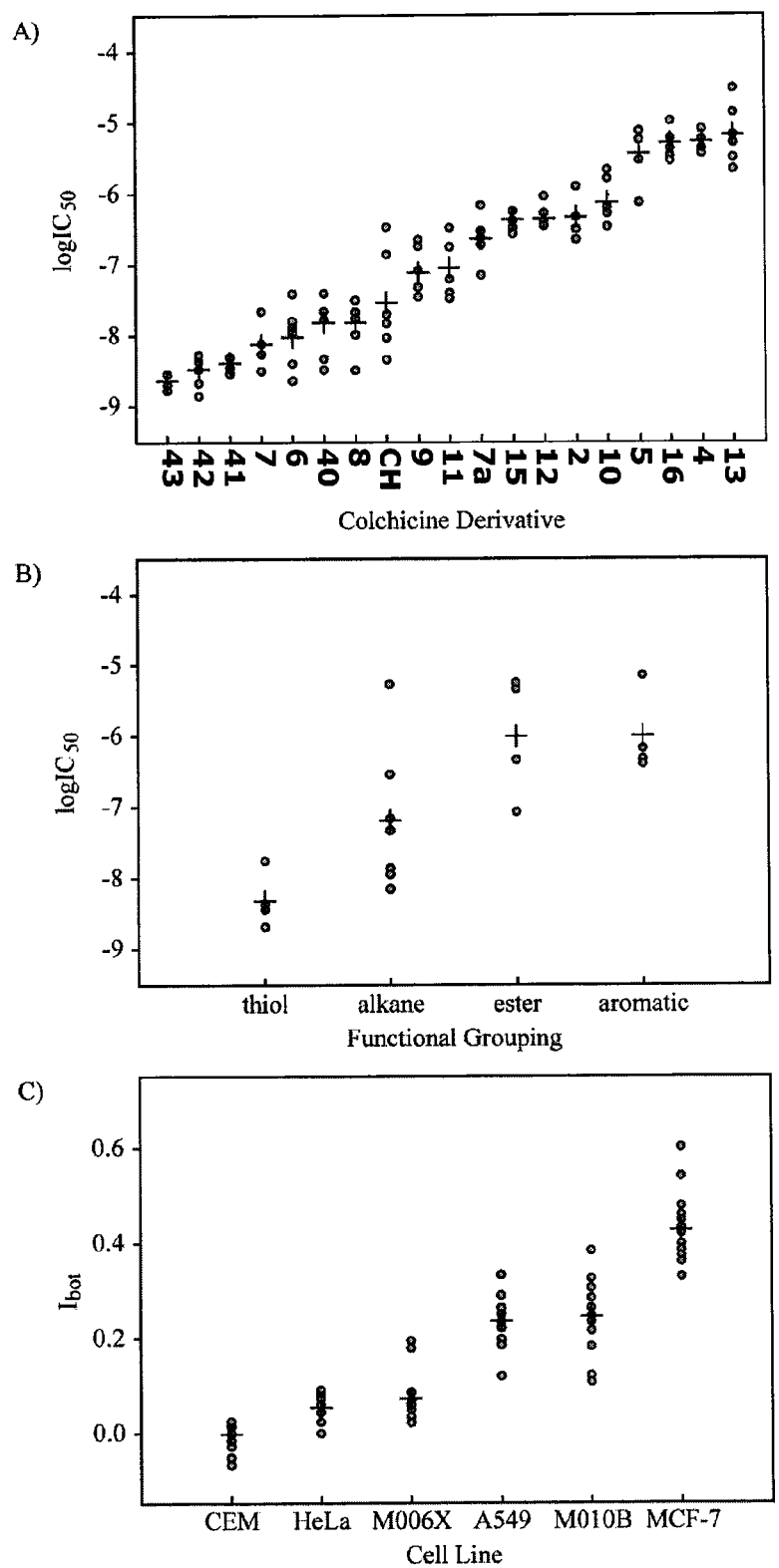
FIG. 15 shows the cytotoxicity of the colchicine derivatives.

Cytotoxicity screening was performed on a number of cell lines based on the cancer of origin and differing morphologies. Initial observations suggested that IC$_{50}$ depended on the derivative (FIG. 15A) and not on the cell line used (Table 4). Based on this observation, the mean of the log IC$_{50}$ values for each drug was taken over a set of cell lines, and that value was used as a property of the drug. The fraction of cells that survived at high drug concentration (I$_{bot}$) was dependent on the cell line tested (FIG. 15C). With respect to all the derivatives tested, 30-60% of the MCF-7 cells survived. CEM, HeLa and Jurkat cell lines had the lowest IC50 values.

Table 4 (4A and 4B). IC50 values of colchicine and various colchicine derivatives, determined by cytotoxicity testing on seven different cell lines.

TABLE 4A

| Drug | A549 Cells | HeLa Cells | MCF-7 Cells | CEM Cells |
|---|---|---|---|---|
| Colchicine | 3.84 × 10(−7) | 1.423 × 10(−7) | 3.040 × 10(−7) | 1.684 × 10(−8) |
| Thiocolchicoside | 2.917 × 10(−6) | 1.85 × 10(−2) | — | — |
| 2 | 1.482 × 10(−6) | 3.438 × 10(−7) | 5.181 × 10(−7) | 2.930 × 10(−7) |
| 3 | 5.273 × 10(−6) | 1.543 × 10(−8) | 7.274 × 10(−6) | 4.269 × 10(−7) |
| 4 | 1.038 × 10(−5) | 4.143 × 10(−6) | 6.851 × 10(−6) | 3.496 × 10(−6) |
| 5 | 7.067 × 10(−6) | 4.028 × 10(−6) | 6.065 × 10(−6) | 2.480 × 10(−6) |
| 7a | 2.408 × 10(−8) | 6.760 × 10(−9) | 9.039 × 10(−9) | 3.219 × 10(−9) |
| 7b | 2.681 × 10(−8) | 2.740 × 10(−8) | 3.985 × 10(−8) | 3.020 × 10(−9) |
| 7c | 2.853 × 10(−7) | 4.044 × 10(−8) | 7.587 × 10(−8) | 3.366 × 10(−8) |
| 8 | 2.804 × 10(−8) | 2.483 × 10(−8) | 5.055 × 10(−8) | 2.231 × 10(−9) |
| 10 | 2.337 × 10(−6) | 7.081 × 10(−7) | 5.362 × 10(−7) | 3.535 × 10(−7) |
| 11 | 3.646 × 10(−7) | 6.217 × 10(−8) | 1.641 × 10(−7) | 3.762 × 10(−8) |
| 12 | 1.671 × 10(−4) | 4.035 × 10(−7) | 6.372 × 10(−7) | 3.660 × 10(−7) |
| 13 | 1.081 × 10(−6) | 4.612 × 10(−6) | 7.489 × 10(−6) | 3.954 × 10(−6) |

TABLE 4A-continued

| Drug | A549 Cells | HeLa Cells | MCF-7 Cells | CEM Cells |
|---|---|---|---|---|
| 14 | 3.153 × 10(−6) | 3.118 × 10(−6) | 3.392 × 10(−6) | 5.094 × 10(−6) |
| 15 | 5.362 × 10(−7) | 7.279 × 10(−7) | 4.936 × 10(−7) | 3.066 × 10(−7) |
| 16 | 1.746 × 10(−5) | 5.315 × 10(−6) | 5.408 × 10(−6) | 4.236 × 10(−6) |
| 50 | 3.481 × 10(−8) | 2.673 × 10(−8) | 3.783 × 10(−8) | 3.003 × 10(−9) |
| 51 | 2.767 × 10(−9) | 3.308 × 10(−9) | 3.777 × 10(−9) | 3.547 × 10(−9) |
| 52 | 3.039 × 10(−7) | 3.305 × 10(−7) | 4.788 × 10(−7) | 2.519 × 10(−7) |
| 53 | 3.611 × 10(−9) | 3.373 × 10(−9) | 4.399 × 10(−9) | 1.806 × 10(−9) |
| 54 | 3.278 × 10(−9) | 2.947 × 10(−9) | 3.524 × 10(−9) | 2.694 × 10(−9) |

TABLE 4B

| Drug | MO10B Cells | MOO6X Cells | Jurkat Cells | ε |
|---|---|---|---|---|
| Colchicine | 1.806 × 10(−8) | 1.832 × 10(−9) | 3.818 × 10(−9) | 16.6 |
| Thiocolchicoside | — | — | — | 13.6 |
| 2 | — | — | 2.713 × 10(−7) | 18.3 |
| 3 | — | — | — | 14.4 |
| 4 | — | — | 4.660 × 10(−6) | 12 |
| 5 | 6.441 × 10(−6) | 7.912 × 10(−7) | — | 11.9 |
| 7a | — | — | — | 14.6 |
| 7b | 2.738 × 10(−8) | 1.278 × 10(−8) | — | 17.7 |
| 7c | 2.475 × 10(−7) | 3.676 × 10(−8) | — | 7.3 |
| 8 | 1.865 × 10(−8) | 3.605 × 10(−9) | 3.524 × 10(−9) | 16.6 |
| 10 | 4.238 × 10(−6) | 3.854 × 10(−7) | — | 17.3 |
| 11 | 2.719 × 10(−7) | 3.635 × 10(−8) | — | 19.5 |
| 12 | 3.977 × 10(−7) | 3.439 × 10(−7) | — | 14.5 |
| 13 | 2.804 × 10(−5) | 2.745 × 10(−6) | — | 9.9 |
| 14 | 4.030 × 10(−6) | 3.385 × 10(−6) | — | 5.9 |
| 15 | 4.035 × 10(−7) | 3.436 × 10(−7) | — | 13.2 |
| 16 | 5.646 × 10(−6) | 3.929 × 10(−6) | — | 14 |
| 50 | 2.989 × 10(−8) | 4.413 × 10(−9) | — | 18.8 |
| 51 | — | — | 3.478 × 10(−9) | 15.1 |
| 52 | 2.879 × 10(−7) | 3.750 × 10(−8) | — | 11.4 |
| 53 | 3.346 × 10(−9) | 1.698 × 10(−9) | 3.235 × 10(−9) | 17.3 |
| 54 | 2.957 × 10(−9) | — | 2.705 × 10(−9) | 13.6 |

Upon examining the average values of the $IC_{50}$ values (Table 3), a partitioning of the colchicine derivatives became evident (FIGS. 15A and 15B). The derivatives with $IC_{50}$ values similar to that of colchicine ((8), (9), (11), and (40)), contained non-polar straight chain alkanes at position C1. Those derivatives with $IC_{50}$ values stronger than colchicine ((6), (7), (41), (42), and (43)) were non-polar groups at either the C1 or C3 positions. Without being bound by theory, the stronger $IC_{50}$ values observed for these compounds may be indicative of the increased non-polar surface interactions with tubulin due to increased occupancy of the binding site. The computational results are also reinforced by cytotoxicity experiments. The most potent derivative in the experiments (43) had an IC50 of 2.13±0.77 nM, a value at least 15 fold stronger than that previously reported for either colchicine (29±2.2 nM) or paclitaxel (36.7±2.4 nM) (Cragg G. M. et al., Anticancer agents from natural products. CRC Press; 2005).

Binding Kinetics

Figure 16:
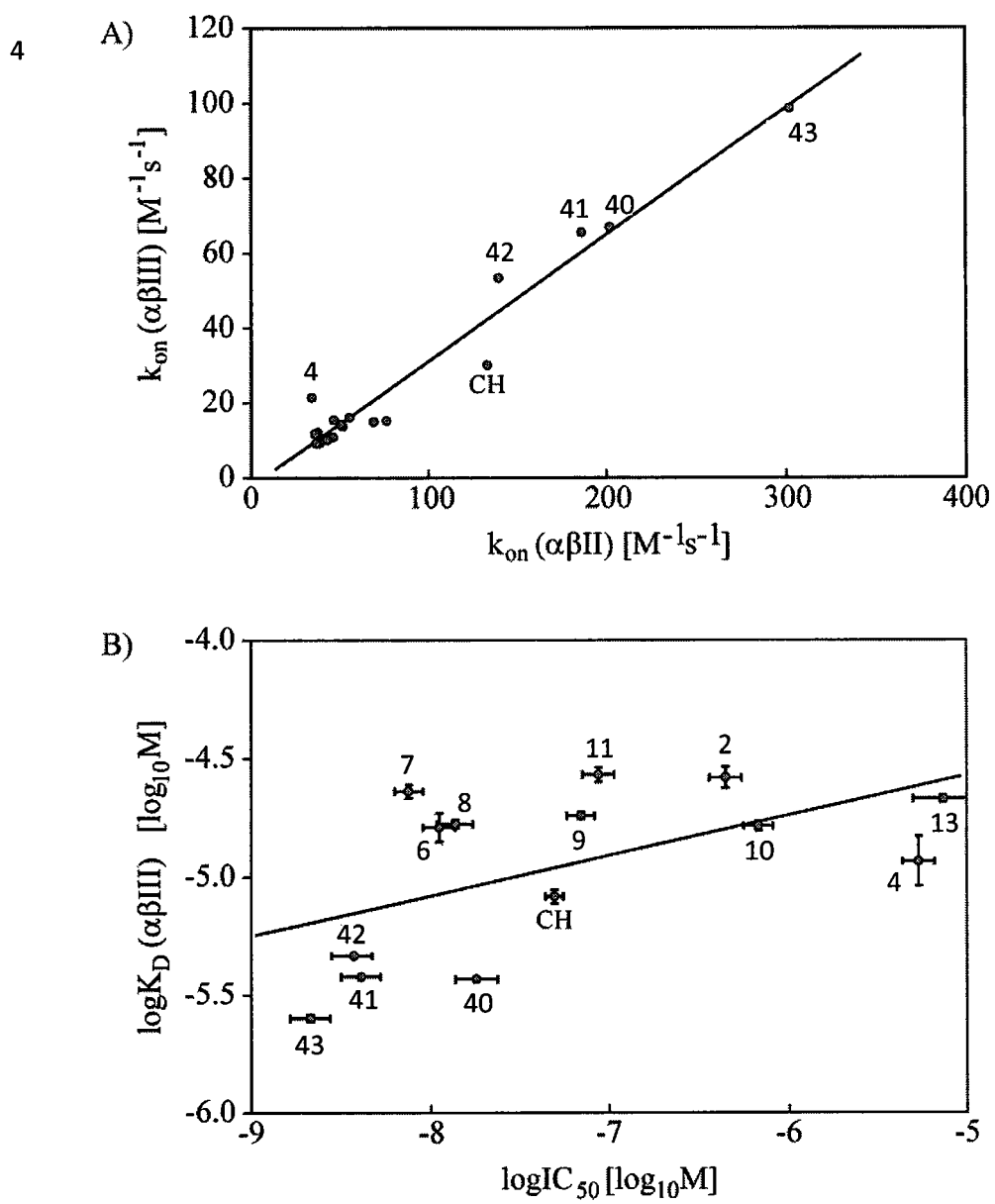
FIG. 16 shows binding kinetics of colchicine derivatives to the αβII and αβIII tubulin dimers.

Having established a partitioning of derivative effects in cytotoxicity assays, their binding kinetics to purified bovine βII or βIII tubulin isotypes (Table 3) were examined. All $K_d$ values were calculated by assuming a $k_{off}$=2.5×10$^{-4}$ s$^{-1}$ for colchicine as determined for βII or βIII previously (Banerjee A. et al., J. Biol. Chem. 1992; 267:13335-9). Since tubulin is normally isolated from bovine brain tissue, the predominant isotypes available were only βII and βIII (Banerjee A. et al., J. Biol. Chem. 1992; 267:13335-9). This provided a representative sample of the type-I and type-III colchicine binding sites. Comparing $k_{on}$(αβII) to $k_{on}$(αβIII), demonstrated that all the derivatives have a high positive correlation ($r^2$=0.94). Compounds (40) to (43) had improved $k_{on}$ for both, and assumedly a greater affinity. A correlation was determined between the $IC_{50}$ values and the on-rate for binding to α62 III (FIG. 16B). Note that $k_{on}$ (αβII) and $k_{on}$ (αβIII) are mutually correlated (FIG. 16A), hence only one of them needs to be linked to $IC_{50}$. A reasonable correlation between these two sets of data ($r^2$=0.44) supports the dissimilar cytotoxicity of the compounds against each of the cell lines is a result of different binding affinity to β-tubulin.

Correlations to Calculated Binding Energy

Figure 17:
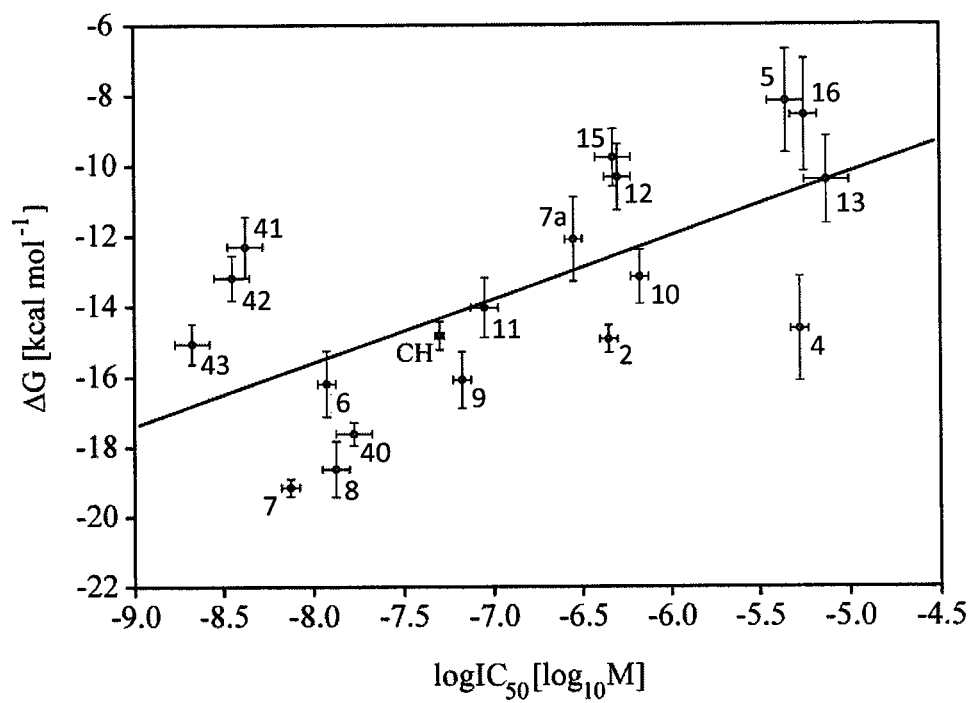
FIG. 17 shows a correlation between the calculated ΔG [kcal mol$^{-1}$] and the log $IC_{50}$ for colchicine derivatives studied; values for the computed binding energy of colchicine and colchicine derivatives (except for (5) and D14) to the weighted type-I, type-II and type-III binding site models were plotted against the log $IC_{50}$ values across A549, HeLa, MCF-7 and CEM cell lines; and the line is a fit of the data with $R^2=0.42$.

When comparing weighted cytotoxicity results to binding energies calculated from the β-tubulin models, a moderate positive correlation ($R^2$=0.42) was observed (FIG. 17). Expression information for the five β-tubulin isotypes in the A549, HeLa, MCF-7 and CEM cell lines was obtained from several sources and an average expression value of 95% for the type-I and 5% for the type-III binding sites was used for weighting the ΔG values obtained from binding calculations (Cuechiarelli V. et al., Cell Motil. Cytoskeleton; 2008; 65:675-85; Kavallaris M. et al., J. Clin. Invest. 1997; 100: 1282-93; Tommasi S. et al., Int. J. Cancer, 2007; 120:2078-85; and Banerjee A., Biochem. Biophys. Res. Commun. 2002; 293:598-601). A positive correlation confirms that modeling of the colchicine binding site is useful in designing colchicine derivatives that could differentiate between tubulin isotypes.

Cytotoxicity of Colchicine Derivatives

Materials and Methods

A set of seven colchicine derivatives purchased from ChemRoutes was screened against a set of four cell lines obtained from the Cross Cancer Institute's frozen human cell line collection. A full factorial experimental design was used, for a total of 28 cases.

Cell lines used were A549 (Human lung adenocarcinoma), NCI-H226 (Human lung squamous cell carcinoma), CCRF-CEM (Human T-lymphoblastoids from ALL), and MCF-7 (Human mammary gland adenocarcinoma).

Compounds used are listed in the following Table:

| Compound Name | Structure |
|---|---|
| 1 | 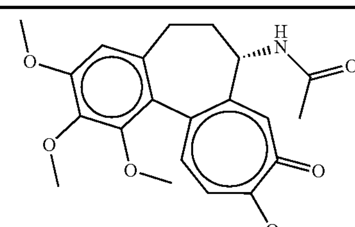 |

-continued

| Compound Name | Structure |
|---|---|
| 28a | 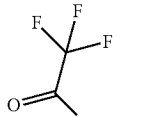 |
| 39 | 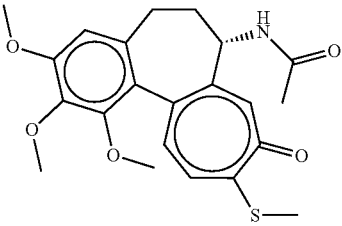 |
| 47a | 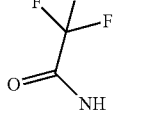 |

For each (cell line, compound) pair, the following conditions were used, with each condition being assigned to a lane on a microtiter plate:

a. Seven or eight concentration levels between $1 \times 10^{-10}$ M and $1 \times 10^{-3}$ M.
b. A control with cells and media only.
c. A control with cells, media and DMSO only. The DMSO was at a concentration approximately equal to that used in the highest drug concentration level.

Additionally, 6-8 replicates (wells) of each condition were done on the plate. Drug solutions were prepared by dissolving the solid compounds in DMSO and then diluting in water. An approximately equal number of cells were introduced into each well of the plate and cells were incubated for 72 hours. An MTS assay was performed and absorbance values were measured with a spectrophotometer. Finally, a log IC50 parameter was calculated by fitting a 4-parameter logistic model to the data using an implementation of the Levenberg-Marquardt algorithm.

Results

The following log IC50 values were obtained, with lower log IC50 values indicating a more potent compound, i.e. a compound that has cytotoxic activity at a lower concentration.

| Cell Line | Compound | logIC50 [1] |
|---|---|---|
| A549 | 1 | −7.3 |
| A549 | 28a | −6.2 |
| A549 | 39 | −7.0 |
| A549 | 47a | −7.2 |
| CCRF-CEM | 1 | −8.1 |
| CCRF-CEM | 28a | −7.4 |
| CCRF-CEM | 39 | −8.7 |
| CCRF-CEM | 47a | −8.2 |
| MCF-7 | 1 | [2] |
| MCF-7 | 28a | [2] |
| MCF-7 | 39 | −4.0 |
| MCF-7 | 47a | −3.9 |
| NCI-H226 | 1 | −7.3 |
| NCI-H226 | 28a | −6.5 |
| NCI-H226 | 39 | −8.1 |
| NCI-H226 | 47a | −7.3 |

[1]: logIC50 values have a precision of +/−0.5 or better
[2]: logIC50 was not obtained
[3]: Treatment effect was confounded by DMSO toxicity In summary, if the log IC50 values are averaged over the A549, CCRF-CEM, and NCI-H226 cell lines, then we find the order of potency of the tested compounds, from most potent to least potent, is:

(39)>(1)>(47a)>(28a)

What is claimed is:
1. A compound of Formula XE and/or XF:

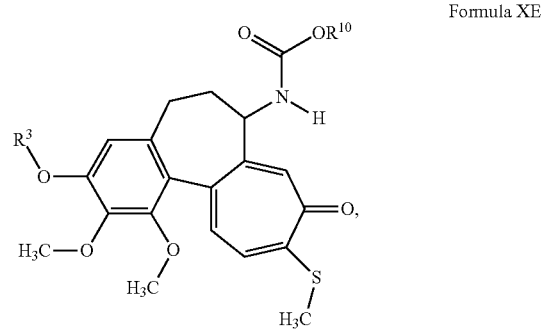

Formula XE

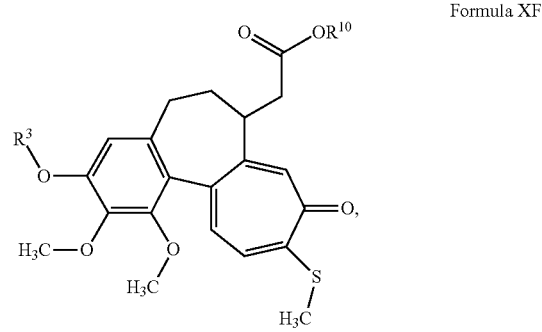

Formula XF a pharmaceutically-acceptable salt, hydrate, solvate, tautomer, optical isomer, or combination thereof,
wherein:
when the compound is Formula XE, $R^3$ is selected from a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

when the compound is Formula XF, $R^3$ is selected from H, a halo group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and wherein $R^{10}$ is a methyl group.

2. The compound according to claim 1, wherein $R^3$ is selected from a substituted or unsubstituted $C_1$-$C_6$ alkyl, a substituted or unsubstituted $C_2$-$C_6$ alkenyl, or $C_1$-$C_6$ alkylene-O-alkyl.

3. The compound according to claim 1, wherein $R^3$ is selected from a substituted or unsubstituted alkyl group, a substituted or unsubstituted alkenyl group, a substituted or unsubstituted alkynyl group, a substituted or unsubstituted aromatic group, a substituted or unsubstituted heteroaromatic group, a substituted or unsubstituted carbocyclic group, or a substituted or unsubstituted heterocyclic group.

4. The compound according to claim 1,
wherein $R^3$ is selected from a substituted or unsubstituted alkyl, CH$_2$OH, a substituted or unsubstituted haloalkyl, a substituted or unsubstituted hydroxyalkyl, a substituted or unsubstituted cyanoalkyl, a substituted or unsubstituted alkenyl, a substituted or unsubstituted alkynyl, a substituted or unsubstituted cycloalkyl, a substituted or unsubstituted cycloalkenyl, a substituted or unsubstituted alkylcycloalkyl, a substituted or unsubstituted alkylcycloalkenyl, a substituted or unsubstituted heterocycloalkyl, a substituted or unsubstituted alkylheterocycloalkyl, a substituted or unsubstituted heterocycloalkenyl, a substituted or unsubstituted alkylheterocycloalkenyl, a substituted or unsubstituted aryl, a substituted or unsubstituted heteroaryl, a substituted or unsubstituted alkylaryl, a substituted or unsubstituted alkylheteroaryl, alkylene-O-alkyl, alkylene-O-cycloalkyl, alkylene-O-heterocycloalkyl, alkylene-O-alkylene-cycloalkyl, or alkylene-O-alkyleneheterocycloalkyl.

5. The compound according to claim 1, wherein $R^3$ is selected from a substituted or unsubstituted $C_1$-$C_6$ alkyl, a substituted or unsubstituted $C_2$-$C_6$ alkenyl, a substituted or unsubstituted $C_1$-$C_6$ alkylcarbonyl, $C_1$-$C_6$ alkylene-O-alkyl, a substituted or unsubstituted alkylcycloalkyl, a substituted or unsubstituted alkylaryl, or a substituted or unsubstituted alkylheteroaryl.

6. A method for treating a cancer in a mammal, comprising administering to the mammal a therapeutically effective amount of the compound according to claim 1.

7. The method according to claim 6, wherein the cancer is selected from lung cancer, cervical cancer, ovarian cancer, cancer of CNS, skin cancer, prostate cancer, sarcoma, breast cancer, leukemia, colorectal cancer, head cancer, neck cancer or kidney cancer.

* * * * *

UNITED STATES PATENT AND TRADEMARK OFFICE
CERTIFICATE OF CORRECTION

PATENT NO.         : 9,458,101 B2
APPLICATION NO.    : 13/392454
DATED              : October 4, 2016
INVENTOR(S)        : Tuszynski et al.

It is certified that error appears in the above-identified patent and that said Letters Patent is hereby corrected as shown below:

On the Title Page

Item (75) please remove inventors "Dorota Bartusik" and "Boguslaw Tomanek".

Item (73) please correct "National Research Council of Canada" to "Alberta Health Services."

Signed and Sealed this
Sixth Day of February, 2018

Joseph Matal
*Performing the Functions and Duties of the*
*Under Secretary of Commerce for Intellectual Property and*
*Director of the United States Patent and Trademark Office*